(12) United States Patent
Endou et al.

(10) Patent No.: US 7,335,482 B2
(45) Date of Patent: Feb. 26, 2008

(54) METHOD USING NEUTRAL AMINO ACID TRANSPORTER EXPRESSING CELL

(75) Inventors: Hitoshi Endou, Sagamihara (JP); Yoshikatsu Kanai, Hachioji (JP)

(73) Assignee: Japan Science and Technology Corporation, Saitama (JP)

( * ) Notice: Subject to any disclaimer, the term of this patent is extended or adjusted under 35 U.S.C. 154(b) by 0 days.

(21) Appl. No.: 10/913,263

(22) Filed: Aug. 5, 2004

(65) Prior Publication Data

US 2005/0019812 A1    Jan. 27, 2005

Related U.S. Application Data

(62) Division of application No. 09/786,389, filed as application No. PCT/JP99/04789 on Sep. 3, 1999.

(30) Foreign Application Priority Data

Sep. 3, 1998  (JP)  ................................. 10-249993
Sep. 2, 1999  (JP)  ................................. 11-248546

(51) Int. Cl.
*G01N 33/53*  (2006.01)

(52) U.S. Cl. ....................... 435/7.2; 435/325

(58) Field of Classification Search ..................... None
See application file for complete search history.

(56) References Cited

U.S. PATENT DOCUMENTS 5,843,727 A * 12/1998 Hillman et al. ............ 435/69.8

OTHER PUBLICATIONS

Prasad et al., "Human LAT1, a Subunit of System L Amino Acid Transporter: Molecular Cloning and Transport Function," *Biochem. Biophys. Res. Commun.* 255:2 pp. 283-288 (1999).
Tsurudome et al., "Cutting Edge: Primary Structure of the Light Chain of Fusion Regulatory Protein-1/CD98/4F2 Predicts a Protein with Multiple Transmembrane Domains That is Almost Identical to the Amino Acid Transporter E16," *J. Immunol.* 162:5 pp. 2462-2466 (1999).
Mastroberardino et al., "Amino-acid transport by heterodimers of 4F2hc/CD98 and members of a permease family," *Nature* 395:6699 pp. 288-291 (1999).
Kanai et al., "Expression Cloning and Characterization of a Transporter for Large Neutral Amino Acids Activated by the Heavy Chain of 4F2 Antigen, (CD98)," *J. Biol. Chem.* 273:37 pp. 23629-23632 (1998).
Nakamura et al., "4F2(CD98) Heavy Chain is Associated Covalently with an Amino Acid Transporter and Controls Intracellular Trafficking and Membrane Topology of 4F2 Heterodimer," *Journal of Biol. Chem.* 274:5 p. 3009-3016 (1999).
Haynes et al., "Characterization of a Monoclonal Antibody (4F2) that Binds to Human Monocytes and a Subset of Activated Lymphocytes," *J. Immunol.* 128:4 1409-1414 (1981).

Hemler et al., "Characterization of the Antigen Recognized by the Monoclonal Antibody (4F2): Different Molecular Forms on Human T and B Lymphoblastoid Cell Lines," *J. Immunol.* 129:2 pp. 623-628 (1982).
Teixeira et al., "Primary Structure of Human 4F2 Antigen Heavy Chain Predicts a Transmembrane Protein with a Cytoplasmic NH2 Terminus," *J. Biol. Chem.* 262:20 pp. 9574-9580 (1987).
Lumadue et al., "Cloning, sequence analysis, and expression of thelarge subunit of the human lymphocyte activation antigen 4F2," *Proc. Natl. Acad. Sci. USA* 84:24 pp. 9204-9208 (1987).
Quackenbush et al., "Molecular Cloning of complementary DNAs Encoding the Heavy Chain of the Human 4F2 Cell Surface Antigen: A Type II Membrane Glycoprotein Involved in Normal and Neoplastic Cell Growth," *Proc. Natl. Acad. Sci. USA* 84:18 pp. 6526-6530 (1987).
Broer et al., "The 4F2hc surface antigen is necessary for expression of system L-like neutral amino acid-transport activity in C6-BU-1 rat glioma cells: evidence from expression studies in *Xenopus laevis* oocytes," *Biochem. J.* 312:3 pp. 863-870 (1995).
Yao et al., "Cloning and Functional Expression of a cDNA from Rat Jejunal Epithemlium Encoding a Protein (4F2hc) with System y+L Amino Acid Transport Activity," *Biochem. J.* 330:2 pp. 745-752 (1998).
Gaugitsch et al., "A Novel Expressed, Integral Membrane Protein Linked to Cell Activation," *J. Biol. Chem.* 267:16 pp. 11267-11273 (1992).
Torrents et al., "Identification and Characterization of a Membrane Protein (y+L Amino Acid Transporter-1) That Associates with 4F2hc to Encode the Amino Acid Transport Activity y+L," *The Journal of Biological Chemistry* 273:49 pp. 32437-32445 (1998).

(Continued)

Primary Examiner—Michael Pak
(74) Attorney, Agent, or Firm—Peter F. Corless; Christine C. O'Day; Edwards Angell Palmer & Dodge LLP

(57) ABSTRACT

A novel amino acid transporter molecule mediating transportation of amino acids, which are nutrients essentially required in the survival and proliferation of various normal cells constituting a living body and various pathology-associated abnormal cells such as tumor cells, into cells and being expressed specifically in tumor cells compared with normal cells; and drugs for treating various pathogenic conditions such as tumor (cancer) which are obtained by identifying and isolating the above amino acid transporter molecule and identifying a substance capable of inhibiting the biological activity and/or expression of this molecule. Intensive studies were made to identify a tumor cell membrane surface molecule associating or interacting with a cell membrane surface 4F2hc molecule seemingly playing an important role in the activation of an unknown amino acid transporter. As a result, a gene encoding the novel amino acid transporter molecule, which mediates the incorporation of various neutral amino acids, various drugs or physiological substances into cells, has been found out and a substance capable of inhibiting the incorporation of amino acids via this molecule and thus inhibiting the proliferation of tumor cells has been also found out.

9 Claims, 28 Drawing Sheets

OTHER PUBLICATIONS

Estevez et al., "The amino acid transport system y+L/4F2hc is a heteromultimeric complex," *The FASEB Journal* 12:1319-1329 (1998).

Broer et al., "Discrimination of two amino acid transport activities in 4F2 heavy chain-expressing *Xenopus laevis* oocytes," *Biochem. J.* 333:549-554 (1998).

Wells et al., "The 4F2 Antigen Heavy Chain Induces Uptake of Neutral and Dibasic Amino Acids in *Xenopus* Oocytes," *The Journal of Biological Chemistry* 267:2 pp. 15285-15288 (1992).

Gottesdiener et al., "Isolation and Structural Characterization of the Human 4F2 Heavy-Chain Gene, and Inducible Gene Involved in T-Lymphocyte Activation," *Molecular and Cellular Biology* 8:9 pp. 3809-3819 (1988).

Spindler et al., "Characterization of early aldosterone-induced RNAs identified in A6 kidney epithelia," *Pflugers Arch.* 434:323-331(1997).

Broer et al., "Association of 4F2hc with light chains LAT1, LAT2 or y+LAT2 requires different domains," *Biochem. J.* 355:725-731 (2001).

D K. Kim et al., "Expression of L-type Amino Acid Transporter 1 (LAT1) and 4F2 Heavy Chain (4F2hc) in Oral Squamous Cell Carcinoma and its Precursor Lesions", Anti-Cancer Research, vol. 24, pp. 1671-1676 (2004).

J.H. Yoon et al., "Expression and Functional Characterization of the System L Amino Acid Transporter in KB Human Oral Epidermoid Carcinoma Cells", Cancer Letters, vol. 205, pp. 215-226 (2004).

O. Yanagida et al., "human L-type Amino Acid Transporter 1 (LAT1): Characterization of Function and Expression in Tumor Cell Lines", Bioch. et Bioph. Acta, vol. 1514, pp. 291-302 (2001).

J.H. Yoon et al., "Amino Acid Transport System L is Differently Expressed in Human Normal Oral Keratinocytes and Human Oral Cancer Cells", Cancer Letters, vol. 222, pp. 237-245 (2005).

S. Tamai et al., "Expression of L-Type Amino Acid Transporter 1 in a Rat Model of Liver Metastasis: Positive Correlation with Tumor Size", Cancer Detection and Prevention, vol. 25, No. 5, pp. 439-445 (2001).

D.K. Kim et al., "Characterization of the System L Amino Acid Transporter in T24 Human Bladder Carcinoma Cells", Biosh. et Bioph. Acta, vol. 1565, pp. 112-122 (2002).

K. Nakanishi et al., "LAT1 Expression in Normal Lung and in Atypical Adenomatous Hyperplasia and Adenocarcinoma of the Lung", Virchows Arch, vol. 448, pp. 142-150 (2006).

D.K. Kim et al., "System L-Amino Acid Transporters are Differently Expressed in Rat Astrocyte and C6 Glioma Cells", Neuroscience Research, vol. 50, pp. 437-446 (2004).

H. Nawashiro et al., "L-Type Amino Acid Transporter 1 as a Potential Molecular Target in Human Astrocytic Tumors", Int. J. Cancer, vol. 119, pp. 484-492 (2006).

* cited by examiner

Figure 1

```
MAGAGPKRRALAAPA--AEEKEE--AREKMLAAKSADGSA-PAGEGEGVT
|| || |||| ||||  | | ||  |||||| |   |  | |  ||||||
MAVAGAKRRAVAAPATTAAE-EERQAREKMLEARRGDG-ADP--EGEGVT

LQRNITLLNGVAIIVGTIIGSGIFVTPTGVLKEAGSPGLALVVWAACGVF
|||||| |||||||||||||||||||||||||||||||||  ||| ||||
LQRNITLINGVAIIVGTIIGSGIFVTPTGVLKEAGSPGLSLVVWAVCGVF

SIVGALCYAELGTTISKSGGDYAYMLEVYGSLPAFLKLWIELLIIRPSSQ
|||||||||||||||||||||||||||||||||||||||||||||||||
SIVGALCYAELGTTISKSGGDYAYMLEVYGSLPAFLKLWIELLIIRPSSQ

YIVALVFATYLLKPLFPTCPVPEEAAKLVACLCVLLLTAVNCYSVKAATR
||||||||||||| |||||||||||||||||||||||||||||||||||
YIVALVFATYLLKPVFPTCPVPEEAAKLVACLCVLLLTAVNCYSVKAATR

VQDAFAAAKLLALALIILLGFVQIGK--G--DVSNLDPNFSFEGTKLDVG
|||||||||||||||||||||| |   ||    |    |   ||| |||
VQDAFAAAKLLALALIILLGFIQMGKDIGQGDASNLHQKLSFEGTNLDVG

NIVLALYSGLFAYGGWNYLNFVTEEMINPYRNLPLAIIISLPIVTLVYVL
||||||||||||||||||||||||||||||||||||||||||||||||||
NIVLALYSGLFAYGGWNYLNFVTEEMINPYRNLPLAIIISLPIVTLVYVL

TNLAYFTTLSTEQMLSSEAVAVDFGNYHLGVMSWIIPVFVGLSCFGSVNG
|||||||||||| |||| |||||||||||||||||||||||||||||||
TNLAYFTTLSTNQMLTSEAVAVDFGNYHLGVMSWIIPVFVGLSCFGSVNG

SLFTSSRLFFVGSREGHLPSILSMIHPQLLTPVPSLVFTCVMTLLYAFSK
||||||||||||||||||||||||||||||||||||||||||| |||| 
SLFTSSRLFFVGSREGHLPSILSMIHPQLLTPVPSLVFTCVMTLMYAFSR

DIFSVINFFSFFNWLCVALAIIGMIWLRHRKPELERPIKVNLALPVFFIL
|||| ||||||||||||||||| ||||| |||||||||||||||||||||
DIFSIINFFSFFNWLCVALAIIGMMWLRFKKPELERPIKVNLALPVFFIL

ACLFLIAVSFWKTPVECGIGFTIILSGLPVYFFGVWWKNKPKWLLQGIFS
|||||||||||||| ||||||  ||||||||||||||||||||| | |||
ACLFLIAVSFWKTPLECGIGFAIILSGLPVYFFGVWWKNKPKWILQVIFS

TTVLCQKLMQVVPQET..................................
|||||||||||||||
VTVLCQKLMQVVPQET..................................
```

Figure 24
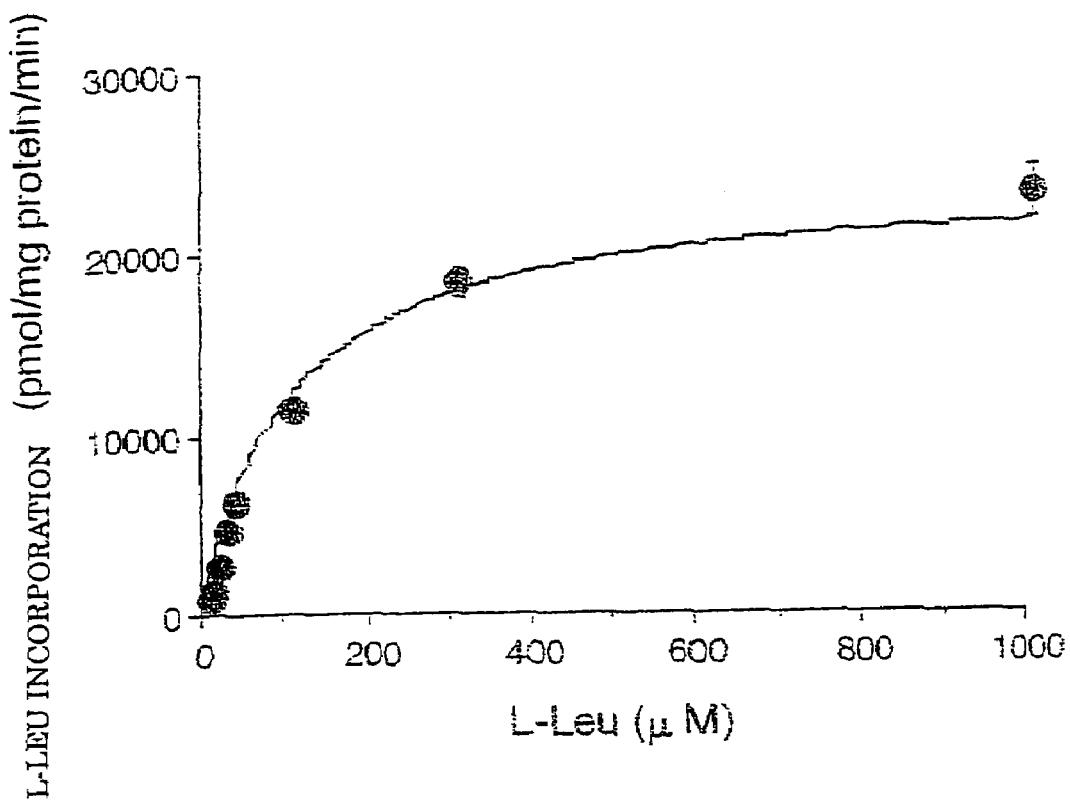
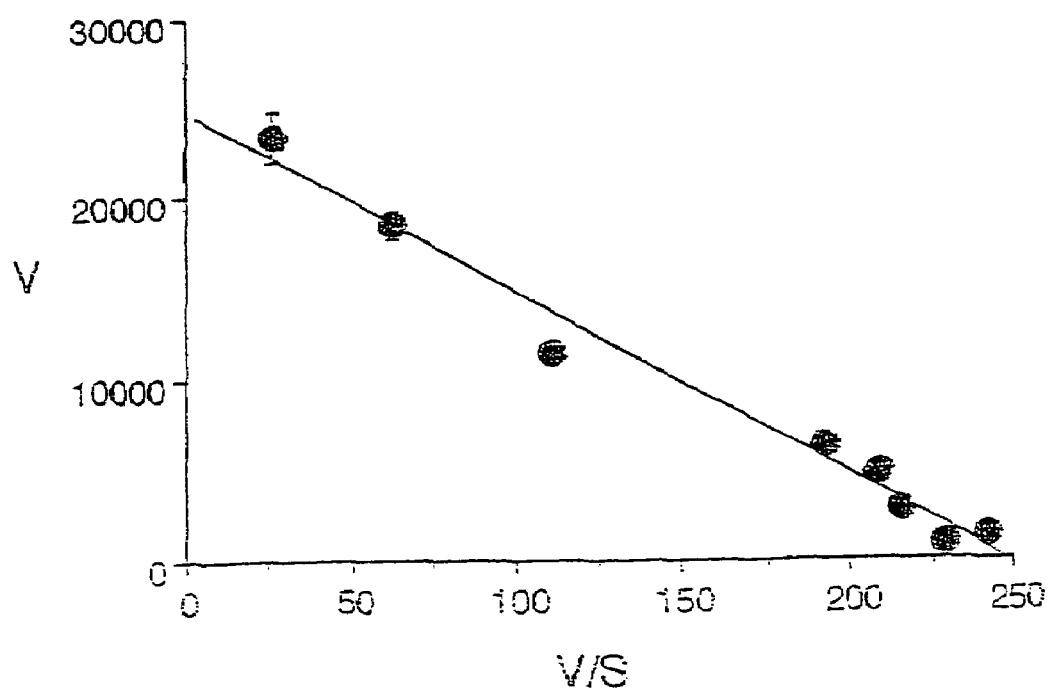

SEQUENCE LISTING

<160> NUMBER OF SEQ ID NOS: 27

<210> SEQ ID NO 1
<211> LENGTH: 4539
<212> TYPE: DNA
<213> ORGANISM: Homo sapiens
<220> FEATURE:
<221> NAME/KEY: 5'UTR
<222> LOCATION: (1)..(65)
<220> FEATURE:
<221> NAME/KEY: CDS
<222> LOCATION: (66)..(1589)
<220> FEATURE:
<221> NAME/KEY: 3'UTR
<222> LOCATION: (1590)..(4474)

<400> SEQUENCE: 1

```
cggcgcgcac actgctcgct gggccgcggc tcccgggtgt cccaggcccg gccggtgcgc      60 agagc atg gcg ggt gcg ggc ccg aag cgg cgc gcg cta gcg gcg ccg gcg     110
      Met Ala Gly Ala Gly Pro Lys Arg Arg Ala Leu Ala Ala Pro Ala
        1               5                  10                 15 gcc gag gag aag gaa gag gcg cgg gag aag atg ctg gcc gcc aag agc      158
Ala Glu Glu Lys Glu Glu Ala Arg Glu Lys Met Leu Ala Ala Lys Ser
                20                  25                  30 gcg gac ggc tcg gcg ccg gca ggc gag ggc gag ggc gtg acc ctg cag      206
Ala Asp Gly Ser Ala Pro Ala Gly Glu Gly Glu Gly Val Thr Leu Gln
            35                  40                  45 cgg aac atc acg ctg ctc aac ggc gtg gcc atc atc gtg ggg acc att      254
Arg Asn Ile Thr Leu Leu Asn Gly Val Ala Ile Ile Val Gly Thr Ile
        50                  55                  60 atc ggc tcg ggc atc ttc gtg acg ccc acg ggc gtg ctc aag gag gca      302
Ile Gly Ser Gly Ile Phe Val Thr Pro Thr Gly Val Leu Lys Glu Ala
    65                  70                  75 ggc tcg ccg ggg ctg gcg ctg gtg gtg tgg gcc gcg tgc ggc gtc ttc      350
Gly Ser Pro Gly Leu Ala Leu Val Val Trp Ala Ala Cys Gly Val Phe
80                  85                  90                  95 tcc atc gtg ggc gcg ctc tgc tac gcg gag ctc ggc acc acc atc tcc      398
Ser Ile Val Gly Ala Leu Cys Tyr Ala Glu Leu Gly Thr Thr Ile Ser
                100                 105                 110 aaa tcg ggc ggc gac tac gcc tac atg ctg gag gtc tac ggc tcg ctg      446
Lys Ser Gly Gly Asp Tyr Ala Tyr Met Leu Glu Val Tyr Gly Ser Leu
            115                 120                 125 ccc gcc ttc ctc aag ctc tgg atc gag ctc ctc atc atc cgg cct tca      494
Pro Ala Phe Leu Lys Leu Trp Ile Glu Leu Leu Ile Ile Arg Pro Ser
        130                 135                 140 tcg cag tac atc gtg gcc ctg gtc ttc gcc acc tac ctc ctc aag ccg      542
Ser Gln Tyr Ile Val Ala Leu Val Phe Ala Thr Tyr Leu Leu Lys Pro
    145                 150                 155 ctc ttc ccc acc tgc ccg gtg ccc gag gag gca gcc aag ctc gtg gcc      590
Leu Phe Pro Thr Cys Pro Val Pro Glu Glu Ala Ala Lys Leu Val Ala
160                 165                 170                 175 tgc ctc tgc gtg ctg ctc ctc acg gcc gtg aac tgc tac agc gtg aag      638
Cys Leu Cys Val Leu Leu Leu Thr Ala Val Asn Cys Tyr Ser Val Lys
                180                 185                 190
```

```
gcc gcc acc cgg gtc cag gat gcc ttt gcc gcc gcc aag ctc ctg gcc         686
Ala Ala Thr Arg Val Gln Asp Ala Phe Ala Ala Ala Lys Leu Leu Ala
            195                 200                 205 ctg gcc ctg atc atc ctg ctg ggc ttc gtc cag atc ggg aag ggt gat         734
Leu Ala Leu Ile Ile Leu Leu Gly Phe Val Gln Ile Gly Lys Gly Asp
            210                 215                 220 gtg tcc aat cta gat ccc aac ttc tca ttt gaa ggc acc aaa ctg gat         782
Val Ser Asn Leu Asp Pro Asn Phe Ser Phe Glu Gly Thr Lys Leu Asp
            225                 230                 235 gtg ggg aac att gtg ctg gca tta tac agc ggc ctc ttt gcc tat gga         830
Val Gly Asn Ile Val Leu Ala Leu Tyr Ser Gly Leu Phe Ala Tyr Gly
240                 245                 250                 255 gga tgg aat tac ttg aat ttc gtc aca gag gaa atg atc aac ccc tac         878
Gly Trp Asn Tyr Leu Asn Phe Val Thr Glu Glu Met Ile Asn Pro Tyr
                260                 265                 270 aga aac ctg ccc ctg gcc atc atc atc tcc ctg ccc atc gtg acg ctg         926
Arg Asn Leu Pro Leu Ala Ile Ile Ile Ser Leu Pro Ile Val Thr Leu
                275                 280                 285 gtg tac gtg ctg acc aac ctg gcc tac ttc acc acc ctg tcc acc gag         974
Val Tyr Val Leu Thr Asn Leu Ala Tyr Phe Thr Thr Leu Ser Thr Glu
                290                 295                 300 cag atg ctg tcg tcc gag gcc gtg gcc gtg gac ttc ggg aac tat cac        1022
Gln Met Leu Ser Ser Glu Ala Val Ala Val Asp Phe Gly Asn Tyr His
            305                 310                 315 ctg ggc gtc atg tcc tgg atc atc ccc gtc ttc gtg ggc ctg tcc tgc        1070
Leu Gly Val Met Ser Trp Ile Ile Pro Val Phe Val Gly Leu Ser Cys
320                 325                 330                 335 ttc ggc tcc gtc aat ggg tcc ctg ttc aca tcc tcc agg ctc ttc ttc        1118
Phe Gly Ser Val Asn Gly Ser Leu Phe Thr Ser Ser Arg Leu Phe Phe
                340                 345                 350 gtg ggg tcc cgg gaa ggc cac ctg ccc tcc atc ctc tcc atg atc cac        1166
Val Gly Ser Arg Glu Gly His Leu Pro Ser Ile Leu Ser Met Ile His
                355                 360                 365 cca cag ctc ctc acc ccc gtg ccg tcc ctc gtg ttc acg tgt gtg atg        1214
Pro Gln Leu Leu Thr Pro Val Pro Ser Leu Val Phe Thr Cys Val Met
            370                 375                 380 acg ctg ctc tac gcc ttc tcc aag gac atc ttc tcc gtc atc aac ttc        1262
Thr Leu Leu Tyr Ala Phe Ser Lys Asp Ile Phe Ser Val Ile Asn Phe
            385                 390                 395 ttc agc ttc ttc aac tgg ctc tgc gtg gcc ctg gcc atc atc ggc atg        1310
Phe Ser Phe Phe Asn Trp Leu Cys Val Ala Leu Ala Ile Ile Gly Met
400                 405                 410                 415 atc tgg ctg cgc cac aga aag cct gag ctt gag cgg ccc atc aag gtg        1358
Ile Trp Leu Arg His Arg Lys Pro Glu Leu Glu Arg Pro Ile Lys Val
                420                 425                 430 aac ctg gcc ctg cct gtg ttc ttc atc ctg gcc tgc ctc ttc ctg atc        1406
Asn Leu Ala Leu Pro Val Phe Phe Ile Leu Ala Cys Leu Phe Leu Ile
            435                 440                 445 gcc gtc tcc ttc tgg aag aca ccc gtg gag tgt ggc atc ggc ttc acc        1454
Ala Val Ser Phe Trp Lys Thr Pro Val Glu Cys Gly Ile Gly Phe Thr
            450                 455                 460 atc atc ctc agc ggg ctg ccc gtc tac ttc ttc ggg gtc tgg tgg aaa        1502
Ile Ile Leu Ser Gly Leu Pro Val Tyr Phe Phe Gly Val Trp Trp Lys
465                 470                 475 aac aag ccc aag tgg ctc ctc cag ggc atc ttc tcc acg acc gtc ctg        1550
Asn Lys Pro Lys Trp Leu Leu Gln Gly Ile Phe Ser Thr Thr Val Leu
480                 485                 490                 495 tgt cag aag ctc atg cag gtg gtc ccc cag gag aca tag ccaggaggcc        1599
Cys Gln Lys Leu Met Gln Val Val Pro Gln Glu Thr
                500                 505
```

```
gagtggctgc cggaggagca tgcgcagagg ccagttaaag tagatcacct cctcgaaccc    1659
actccggttc cccgcaaccc acagctcagc tgcccatccc agtccctcgc cgtccctccc    1719
aggtcgggca gtggaggctg ctgtgaaaac tctggtacga atctcatccc tcaactgagg    1779
gccagggacc caggtgtgcc tgtgctcctg cccaggagca gcttttggtc tccttgggcc    1839
ctttttccct tccctccttt gtttacttat atatatattt ttttaaaact taaattttgg    1899
gtcaacttga caccactaag atgattttt aaggagctgg gggaaggcag gagccttcct    1959
ttctcctgcc caagggccc agccctggg caaacagagc tactgagact tggaacctca    2019
ttgctacgac agacttgcac tgaagccgga cagctgccca gacacatggg cttgtgacat    2079
tcgtgaaaac caaccctgtg ggcttatgtc tctgccttag ggtttgcaga gtggaaactc    2139
agccgtaggg tggcactggg aggggtggg ggatctgggc aaggtgggtg attcctccca    2199
ggaggtgctt gaggcccccga tggactcctg accataatcc tagccccgag acaccatcct    2259
gagccaggga acagccccag ggttgggggg tgccggcatc tcccctagct caccaggcct    2319
ggcctctggg cagtgtggcc tcttggctat ttctgttcca gttttggagg ctgagttctg    2379
gttcatgcag acaaagccct gtccttcagt cttctagaaa cagagacaag aaaggcagac    2439
acaccgcggc caggcaccca tgtgggcgcc caccctgggc tccacacagc agtgtcccct    2499
gccccagagg tcgcagctac cctcagcctc caatgcattg gcctctgtac cgcccggcag    2559
cccctttctgg ccggtgctgg gttcccactc ccggcctagg cacctccccg ctctccctgt    2619
cacgctcatg tcctgtcctg gtcctgatgc ccgttgtcta ggagacagag ccaagcactg    2679
ctcacgtctc tgccgcctgc gtttggaggc ccctgggctc tcacccagtc cccacccgcc    2739
tgcagagagg gaactagggc accccttgtt tctgttgttc ccgtgaattt ttttcgctat    2799
gggaggcagc cgaggcctgg ccaatgcggc ccactttcct gagctgtcgc tgcctccatg    2859
gcagcagcca aggacccca gaacaagaag accccccgc aggatccctc ctgagctcgg    2919
ggggctctgc cttctcaggc cccgggcttc ccttctcccc agccagaggt ggagccaagt    2979
ggtccagcgt cactccagtg ctcagctgtg gctggaggag ctggcctgtg gcacagccct    3039
gagtgtccca agccgggagc caacgaagcc ggacacggct tcactgacca gcggctgctc    3099
aagccgcaag ctctcagcaa gtgcccagtg gagcctgccg ccccccacctg ggcaccggga    3159
ccccctcacc atccagtggg cccggagaaa cctgatgaac agtttgggga ctcaggacca    3219
gatgtccgtc tctcttgctt gaggaatgaa gacctttatt caccccctgcc ccgttgcttc    3279
ccgctgcaca tggacagact tcacagcgtc tgctcatagg acctgcatcc ttcctgggga    3339
cgaattccac tcgtccaagg dacagcccac ggtctggagg ccgaggacca ccagcaggca    3399
ggtggactga ctgtgttggg caagacctct tccctctggg cctgttctct tggctgcaaa    3459
taaggacagc agctggtgcc ccacctgcct ggtgcattgc tgtgtgaatc caggaggcag    3519
tggacatcgt aggcagccac ggccccgggt ccaggagaag tgctccctgg aggcacgcac    3579
cactgcttcc cactggggcc ggcggggccc acgcacgacg tcagcctctt accttcccgc    3639
ctcggctagg ggtcctcggg atgccgttct gttccaacct cctgctctgg gaggtggaca    3699
tgcctcaagg atacagggag ccggcggcct ctcgacggca cgcacttgcc tgttggctgc    3759
tgcggctgtg ggcgagcatg ggggctgcca gcgtctgttg tggaaagtag ctgctagtga    3819
aatggctggg gccgctgggg tccgtcttca cactgcgcag gtctcttctg ggcgtctgag    3879
ctggggtggg agctcctccg cagaaggttg gtggggggtc cagtctgtga tccttggtgc    3939
tgtgtgcccc actccagcct ggggacccca cttcagaagg taggggccgt gtcccgcggt    3999
```

-continued

```
gctgactgag gcctgcttcc ccctccccct cctgctgtgc tggaattcca cagggaccag    4059
ggccaccgca ggggactgtc tcagaagact tgattttttcc gtcccttttt ctccacactc    4119
cactgacaaa cgtccccagc ggtttccact tgtgggcttc aggtgttttc aagcacaacc    4179
caccacaaca agcaagtgca ttttcagtcg ttgtgctttt tgttttgtg ctaacgtctt    4239 actaatttaa agatgctgtc ggcaccatgt ttatttattt ccagtggtca tgctcagcct    4299
tgctgctctg cgtggcgcag gtgccatgcc tgctccctgt ctgtgtccca gccacgcagg    4359
gccatccact gtgacgtcgg ccgaccaggc tggacaccct ctgccgagta atgacgtgtg    4419
tggctgggac cttctttatt ctgtgttaat ggctaacctg ttacactggg ctgggttggg    4479
tagggtgttc tggcttttttt gtggggtttt tatttttaaa gaaacactca atcatcctag    4539
```

<210> SEQ ID NO 2
<211> LENGTH: 507
<212> TYPE: PRT
<213> ORGANISM: Homo sapiens

<400> SEQUENCE: 2

```
Met Ala Gly Ala Gly Pro Lys Arg Arg Ala Leu Ala Ala Pro Ala Ala
  1               5                  10                  15

Glu Glu Lys Glu Glu Ala Arg Glu Lys Met Leu Ala Ala Lys Ser Ala
              20                  25                  30

Asp Gly Ser Ala Pro Ala Gly Glu Gly Glu Gly Val Thr Leu Gln Arg
          35                  40                  45

Asn Ile Thr Leu Leu Asn Gly Val Ala Ile Ile Val Gly Thr Ile Ile
      50                  55                  60

Gly Ser Gly Ile Phe Val Thr Pro Thr Gly Val Leu Lys Glu Ala Gly
  65                  70                  75                  80

Ser Pro Gly Leu Ala Leu Val Val Trp Ala Ala Cys Gly Val Phe Ser
              85                  90                  95

Ile Val Gly Ala Leu Cys Tyr Ala Glu Leu Gly Thr Thr Ile Ser Lys
         100                 105                 110

Ser Gly Gly Asp Tyr Ala Tyr Met Leu Glu Val Tyr Gly Ser Leu Pro
         115                 120                 125

Ala Phe Leu Lys Leu Trp Ile Glu Leu Leu Ile Ile Arg Pro Ser Ser
         130                 135                 140

Gln Tyr Ile Val Ala Leu Val Phe Ala Thr Tyr Leu Leu Lys Pro Leu
145                 150                 155                 160

Phe Pro Thr Cys Pro Val Pro Glu Glu Ala Ala Lys Leu Val Ala Cys
                165                 170                 175

Leu Cys Val Leu Leu Leu Thr Ala Val Asn Cys Tyr Ser Val Lys Ala
                180                 185                 190

Ala Thr Arg Val Gln Asp Ala Phe Ala Ala Lys Leu Leu Ala Leu
             195                 200                 205

Ala Leu Ile Ile Leu Leu Gly Phe Val Gln Ile Gly Lys Gly Asp Val
         210                 215                 220

Ser Asn Leu Asp Pro Asn Phe Ser Phe Glu Gly Thr Lys Leu Asp Val
225                 230                 235                 240

Gly Asn Ile Val Leu Ala Leu Tyr Ser Gly Leu Phe Ala Tyr Gly Gly
                245                 250                 255

Trp Asn Tyr Leu Asn Phe Val Thr Glu Glu Met Ile Asn Pro Tyr Arg
                260                 265                 270

Asn Leu Pro Leu Ala Ile Ile Ile Ser Leu Pro Ile Val Thr Leu Val
            275                 280                 285
```

```
Tyr Val Leu Thr Asn Leu Ala Tyr Phe Thr Thr Leu Ser Thr Glu Gln
        290                 295                 300

Met Leu Ser Ser Glu Ala Val Ala Val Asp Phe Gly Asn Tyr His Leu
305                 310                 315                 320

Gly Val Met Ser Trp Ile Ile Pro Val Phe Val Gly Leu Ser Cys Phe
                325                 330                 335

Gly Ser Val Asn Gly Ser Leu Phe Thr Ser Ser Arg Leu Phe Phe Val
            340                 345                 350

Gly Ser Arg Glu Gly His Leu Pro Ser Ile Leu Ser Met Ile His Pro
        355                 360                 365

Gln Leu Leu Thr Pro Val Pro Ser Leu Val Phe Thr Cys Val Met Thr
    370                 375                 380

Leu Leu Tyr Ala Phe Ser Lys Asp Ile Phe Ser Val Ile Asn Phe Phe
385                 390                 395                 400

Ser Phe Phe Asn Trp Leu Cys Val Ala Leu Ala Ile Ile Gly Met Ile
                405                 410                 415

Trp Leu Arg His Arg Lys Pro Glu Leu Glu Arg Pro Ile Lys Val Asn
            420                 425                 430

Leu Ala Leu Pro Val Phe Phe Ile Leu Ala Cys Leu Phe Leu Ile Ala
        435                 440                 445

Val Ser Phe Trp Lys Thr Pro Val Glu Cys Gly Ile Gly Phe Thr Ile
    450                 455                 460

Ile Leu Ser Gly Leu Pro Val Tyr Phe Phe Gly Val Trp Trp Lys Asn
465                 470                 475                 480

Lys Pro Lys Trp Leu Leu Gln Gly Ile Phe Ser Thr Thr Val Leu Cys
                485                 490                 495

Gln Lys Leu Met Gln Val Val Pro Gln Glu Thr
            500                 505

<210> SEQ ID NO 3
<211> LENGTH: 3455
<212> TYPE: DNA
<213> ORGANISM: Rat
<220> FEATURE:
<221> NAME/KEY: 5'UTR
<222> LOCATION: (1)..(63)
<220> FEATURE:
<221> NAME/KEY: CDS
<222> LOCATION: (64)..(1602)
<220> FEATURE:
<221> NAME/KEY: 3'UTR
<222> LOCATION: (1603)..(3455)

<400> SEQUENCE: 3
cgcggagagc ggctcggccg cgcgcacgcc gggtatccag gccgagccgg gaacgtcgag      60 agc atg gcg gtc gcg ggc gca aag cgg cgc gcg gtt gcg gcc ccc gcg      108
    Met Ala Val Ala Gly Ala Lys Arg Arg Ala Val Ala Ala Pro Ala
    1               5                   10                  15 acg acg gcg gcg gag gag gag cgg cag gcg cgg gag aag atg ctg gag      156
Thr Thr Ala Ala Glu Glu Glu Arg Gln Ala Arg Glu Lys Met Leu Glu
                20                  25                  30 gcg cgg cgc ggg gac ggc gcg gac ccc gag ggc gaa ggc gtg acc ctg      204
Ala Arg Arg Gly Asp Gly Ala Asp Pro Glu Gly Glu Gly Val Thr Leu
            35                  40                  45 cag cgc aat atc aca ctg atc aat ggt gtg gcc atc ata gtg ggc acc      252
Gln Arg Asn Ile Thr Leu Ile Asn Gly Val Ala Ile Ile Val Gly Thr
        50                  55                  60
```

```
atc atc ggt tcg ggc atc ttc gtg acg ccc acc ggc gtg ctc aag gaa      300
Ile Ile Gly Ser Gly Ile Phe Val Thr Pro Thr Gly Val Leu Lys Glu
        65                  70                  75 gcc ggc tcg ccc gga ctg tcg ctt gtg gtg tgg gct gtg tgc ggc gtc      348
Ala Gly Ser Pro Gly Leu Ser Leu Val Val Trp Ala Val Cys Gly Val
 80                  85                  90                  95 ttc tcc atc gtg ggc gca ctg tgc tac gcg gag ctg ggc act acc atc      396
Phe Ser Ile Val Gly Ala Leu Cys Tyr Ala Glu Leu Gly Thr Thr Ile
                100                 105                 110 tca aag tca ggc ggc gac tat gcc tac atg cta gag gtc tac ggc tcg      444
Ser Lys Ser Gly Gly Asp Tyr Ala Tyr Met Leu Glu Val Tyr Gly Ser
            115                 120                 125 ctg ccc gcc ttc ctc aag ctc tgg atc gag ctc ctc att cgg ccc          492
Leu Pro Ala Phe Leu Lys Leu Trp Ile Glu Leu Leu Ile Ile Arg Pro
        130                 135                 140 tcc tca cag tac atc gtg gcg ctg gtc ttc gcc aca tac ctg ctc aag      540
Ser Ser Gln Tyr Ile Val Ala Leu Val Phe Ala Thr Tyr Leu Leu Lys
145                 150                 155 ccg gtc ttc ccc act tgt ccc gtg ccc gag gag gct gcc aag ctc gtg      588
Pro Val Phe Pro Thr Cys Pro Val Pro Glu Glu Ala Ala Lys Leu Val
160                 165                 170                 175 gcc tgc ctc tgc gtg cta cta ctc acg gct gtg aac tgc tac agt gtg      636
Ala Cys Leu Cys Val Leu Leu Leu Thr Ala Val Asn Cys Tyr Ser Val
                180                 185                 190 aag gct gct acc cgt gtg cag gat gcc ttt gcg gct gcc aaa ctg ctg      684
Lys Ala Ala Thr Arg Val Gln Asp Ala Phe Ala Ala Ala Lys Leu Leu
            195                 200                 205 gcc ctg gcc ctc atc atc ctc ctc ggc ttc atc cag atg gga aag gac      732
Ala Leu Ala Leu Ile Ile Leu Leu Gly Phe Ile Gln Met Gly Lys Asp
        210                 215                 220 ata gga caa ggg gat gca tcc aac ctg cac cag aag ttg tcc ttt gaa      780
Ile Gly Gln Gly Asp Ala Ser Asn Leu His Gln Lys Leu Ser Phe Glu
225                 230                 235 ggc acc aat ctg gac gtg ggg aac att gtg ttg gca ttg tac agt ggc      828
Gly Thr Asn Leu Asp Val Gly Asn Ile Val Leu Ala Leu Tyr Ser Gly
240                 245                 250                 255 ctc ttc gcc tac gga gga tgg aac tat ctg aat ttt gtc acg gag gag      876
Leu Phe Ala Tyr Gly Gly Trp Asn Tyr Leu Asn Phe Val Thr Glu Glu
                260                 265                 270 atg atc aac ccc tac agg aac ctc ccc ctg gcc atc atc atc tcc ttg      924
Met Ile Asn Pro Tyr Arg Asn Leu Pro Leu Ala Ile Ile Ile Ser Leu
            275                 280                 285 ccc att gtc acc ctg gtc tat gtg ctg acg aac ctg gcc tac ttc act      972
Pro Ile Val Thr Leu Val Tyr Val Leu Thr Asn Leu Ala Tyr Phe Thr
        290                 295                 300 acc ctg tct acc aac cag atg ctg aca tct gaa gcc gtg gct gtg gat     1020
Thr Leu Ser Thr Asn Gln Met Leu Thr Ser Glu Ala Val Ala Val Asp
305                 310                 315 ttt ggg aac tac cac ctg gga gtc atg tcc tgg atc att cct gtc ttc     1068
Phe Gly Asn Tyr His Leu Gly Val Met Ser Trp Ile Ile Pro Val Phe
320                 325                 330                 335 gtg ggc ttg tcc tgc ttc ggc tct gtc aat ggg tct ctg ttc acg tcc     1116
Val Gly Leu Ser Cys Phe Gly Ser Val Asn Gly Ser Leu Phe Thr Ser
                340                 345                 350 tca aga ctg ttc ttc gtg gga tcc agg gag ggc cac ctg cct tcc atc     1164
Ser Arg Leu Phe Phe Val Gly Ser Arg Glu Gly His Leu Pro Ser Ile
            355                 360                 365 ctc tcc atg atc cac cca cag ctt ctg aca ccg gtg cca tca ctg gtg     1212
Leu Ser Met Ile His Pro Gln Leu Leu Thr Pro Val Pro Ser Leu Val
        370                 375                 380
```

-continued

```
ttc acg tgt gtc atg acc ctg atg tac gcc ttc tcc aga gac atc ttc      1260
Phe Thr Cys Val Met Thr Leu Met Tyr Ala Phe Ser Arg Asp Ile Phe
    385                 390                 395 tcc atc atc aac ttc ttc agc ttc ttc aac tgg ctg tgt gtg gcc ctg      1308
Ser Ile Ile Asn Phe Phe Ser Phe Phe Asn Trp Leu Cys Val Ala Leu
400                 405                 410                 415 gcc atc atc ggc atg atg tgg ctc cgc ttt aag aag cct gag ctg gag      1356
Ala Ile Ile Gly Met Met Trp Leu Arg Phe Lys Lys Pro Glu Leu Glu
                420                 425                 430 cgt ccc atc aag gtg aat ctg gcc ctc cca gtg ttc ttt atc ctg gcc      1404
Arg Pro Ile Lys Val Asn Leu Ala Leu Pro Val Phe Phe Ile Leu Ala
            435                 440                 445 tgc ctc ttc ctc atc gcc gtg tcc ttc tgg aag aca ccc ctg gag tgc      1452
Cys Leu Phe Leu Ile Ala Val Ser Phe Trp Lys Thr Pro Leu Glu Cys
        450                 455                 460 ggc att ggc ttc gcc atc atc ctc agc ggg ctg cct gtc tac ttc ttt      1500
Gly Ile Gly Phe Ala Ile Ile Leu Ser Gly Leu Pro Val Tyr Phe Phe
    465                 470                 475 ggt gtg tgg tgg aaa aac aag ccc aaa tgg atc ctg cag gtc atc ttc      1548
Gly Val Trp Trp Lys Asn Lys Pro Lys Trp Ile Leu Gln Val Ile Phe
480                 485                 490                 495 tcc gtg acc gtg ctc tgc cag aag ctg atg cag gtg gtt cct cag gag      1596
Ser Val Thr Val Leu Cys Gln Lys Leu Met Gln Val Val Pro Gln Glu
                500                 505                 510 act tag ccacgtgtcc tgggtgccgc gggagagtgc actgtgactg cttccagaca      1652
Thr actcacctttt ggaaaagcag cgtccaggcc cgtcatcccc acagctccag tgagcaccac    1712
taactatctt aacaccatcc gctgtccctc aaaggtcagg tgtccacagt ggccgtgaaa    1772
gaaacctggt acgaatttgg tcccagatgg tgaccatcca tgcatacata gcagccactg    1832
tgaggtgtgc tgtggcctga ggctggtct ttctgacttt ggggactgcc acatctgggc    1892
tttctcctct atgatttttt gttttgtttt tgtagcgttc atttgggtca agtttacact    1952
accgagatga ttattttttg acaaaacagg gtagcaaaga gcaggagatg gtgtggccgg    2012
acagtccggc tctgagtggg aactgcaggc cacagctctt ctccgactgt tgttcgttca    2072
gtagcacatt gtggctggag gggaccacat cactgtcacc aagtcagaac tactgagact    2132
caaacatcac cttttccact gtggacttgc actgacaaac ggacgatgaa tgtgctagct    2192
tgggtttgag ttttctgggt ctgtcctaga gatgaaaccc caacctgacc cacgaggcag    2252
agctctactg tgggtcattt gttccattgt aaatgcagag ctccggtctg accactctga    2312
agtcctggtg attccccttc ccctggctcc aaatgaaaga cctctgcagc cataaccta    2372 gtggcacctg gccaccaact gtcaactgcg gggccatgtg ctcctgtgca cacaagctgg    2432
ctctacacat tcaaggggca ctgctctggg tcttactccc tgtcccaccc cagctctcct    2492
agaaccagac cggcaccatg gggctccacc acacacctct gtccacctcc ataattcctg    2552
agactgctag cagctctctg tcaagtcacc accgtccccc ctcagccccc cgggccactg    2612
ttcaaaagaa taggcaccaa ctacccttct gctctctgcc acctgtgtga cgtgaccact    2672
ccagctccct gagcgtgaaa actgctggct acgtgctgct gtccctcctg tgtgggacca    2732
gtctgttccg gggagacggt tgagtccagc agcacatcca ctgaagcagc tgatctgact    2792
gaaggacttg agggcatgag aatccccgc tggcccttcc attgcctcag agctggcctc    2852
cctgaggggg tgtcaactgg agtgtctact gtgaagctct tacatagtgg caccctgata    2912
tctcctgggg ttcccttgtg ttggggtgag gaggcagagg tcaaggtcag agtgccccta    2972
```

-continued

```
gaaggctctc cagagatgtg aactcaggtc cccagacaca agcctgggtt caaagggcag    3032
ggcaagtctt ggtccacgtt catggtgctg acccaggccc tctgagaagg ccctgtcatt    3092
cctattctga tgtcctgagg acgcccatct gtaggttttt ggttttaaat caagccacag    3152
ccacagtcat ttgcccaat gctttgcatt gtgttgtcct aacacatcac tgccctgtgg     3212 aaccccctg cctggccctt ttcagtggtc agtgtccagt gctgggtacg gtgtgttccc     3272
accacactgg gtccacctgc tgtgccactg gactagtgc tgtggttgta atgtctttta    3332
ctattgtatt aatgactagt ctgttacatt agactggggg tggggtgcaa gggtctgctg    3392
gtttgtgagg cttttgatt gggggggtgg tttgttttt tttttaaag ctattggagt      3452 tct                                                                   3455
```

<210> SEQ ID NO 4
<211> LENGTH: 512
<212> TYPE: PRT
<213> ORGANISM: Rat

<400> SEQUENCE: 4

```
Met Ala Val Ala Gly Ala Lys Arg Arg Ala Val Ala Ala Pro Ala Thr
 1               5                   10                  15

Thr Ala Ala Glu Glu Glu Arg Gln Ala Arg Glu Lys Met Leu Glu Ala
                20                  25                  30

Arg Arg Gly Asp Gly Ala Asp Pro Glu Gly Glu Gly Val Thr Leu Gln
            35                  40                  45

Arg Asn Ile Thr Leu Ile Asn Gly Val Ala Ile Val Gly Thr Ile
        50                  55                  60

Ile Gly Ser Gly Ile Phe Val Thr Pro Thr Gly Val Leu Lys Glu Ala
65                  70                  75                  80

Gly Ser Pro Gly Leu Ser Leu Val Val Trp Ala Val Cys Gly Val Phe
                85                  90                  95

Ser Ile Val Gly Ala Leu Cys Tyr Ala Glu Leu Gly Thr Thr Ile Ser
                100                 105                 110

Lys Ser Gly Gly Asp Tyr Ala Tyr Met Leu Glu Val Tyr Gly Ser Leu
            115                 120                 125

Pro Ala Phe Leu Lys Leu Trp Ile Glu Leu Leu Ile Ile Arg Pro Ser
        130                 135                 140

Ser Gln Tyr Ile Val Ala Leu Val Phe Ala Thr Tyr Leu Leu Lys Pro
145                 150                 155                 160

Val Phe Pro Thr Cys Pro Val Pro Glu Glu Ala Ala Lys Leu Val Ala
                165                 170                 175

Cys Leu Cys Val Leu Leu Leu Thr Ala Val Asn Cys Tyr Ser Val Lys
                180                 185                 190

Ala Ala Thr Arg Val Gln Asp Ala Phe Ala Ala Ala Lys Leu Leu Ala
            195                 200                 205

Leu Ala Leu Ile Ile Leu Leu Gly Phe Ile Gln Met Gly Lys Asp Ile
        210                 215                 220

Gly Gln Gly Asp Ala Ser Asn Leu His Gln Lys Leu Ser Phe Glu Gly
225                 230                 235                 240

Thr Asn Leu Asp Val Gly Asn Ile Val Leu Ala Leu Tyr Ser Gly Leu
                245                 250                 255

Phe Ala Tyr Gly Gly Trp Asn Tyr Leu Asn Phe Val Thr Glu Glu Met
                260                 265                 270

Ile Asn Pro Tyr Arg Asn Leu Pro Leu Ala Ile Ile Ile Ser Leu Pro
            275                 280                 285
```

-continued

```
Ile Val Thr Leu Val Tyr Val Leu Thr Asn Leu Ala Tyr Phe Thr Thr
    290                 295                 300

Leu Ser Thr Asn Gln Met Leu Thr Ser Glu Ala Val Ala Val Asp Phe
305                 310                 315                 320

Gly Asn Tyr His Leu Gly Val Met Ser Trp Ile Ile Pro Val Phe Val
                325                 330                 335

Gly Leu Ser Cys Phe Gly Ser Val Asn Gly Ser Leu Phe Thr Ser Ser
            340                 345                 350

Arg Leu Phe Phe Val Gly Ser Arg Glu Gly His Leu Pro Ser Ile Leu
        355                 360                 365

Ser Met Ile His Pro Gln Leu Leu Thr Pro Val Pro Ser Leu Val Phe
    370                 375                 380

Thr Cys Val Met Thr Leu Met Tyr Ala Phe Ser Arg Asp Ile Phe Ser
385                 390                 395                 400

Ile Ile Asn Phe Phe Ser Phe Phe Asn Trp Leu Cys Val Ala Leu Ala
                405                 410                 415

Ile Ile Gly Met Met Trp Leu Arg Phe Lys Lys Pro Glu Leu Glu Arg
            420                 425                 430

Pro Ile Lys Val Asn Leu Ala Leu Pro Val Phe Phe Ile Leu Ala Cys
        435                 440                 445

Leu Phe Leu Ile Ala Val Ser Phe Trp Lys Thr Pro Leu Glu Cys Gly
    450                 455                 460

Ile Gly Phe Ala Ile Ile Leu Ser Gly Leu Pro Val Tyr Phe Phe Gly
465                 470                 475                 480

Val Trp Trp Lys Asn Lys Pro Lys Trp Ile Leu Gln Val Ile Phe Ser
                485                 490                 495

Val Thr Val Leu Cys Gln Lys Leu Met Gln Val Val Pro Gln Glu Thr
            500                 505                 510

<210> SEQ ID NO 5
<211> LENGTH: 1863
<212> TYPE: DNA
<213> ORGANISM: Homo sapiens
<220> FEATURE:
<221> NAME/KEY: 5'UTR
<222> LOCATION: (1)..(109)
<220> FEATURE:
<221> NAME/KEY: CDS
<222> LOCATION: (110)..(1699)
<220> FEATURE:
<221> NAME/KEY: 3'UTR
<222> LOCATION: (1700)..(1863)

<400> SEQUENCE: 5
gcgcggagcc acagaggccg gggagagcgt tctgggtccg agggtccagg tagggggttga      60 gccaccatct gaccgcaagc tgcgtcgtgt cgccggttct gcaggcacc atg agc cag     118
                                                      Met Ser Gln
                                                        1 gac acc gag gtg gat atg aag gag gtg gag ctg aat gag tta gag ccc       166
Asp Thr Glu Val Asp Met Lys Glu Val Glu Leu Asn Glu Leu Glu Pro
      5                  10                  15 gag aag cag ccg atg aac gcg gcg tct ggg gcg gcc atg tcc ctg gcg       214
Glu Lys Gln Pro Met Asn Ala Ala Ser Gly Ala Ala Met Ser Leu Ala
 20                  25                  30                  35 gga gcc gag aag aat ggt ctg gtg aag atc aag gtg gcg gaa gac gag       262
Gly Ala Glu Lys Asn Gly Leu Val Lys Ile Lys Val Ala Glu Asp Glu
                 40                  45                  50
```

-continued

```
gcg gag gcg gca gcc gcg gct aag ttc acg ggc ctg tcc aag gag gag        310
Ala Glu Ala Ala Ala Ala Ala Lys Phe Thr Gly Leu Ser Lys Glu Glu
            55                  60                  65 ctg ctg aag gtg gca ggc agc ccc ggc tgg gta cgc acc cgc tgg gca        358
Leu Leu Lys Val Ala Gly Ser Pro Gly Trp Val Arg Thr Arg Trp Ala
        70                  75                  80 ctg ctg ctg ctc ttc tgg ctc ggc tgg ctc ggc atg ctt gct ggt gcc        406
Leu Leu Leu Leu Phe Trp Leu Gly Trp Leu Gly Met Leu Ala Gly Ala
    85                  90                  95 gtg gtc ata atc gtg cga gcg ccg cgt tgt cgc gag cta ccg gcg cag        454
Val Val Ile Ile Val Arg Ala Pro Arg Cys Arg Glu Leu Pro Ala Gln
100                 105                 110                 115 aag tgg tgg cac acg ggc gcc ctc tac cgc atc ggc gac ctt cag gcc        502
Lys Trp Trp His Thr Gly Ala Leu Tyr Arg Ile Gly Asp Leu Gln Ala
                120                 125                 130 ttc cag ggc cac ggc gcg ggc aac ctg gcg ggt ctg aag ggg cgt ctc        550
Phe Gln Gly His Gly Ala Gly Asn Leu Ala Gly Leu Lys Gly Arg Leu
            135                 140                 145 gat tac ctg agc tct ctg aag gtg aag ggc ctt gtg ctg ggt cca att        598
Asp Tyr Leu Ser Ser Leu Lys Val Lys Gly Leu Val Leu Gly Pro Ile
        150                 155                 160 cac aag aac cag aag gat gat gtc gct cag act gac ttg ctg cag atc        646
His Lys Asn Gln Lys Asp Asp Val Ala Gln Thr Asp Leu Leu Gln Ile
    165                 170                 175 gac ccc aat ttt ggc tcc aag gaa gat ttt gac agt ctc ttg caa tcg        694
Asp Pro Asn Phe Gly Ser Lys Glu Asp Phe Asp Ser Leu Leu Gln Ser
180                 185                 190                 195 gct aaa aaa aag agc atc cgt gtc att ctg gac ctt act ccc aac tac        742
Ala Lys Lys Lys Ser Ile Arg Val Ile Leu Asp Leu Thr Pro Asn Tyr
                200                 205                 210 cgg ggt gag aac tcg tgg ttc tcc act cag gtt gac act gtg gcc acc        790
Arg Gly Glu Asn Ser Trp Phe Ser Thr Gln Val Asp Thr Val Ala Thr
            215                 220                 225 aag gtg aag gat gct ctg gag ttt tgg ctg caa gct ggc gtg gat ggg        838
Lys Val Lys Asp Ala Leu Glu Phe Trp Leu Gln Ala Gly Val Asp Gly
        230                 235                 240 ttc cag gtt cgg gac ata gag aat ctg aag gat gca tcc tca ttc ttg        886
Phe Gln Val Arg Asp Ile Glu Asn Leu Lys Asp Ala Ser Ser Phe Leu
    245                 250                 255 gct gag tgg caa aat atc acc aag ggc ttc agt gaa gac agg ctc ttg        934
Ala Glu Trp Gln Asn Ile Thr Lys Gly Phe Ser Glu Asp Arg Leu Leu
260                 265                 270                 275 att gcg ggg act aac tcc tcc gac ctt cag cag atc ctg agc cta ctc        982
Ile Ala Gly Thr Asn Ser Ser Asp Leu Gln Gln Ile Leu Ser Leu Leu
                280                 285                 290 gaa tcc aac aaa gac ttg ctg ttg act agc tca tac ctg tct gat tct       1030
Glu Ser Asn Lys Asp Leu Leu Leu Thr Ser Ser Tyr Leu Ser Asp Ser
            295                 300                 305 ggt tct act ggg gag cat aca aaa tcc cta gtc aca cag tat ttg aat       1078
Gly Ser Thr Gly Glu His Thr Lys Ser Leu Val Thr Gln Tyr Leu Asn
        310                 315                 320 gcc act ggc aat cgc tgg tgc agc tgg agt ttg tct cag gca agg ctc       1126
Ala Thr Gly Asn Arg Trp Cys Ser Trp Ser Leu Ser Gln Ala Arg Leu
    325                 330                 335 ctg act tcc ttc ttg ccg gct caa ctt ctc cga ctc tac cag ctg atg       1174
Leu Thr Ser Phe Leu Pro Ala Gln Leu Leu Arg Leu Tyr Gln Leu Met
340                 345                 350                 355 ctc ttc acc ctg cca ggg acc cct gtt ttc agc tac ggg gat gag att       1222
Leu Phe Thr Leu Pro Gly Thr Pro Val Phe Ser Tyr Gly Asp Glu Ile
                360                 365                 370
```

```
ggc ctg gat gca gct gcc ctt cct gga cag cct atg gag gct cca gtc      1270
Gly Leu Asp Ala Ala Ala Leu Pro Gly Gln Pro Met Glu Ala Pro Val
            375                 380                 385 atg ctg tgg gat gag tcc agc ttc cct gac atc cca ggg gct gta agt      1318
Met Leu Trp Asp Glu Ser Ser Phe Pro Asp Ile Pro Gly Ala Val Ser
        390                 395                 400 gcc aac atg act gtg aag ggc cag agt gaa gac cct ggc tcc ctc ctt      1366
Ala Asn Met Thr Val Lys Gly Gln Ser Glu Asp Pro Gly Ser Leu Leu
405                 410                 415 tcc ttg ttc cgg cgg ctg agt gac cag cgg agt aag gag cgc tcc cta      1414
Ser Leu Phe Arg Arg Leu Ser Asp Gln Arg Ser Lys Glu Arg Ser Leu
420                 425                 430                 435 ctg cat ggg gac ttc cac gcg ttc tcc gct ggg cct gga ctc ttc tcc      1462
Leu His Gly Asp Phe His Ala Phe Ser Ala Gly Pro Gly Leu Phe Ser
                440                 445                 450 tat atc cgc cac tgg gac cag aat gag cgt ttt ctg gta gtg ctt aac      1510
Tyr Ile Arg His Trp Asp Gln Asn Glu Arg Phe Leu Val Val Leu Asn
            455                 460                 465 ttt ggg gat gtg ggc ctc tcg gct gga ctg cag gcc tcc gac ctg cct      1558
Phe Gly Asp Val Gly Leu Ser Ala Gly Leu Gln Ala Ser Asp Leu Pro
        470                 475                 480 gcc agc gcc agc ctc cca gcc aag gct gac ctc ctg ctc agc acc cag      1606
Ala Ser Ala Ser Leu Pro Ala Lys Ala Asp Leu Leu Leu Ser Thr Gln
485                 490                 495 cca ggc cgt gag gag ggc tcc cct ctt gag ctg gaa cgc ctg aaa ctg      1654
Pro Gly Arg Glu Glu Gly Ser Pro Leu Glu Leu Glu Arg Leu Lys Leu
500                 505                 510                 515 gag cct cac gaa ggg ctg ctg ctc cgc ttc ccc tac gcg gcc tga          1699
Glu Pro His Glu Gly Leu Leu Leu Arg Phe Pro Tyr Ala Ala
                520                 525                 530 cttcagcctg acatggaccc actacccttc tcctttcctt cccaggccct tggttctga    1759 tttttctctt ttttaaaaac aaacaaacaa actgttgcag attatgagtg aaccccaaa    1819 tagggtgttt tctgccttca ataaaagtc accccctgcat ggtg                    1863

<210> SEQ ID NO 6
<211> LENGTH: 529
<212> TYPE: PRT
<213> ORGANISM: Homo sapiens

<400> SEQUENCE: 6

Met Ser Gln Asp Thr Glu Val Asp Met Lys Glu Val Glu Leu Asn Glu
1               5                   10                  15

Leu Glu Pro Glu Lys Gln Pro Met Asn Ala Ala Ser Gly Ala Ala Met
            20                  25                  30

Ser Leu Ala Gly Ala Glu Lys Asn Gly Leu Val Lys Ile Lys Val Ala
        35                  40                  45

Glu Asp Glu Ala Glu Ala Ala Ala Ala Lys Phe Thr Gly Leu Ser
    50                  55                  60

Lys Glu Glu Leu Leu Lys Val Ala Gly Ser Pro Gly Trp Val Arg Thr
65                  70                  75                  80

Arg Trp Ala Leu Leu Leu Leu Phe Trp Leu Gly Trp Leu Gly Met Leu
                85                  90                  95

Ala Gly Ala Val Val Ile Ile Val Arg Ala Pro Arg Cys Arg Glu Leu
            100                 105                 110

Pro Ala Gln Lys Trp Trp His Thr Gly Ala Leu Tyr Arg Ile Gly Asp
        115                 120                 125
```

-continued

```
Leu Gln Ala Phe Gln Gly His Gly Ala Gly Asn Leu Ala Gly Leu Lys
    130                 135                 140
Gly Arg Leu Asp Tyr Leu Ser Ser Leu Lys Val Lys Gly Leu Val Leu
145                 150                 155                 160
Gly Pro Ile His Lys Asn Gln Lys Asp Val Ala Gln Thr Asp Leu
                165                 170                 175
Leu Gln Ile Asp Pro Asn Phe Gly Ser Lys Glu Asp Phe Asp Ser Leu
            180                 185                 190
Leu Gln Ser Ala Lys Lys Lys Ser Ile Arg Val Ile Leu Asp Leu Thr
            195                 200                 205
Pro Asn Tyr Arg Gly Glu Asn Ser Trp Phe Ser Thr Gln Val Asp Thr
210                 215                 220
Val Ala Thr Lys Val Lys Asp Ala Leu Glu Phe Trp Leu Gln Ala Gly
225                 230                 235                 240
Val Asp Gly Phe Gln Val Arg Asp Ile Glu Asn Leu Lys Asp Ala Ser
                245                 250                 255
Ser Phe Leu Ala Glu Trp Gln Asn Ile Thr Lys Gly Phe Ser Glu Asp
            260                 265                 270
Arg Leu Leu Ile Ala Gly Thr Asn Ser Ser Asp Leu Gln Gln Ile Leu
            275                 280                 285
Ser Leu Leu Glu Ser Asn Lys Asp Leu Leu Leu Thr Ser Ser Tyr Leu
290                 295                 300
Ser Asp Ser Gly Ser Thr Gly Glu His Thr Lys Ser Leu Val Thr Gln
305                 310                 315                 320
Tyr Leu Asn Ala Thr Gly Asn Arg Trp Cys Ser Trp Ser Leu Ser Gln
                325                 330                 335
Ala Arg Leu Leu Thr Ser Phe Leu Pro Ala Gln Leu Leu Arg Leu Tyr
            340                 345                 350
Gln Leu Met Leu Phe Thr Leu Pro Gly Thr Pro Val Phe Ser Tyr Gly
            355                 360                 365
Asp Glu Ile Gly Leu Asp Ala Ala Leu Pro Gly Gln Pro Met Glu
370                 375                 380
Ala Pro Val Met Leu Trp Asp Glu Ser Ser Phe Pro Asp Ile Pro Gly
385                 390                 395                 400
Ala Val Ser Ala Asn Met Thr Val Lys Gly Gln Ser Glu Asp Pro Gly
                405                 410                 415
Ser Leu Leu Ser Leu Phe Arg Arg Leu Ser Asp Gln Arg Ser Lys Glu
            420                 425                 430
Arg Ser Leu Leu His Gly Asp Phe His Ala Phe Ser Ala Gly Pro Gly
            435                 440                 445
Leu Phe Ser Tyr Ile Arg His Trp Asp Gln Asn Glu Arg Phe Leu Val
450                 455                 460
Val Leu Asn Phe Gly Asp Val Gly Leu Ser Ala Gly Leu Gln Ala Ser
465                 470                 475                 480
Asp Leu Pro Ala Ser Ala Ser Leu Pro Ala Lys Ala Asp Leu Leu Leu
                485                 490                 495
Ser Thr Gln Pro Gly Arg Glu Glu Gly Ser Pro Leu Glu Leu Glu Arg
            500                 505                 510
Leu Lys Leu Glu Pro His Glu Gly Leu Leu Leu Arg Phe Pro Tyr Ala
            515                 520                 525
Ala
```

```
<210> SEQ ID NO 7
<211> LENGTH: 1797
<212> TYPE: DNA
<213> ORGANISM: Rat
<220> FEATURE:
<221> NAME/KEY: 5'UTR
<222> LOCATION: (1)..(19)
<220> FEATURE:
<221> NAME/KEY: CDS
<222> LOCATION: (20)..(1603)
<220> FEATURE:
<221> NAME/KEY: 3'UTR
<222> LOCATION: (1604)..(1797)

<400> SEQUENCE: 7
cgttgctgtc gcaggtacc atg agc cag gac acc gaa gtg gac atg aaa gat       52
                    Met Ser Gln Asp Thr Glu Val Asp Met Lys Asp
                     1               5                  10 gtg gag ctg aac gag ctg gaa ccg gag aag cag cct atg aat gca gcg       100
Val Glu Leu Asn Glu Leu Glu Pro Glu Lys Gln Pro Met Asn Ala Ala
         15                  20                  25 gac ggg gcg gca gcc ggg gag aag aac ggt ctg gtg aag att aag gtg       148
Asp Gly Ala Ala Ala Gly Glu Lys Asn Gly Leu Val Lys Ile Lys Val
     30                  35                  40 gcc gaa gac gag gcg gaa gcc ggg gtc aag ttc aca ggc tta tcc aag       196
Ala Glu Asp Glu Ala Glu Ala Gly Val Lys Phe Thr Gly Leu Ser Lys
 45                  50                  55 gag gag cta ttg aag gta gct ggc agc ccg ggc tgg gtg cgc acc cgc       244
Glu Glu Leu Leu Lys Val Ala Gly Ser Pro Gly Trp Val Arg Thr Arg
 60                  65                  70                  75 tgg gcg ctg ctg ctg ctc ttc tgg ctc ggt tgg ctg ggt atg ctg gcg       292
Trp Ala Leu Leu Leu Leu Phe Trp Leu Gly Trp Leu Gly Met Leu Ala
                 80                  85                  90 ggc gcc gtg gtt atc atc gtt cgg gcg cca cgc tgc cgt gag ctg ccg       340
Gly Ala Val Val Ile Ile Val Arg Ala Pro Arg Cys Arg Glu Leu Pro
             95                 100                 105 gta cag aga tgg tgg cac aag ggc gcc ctc tac cgc atc ggc gac ctt       388
Val Gln Arg Trp Trp His Lys Gly Ala Leu Tyr Arg Ile Gly Asp Leu
        110                 115                 120 cag gcc ttc gta ggc ccg gaa gcg aga ggc ata gct ggt ctg aag aac       436
Gln Ala Phe Val Gly Pro Glu Ala Arg Gly Ile Ala Gly Leu Lys Asn
    125                 130                 135 cat ctg gag tac ttg agc acc ctg aag gtg aag ggc cta gtt ttg ggc       484
His Leu Glu Tyr Leu Ser Thr Leu Lys Val Lys Gly Leu Val Leu Gly
140                 145                 150                 155 cca att cac aag aac cag aag gat gaa gtc aat gaa acc gac ttg aaa       532
Pro Ile His Lys Asn Gln Lys Asp Glu Val Asn Glu Thr Asp Leu Lys
                160                 165                 170 cag att gat ccc gat tta ggc tcc cag gaa gat ttt aaa gac ctt cta       580
Gln Ile Asp Pro Asp Leu Gly Ser Gln Glu Asp Phe Lys Asp Leu Leu
            175                 180                 185 caa agt gcc aag aaa aag agc att cac atc att ttg gac ctc act ccc       628
Gln Ser Ala Lys Lys Lys Ser Ile His Ile Ile Leu Asp Leu Thr Pro
        190                 195                 200 aac tat aag ggc cag aat gca tgg ttc ctc cct cct cag gct gac att       676
Asn Tyr Lys Gly Gln Asn Ala Trp Phe Leu Pro Pro Gln Ala Asp Ile
    205                 210                 215 gta gcc acc aaa atg aag gag gct ctg agt tct tgg ttg cag gac ggt       724
Val Ala Thr Lys Met Lys Glu Ala Leu Ser Ser Trp Leu Gln Asp Gly
220                 225                 230                 235 gtg gat ggg ttc caa gtt cgg gat gtg gga aag ctg gcg aat gca tcc       772
Val Asp Gly Phe Gln Val Arg Asp Val Gly Lys Leu Ala Asn Ala Ser
                240                 245                 250
```

```
ttg tac ttg gct gag tgg cag aat atc acc aag aac ttc agt gag gac        820
Leu Tyr Leu Ala Glu Trp Gln Asn Ile Thr Lys Asn Phe Ser Glu Asp
            255                 260                 265 agg ctt ttg att gca ggg acc gcg tcc tct gac ctg caa caa att gtc        868
Arg Leu Leu Ile Ala Gly Thr Ala Ser Ser Asp Leu Gln Gln Ile Val
        270                 275                 280 aac ata ctt gaa tcc acc agc gat ctg ctg ctg acc agc tca tac ctg        916
Asn Ile Leu Glu Ser Thr Ser Asp Leu Leu Leu Thr Ser Ser Tyr Leu
    285                 290                 295 tca cag ccc gtt ttc act ggg gag cat gca gaa ctc cta gtg att aag        964
Ser Gln Pro Val Phe Thr Gly Glu His Ala Glu Leu Leu Val Ile Lys
300                 305                 310                 315 tat ttg aat gcc act ggc agc cgc tgg tgc agc tgg agt gtg tcg cag       1012
Tyr Leu Asn Ala Thr Gly Ser Arg Trp Cys Ser Trp Ser Val Ser Gln
            320                 325                 330 gca gga ctc ctg aca tcc ttt ata ccg gct cag ttt ctc cga ctc tac       1060
Ala Gly Leu Leu Thr Ser Phe Ile Pro Ala Gln Phe Leu Arg Leu Tyr
        335                 340                 345 cag ctg ctg ctc ttc act ctg cca gga act cct gtt ttc agc tat ggg       1108
Gln Leu Leu Leu Phe Thr Leu Pro Gly Thr Pro Val Phe Ser Tyr Gly
    350                 355                 360 gat gag ctt ggc ctt cag gca gtt gcc ctt cct gga cag cct atg gag       1156
Asp Glu Leu Gly Leu Gln Ala Val Ala Leu Pro Gly Gln Pro Met Glu
365                 370                 375 gct cca ttc atg ctg tgg aat gag tct agc aac tcc caa acc tca agt       1204
Ala Pro Phe Met Leu Trp Asn Glu Ser Ser Asn Ser Gln Thr Ser Ser
            380                 385                 390                 395 cct gta agc ctc aac atg aca gtg aag ggc caa aat gaa gac ccc ggc       1252
Pro Val Ser Leu Asn Met Thr Val Lys Gly Gln Asn Glu Asp Pro Gly
        400                 405                 410 tcc ctc ctc acc cag ttc cgg cga ctg agt gac ctc cgt ggt aag gag       1300
Ser Leu Leu Thr Gln Phe Arg Arg Leu Ser Asp Leu Arg Gly Lys Glu
    415                 420                 425 cgc tct ctg tta cac ggt gac ttt gat gca ctg tct tcc tca tct ggg       1348
Arg Ser Leu Leu His Gly Asp Phe Asp Ala Leu Ser Ser Ser Ser Gly
        430                 435                 440 ctc ttc tcc tac gtc cgc cac tgg gac cag aat gag cgt tac ctg gtg       1396
Leu Phe Ser Tyr Val Arg His Trp Asp Gln Asn Glu Arg Tyr Leu Val
    445                 450                 455 gtg ctc aac ttc cag gat gtg ggc ctg tca gcc agg gta gga gcc tcc       1444
Val Leu Asn Phe Gln Asp Val Gly Leu Ser Ala Arg Val Gly Ala Ser
460                 465                 470                 475 aac ctc cct gct ggc ata agc ctg cca gcc agt gct aac ctt ttg ctt       1492
Asn Leu Pro Ala Gly Ile Ser Leu Pro Ala Ser Ala Asn Leu Leu Leu
            480                 485                 490 agt act gac agc acc cgg cta agc cgt gag gag ggc acc tcc ctg agc       1540
Ser Thr Asp Ser Thr Arg Leu Ser Arg Glu Glu Gly Thr Ser Leu Ser
        495                 500                 505 ctg gaa aac ctg agc ctg aat cct tat gag ggc ttg ttg tta cag ttc       1588
Leu Glu Asn Leu Ser Leu Asn Pro Tyr Glu Gly Leu Leu Leu Gln Phe
    510                 515                 520 cct ttt gtg gcc tga tccctctaca cagaacctgc caccttctt tcctctctca       1643
Pro Phe Val Ala
    525 ggcctttgga attctggtct ttctctcctt attttgtttt tgtttttaaa cttttgcaga   1703 ttacatatga attcttacac tgggggtttt tgttttcaaa ataaaaaaaa tcaccccctaa  1763 aaaaaaaaaa aaaaaaaaaa aaaaaaaaaa aaaa                              1797
```

<210> SEQ ID NO 8
<211> LENGTH: 527
<212> TYPE: PRT
<213> ORGANISM: Rat

<400> SEQUENCE: 8

| | | | | | | | | | | | | | | | |
|---|---|---|---|---|---|---|---|---|---|---|---|---|---|---|---|
| Met | Ser | Gln | Asp | Thr | Glu | Val | Asp | Met | Lys | Asp | Val | Glu | Leu | Asn | Glu |
| 1 | | | | 5 | | | | | 10 | | | | | 15 | |
| Leu | Glu | Pro | Glu | Lys | Gln | Pro | Met | Asn | Ala | Ala | Asp | Gly | Ala | Ala | Ala |
| | | | 20 | | | | | 25 | | | | | 30 | | |
| Gly | Glu | Lys | Asn | Gly | Leu | Val | Lys | Ile | Lys | Val | Ala | Glu | Asp | Glu | Ala |
| | | 35 | | | | | 40 | | | | | 45 | | | |
| Glu | Ala | Gly | Val | Lys | Phe | Thr | Gly | Leu | Ser | Lys | Glu | Glu | Leu | Leu | Lys |
| | 50 | | | | | 55 | | | | | 60 | | | | |
| Val | Ala | Gly | Ser | Pro | Gly | Trp | Val | Arg | Thr | Arg | Trp | Ala | Leu | Leu | Leu |
| 65 | | | | | 70 | | | | | 75 | | | | | 80 |
| Leu | Phe | Trp | Leu | Gly | Trp | Leu | Gly | Met | Leu | Ala | Gly | Ala | Val | Val | Ile |
| | | | | 85 | | | | | 90 | | | | | 95 | |
| Ile | Val | Arg | Ala | Pro | Arg | Cys | Arg | Glu | Leu | Pro | Val | Gln | Arg | Trp | Trp |
| | | | 100 | | | | | 105 | | | | | 110 | | |
| His | Lys | Gly | Ala | Leu | Tyr | Arg | Ile | Gly | Asp | Leu | Gln | Ala | Phe | Val | Gly |
| | | 115 | | | | | 120 | | | | | 125 | | | |
| Pro | Glu | Ala | Arg | Gly | Ile | Ala | Gly | Leu | Lys | Asn | His | Leu | Glu | Tyr | Leu |
| | 130 | | | | | 135 | | | | | 140 | | | | |
| Ser | Thr | Leu | Lys | Val | Lys | Gly | Leu | Val | Leu | Gly | Pro | Ile | His | Lys | Asn |
| 145 | | | | | 150 | | | | | 155 | | | | | 160 |
| Gln | Lys | Asp | Glu | Val | Asn | Glu | Thr | Asp | Leu | Lys | Gln | Ile | Asp | Pro | Asp |
| | | | | 165 | | | | | 170 | | | | | 175 | |
| Leu | Gly | Ser | Gln | Glu | Asp | Phe | Lys | Asp | Leu | Leu | Gln | Ser | Ala | Lys | Lys |
| | | | 180 | | | | | 185 | | | | | 190 | | |
| Lys | Ser | Ile | His | Ile | Ile | Leu | Asp | Leu | Thr | Pro | Asn | Tyr | Lys | Gly | Gln |
| | | 195 | | | | | 200 | | | | | 205 | | | |
| Asn | Ala | Trp | Phe | Leu | Pro | Pro | Gln | Ala | Asp | Ile | Val | Ala | Thr | Lys | Met |
| | 210 | | | | | 215 | | | | | 220 | | | | |
| Lys | Glu | Ala | Leu | Ser | Ser | Trp | Leu | Gln | Asp | Gly | Val | Asp | Gly | Phe | Gln |
| 225 | | | | | 230 | | | | | 235 | | | | | 240 |
| Val | Arg | Asp | Val | Gly | Lys | Leu | Ala | Asn | Ala | Ser | Leu | Tyr | Leu | Ala | Glu |
| | | | | 245 | | | | | 250 | | | | | 255 | |
| Trp | Gln | Asn | Ile | Thr | Lys | Asn | Phe | Ser | Glu | Asp | Arg | Leu | Leu | Ile | Ala |
| | | | 260 | | | | | 265 | | | | | 270 | | |
| Gly | Thr | Ala | Ser | Ser | Asp | Leu | Gln | Gln | Ile | Val | Asn | Ile | Leu | Glu | Ser |
| | | 275 | | | | | 280 | | | | | 285 | | | |
| Thr | Ser | Asp | Leu | Leu | Leu | Thr | Ser | Ser | Tyr | Leu | Ser | Gln | Pro | Val | Phe |
| | 290 | | | | | 295 | | | | | 300 | | | | |
| Thr | Gly | Glu | His | Ala | Glu | Leu | Leu | Val | Ile | Lys | Tyr | Leu | Asn | Ala | Thr |
| 305 | | | | | 310 | | | | | 315 | | | | | 320 |
| Gly | Ser | Arg | Trp | Cys | Ser | Trp | Ser | Val | Ser | Gln | Ala | Gly | Leu | Leu | Thr |
| | | | | 325 | | | | | 330 | | | | | 335 | |
| Ser | Phe | Ile | Pro | Ala | Gln | Phe | Leu | Arg | Leu | Tyr | Gln | Leu | Leu | Leu | Phe |
| | | | 340 | | | | | 345 | | | | | 350 | | |
| Thr | Leu | Pro | Gly | Thr | Pro | Val | Phe | Ser | Tyr | Gly | Asp | Glu | Leu | Gly | Leu |
| | | 355 | | | | | 360 | | | | | 365 | | | |
| Gln | Ala | Val | Ala | Leu | Pro | Gly | Gln | Pro | Met | Glu | Ala | Pro | Phe | Met | Leu |
| | 370 | | | | | 375 | | | | | 380 | | | | |

-continued

```
Trp Asn Glu Ser Ser Asn Ser Gln Thr Ser Ser Pro Val Ser Leu Asn
385                 390                 395                 400

Met Thr Val Lys Gly Gln Asn Glu Asp Pro Gly Ser Leu Leu Thr Gln
            405                 410                 415

Phe Arg Arg Leu Ser Asp Leu Arg Gly Lys Glu Arg Ser Leu Leu His
        420                 425                 430

Gly Asp Phe Asp Ala Leu Ser Ser Ser Ser Gly Leu Phe Ser Tyr Val
    435                 440                 445

Arg His Trp Asp Gln Asn Glu Arg Tyr Leu Val Val Leu Asn Phe Gln
450                 455                 460

Asp Val Gly Leu Ser Ala Arg Val Gly Ala Ser Asn Leu Pro Ala Gly
465                 470                 475                 480

Ile Ser Leu Pro Ala Ser Ala Asn Leu Leu Ser Thr Asp Ser Thr
                485                 490                 495

Arg Leu Ser Arg Glu Glu Gly Thr Ser Leu Ser Leu Glu Asn Leu Ser
            500                 505                 510

Leu Asn Pro Tyr Glu Gly Leu Leu Leu Gln Phe Pro Phe Val Ala
        515                 520                 525

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence:Artificially
      synthesized primer sequence
<220> FEATURE:
<221> NAME/KEY: primer_bind
<222> LOCATION: (1)..(22)

<400> SEQUENCE: 9
cgaagtggac atgaaagatg tg                                              22

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence:Artificially
      synthesized primer sequence
<220> FEATURE:
<221> NAME/KEY: primer_bind
<222> LOCATION: (1)..(22)

<400> SEQUENCE: 10
aaactaggcc cttcaccttc ag                                              22

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence:Artificially
      synthesized primer sequence
<220> FEATURE:
<221> NAME/KEY: primer_bind
<222> LOCATION: (1)..(24)

<400> SEQUENCE: 11
actgctgctg ctcttctggc tcgg                                            24
```

```
<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence:Artificially
      synthesized primer sequence
<220> FEATURE:
<221> NAME/KEY: primer_bind
<222> LOCATION: (1)..(24)

<400> SEQUENCE: 12
gtggatgggt tccaggttcg ggac                                          24

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence:Artificially
      synthesized primer sequence
<220> FEATURE:
<221> NAME/KEY: primer_bind
<222> LOCATION: (1)..(24)

<400> SEQUENCE: 13
tgctgtggga tgagtccagc ttcc                                          24

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence:Artificially
      synthesized primer sequence
<220> FEATURE:
<221> NAME/KEY: primer_bind
<222> LOCATION: (1)..(24)

<400> SEQUENCE: 14
gcaggaggtc agccttggct ggca                                          24

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence:Artificially
      synthesized primer sequence
<220> FEATURE:
<221> NAME/KEY: primer_bind
<222> LOCATION: (1)..(24)

<400> SEQUENCE: 15
cttgcctgag acaaactcca gctg                                          24

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence:Artificially
      synthesized primer sequence
<220> FEATURE:
<221> NAME/KEY: primer_bind
<222> LOCATION: (1)..(24)

<400> SEQUENCE: 16
actgtcaaaa tcttccttgg agcc                                          24
```

```
<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence:Artificially
      synthesized primer sequence
<220> FEATURE:
<221> NAME/KEY: primer_bind
<222> LOCATION: (1)..(24)

<400> SEQUENCE: 17
ttctcgggct ctaactcatt cagc                                              24

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence:Artificially
      synthesized primer sequence
<220> FEATURE:
<221> NAME/KEY: primer_bind
<222> LOCATION: (1)..(23)

<400> SEQUENCE: 18
tgctgctgct cacggccgtg aac                                               23

<210> SEQ ID NO 19
<211> LENGTH: 17
<212> TYPE: DNA
<213> ORGANISM: Artificial Sequence
<220> FEATURE:
<223> OTHER INFORMATION: Description of Artificial Sequence:Artificially
      synthesized primer sequence
<220> FEATURE:
<221> NAME/KEY: primer_bind
<222> LOCATION: (1)..(17)

<400> SEQUENCE: 19
tggcggcctt cacgctg                                                      17

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence:Artificially
      synthesized primer sequence
<220> FEATURE:
<221> NAME/KEY: primer_bind
<222> LOCATION: (1)..(25)

<400> SEQUENCE: 20
atctagattg gacacatcac ccttc                                             25

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence:Artificially
      synthesized primer sequence
<220> FEATURE:
<221> NAME/KEY: primer_bind
<222> LOCATION: (1)..(22)

<400> SEQUENCE: 21
gtggtgaagt aggccaggtt gg                                                22
```

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence:Artificially
      synthesized primer sequence
<220> FEATURE:
<221> NAME/KEY: primer_bind
<222> LOCATION: (1)..(21)

<400> SEQUENCE: 22
gtggggtccc gggaaggcca c                                              21

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence:Artificially
      synthesized primer sequence
<220> FEATURE:
<221> NAME/KEY: primer_bind
<222> LOCATION: (1)..(22)

<400> SEQUENCE: 23 cttgttttc caccagaccc cg                                              22

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence:Artificially
      synthesized primer sequence
<220> FEATURE:
<221> NAME/KEY: primer_bind
<222> LOCATION: (1)..(22)

<400> SEQUENCE: 24
tgagggatga gattcgtacc ag                                             22

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence:Artificially
      synthesized primer sequence
<220> FEATURE:
<221> NAME/KEY: primer_bind
<222> LOCATION: (1)..(23)

<400> SEQUENCE: 25
cctgggagga atcacccacc ttg                                            23

<210> SEQ ID NO 26
<211> LENGTH: 1524
<212> TYPE: RNA
<213> ORGANISM: Homo sapiens
<220> FEATURE:
<221> NAME/KEY: CDS
<222> LOCATION: (1)..(1524)

<400> SEQUENCE: 26 aug gcg ggu gcg ggc ccg aag cgg cgc gcg cua gcg gcg ccg gcg gcc      48
Met Ala Gly Ala Gly Pro Lys Arg Arg Ala Leu Ala Ala Pro Ala Ala
 1               5                  10                  15

-continued

| | | | | | | | | | | | | | | | | |
|---|---|---|---|---|---|---|---|---|---|---|---|---|---|---|---|---|
| gag | gag | aag | gaa | gag | gcg | cgg | gag | aag | aug | cug | gcc | gcc | aag | agc | gcg | 96 |
| Glu | Glu | Lys | Glu | Glu | Ala | Arg | Glu | Lys | Met | Leu | Ala | Ala | Lys | Ser | Ala | |
| | | | 20 | | | | | 25 | | | | | 30 | | | |

| | | | | | | | | | | | | | | | | |
|---|---|---|---|---|---|---|---|---|---|---|---|---|---|---|---|---|
| gac | ggc | ucg | gcg | ccg | gca | ggc | gag | ggc | gag | ggc | gug | acc | cug | cag | cgg | 144 |
| Asp | Gly | Ser | Ala | Pro | Ala | Gly | Glu | Gly | Glu | Gly | Val | Thr | Leu | Gln | Arg | |
| | | 35 | | | | | 40 | | | | | 45 | | | | |

| | | | | | | | | | | | | | | | | |
|---|---|---|---|---|---|---|---|---|---|---|---|---|---|---|---|---|
| aac | auc | acg | cug | cuc | aac | ggu | gcc | auc | auc | gug | ggg | acc | auu | auc | | 192 |
| Asn | Ile | Thr | Leu | Leu | Asn | Gly | Val | Ala | Ile | Ile | Val | Gly | Thr | Ile | Ile | |
| | 50 | | | | | 55 | | | | | 60 | | | | | |

| | | | | | | | | | | | | | | | | |
|---|---|---|---|---|---|---|---|---|---|---|---|---|---|---|---|---|
| ggc | ucg | ggc | auc | uuc | gug | acg | ccc | acg | ggc | gug | cuc | aag | gag | gca | ggc | 240 |
| Gly | Ser | Gly | Ile | Phe | Val | Thr | Pro | Thr | Gly | Val | Leu | Lys | Glu | Ala | Gly | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| ucg | ccg | ggg | cug | gcg | cug | gug | gug | ugg | gcc | gcg | ugc | ggc | guc | uuc | ucc | 288 |
| Ser | Pro | Gly | Leu | Ala | Leu | Val | Val | Trp | Ala | Ala | Cys | Gly | Val | Phe | Ser | |
| | | | | 85 | | | | | 90 | | | | | 95 | | |

| | | | | | | | | | | | | | | | | |
|---|---|---|---|---|---|---|---|---|---|---|---|---|---|---|---|---|
| auc | gug | ggc | gcg | cuc | ugc | uac | gcg | gag | cuc | ggc | acc | acc | auc | ucc | aaa | 336 |
| Ile | Val | Gly | Ala | Leu | Cys | Tyr | Ala | Glu | Leu | Gly | Thr | Thr | Ile | Ser | Lys | |
| | | | 100 | | | | | 105 | | | | | 110 | | | |

| | | | | | | | | | | | | | | | | |
|---|---|---|---|---|---|---|---|---|---|---|---|---|---|---|---|---|
| ucg | ggc | ggc | gac | uac | gcc | uac | aug | cug | gag | guc | uac | ggc | ucg | cug | ccc | 384 |
| Ser | Gly | Gly | Asp | Tyr | Ala | Tyr | Met | Leu | Glu | Val | Tyr | Gly | Ser | Leu | Pro | |
| | | 115 | | | | | 120 | | | | | 125 | | | | |

| | | | | | | | | | | | | | | | | |
|---|---|---|---|---|---|---|---|---|---|---|---|---|---|---|---|---|
| gcc | uuc | cuc | aag | cuc | ugg | auc | gag | cug | cuc | auc | auc | cgg | ccu | uca | ucg | 432 |
| Ala | Phe | Leu | Lys | Leu | Trp | Ile | Glu | Leu | Leu | Ile | Ile | Arg | Pro | Ser | Ser | |
| | 130 | | | | | 135 | | | | | 140 | | | | | |

| | | | | | | | | | | | | | | | | |
|---|---|---|---|---|---|---|---|---|---|---|---|---|---|---|---|---|
| cag | uac | auc | gug | gcc | cug | guc | uuc | gcc | acc | uac | cug | cuc | aag | ccg | cuc | 480 |
| Gln | Tyr | Ile | Val | Ala | Leu | Val | Phe | Ala | Thr | Tyr | Leu | Leu | Lys | Pro | Leu | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| uuc | ccc | acc | ugc | ccg | gug | ccc | gag | gag | gca | gcc | aag | cuc | gug | gcc | ugc | 528 |
| Phe | Pro | Thr | Cys | Pro | Val | Pro | Glu | Glu | Ala | Ala | Lys | Leu | Val | Ala | Cys | |
| | | | | 165 | | | | | 170 | | | | | 175 | | |

| | | | | | | | | | | | | | | | | |
|---|---|---|---|---|---|---|---|---|---|---|---|---|---|---|---|---|
| cuc | ugc | gug | cug | cug | cuc | acg | gcc | gug | aac | ugc | uac | agc | gug | aag | gcc | 576 |
| Leu | Cys | Val | Leu | Leu | Leu | Thr | Ala | Val | Asn | Cys | Tyr | Ser | Val | Lys | Ala | |
| | | | 180 | | | | | 185 | | | | | 190 | | | |

| | | | | | | | | | | | | | | | | |
|---|---|---|---|---|---|---|---|---|---|---|---|---|---|---|---|---|
| gcc | acc | cgg | guc | cag | gau | gcc | uuu | gcc | gcc | gcc | aag | cuc | cug | gcc | cug | 624 |
| Ala | Thr | Arg | Val | Gln | Xaa | Ala | Phe | Ala | Ala | Ala | Lys | Leu | Leu | Ala | Leu | |
| | | 195 | | | | | 200 | | | | | 205 | | | | |

| | | | | | | | | | | | | | | | | |
|---|---|---|---|---|---|---|---|---|---|---|---|---|---|---|---|---|
| gcc | cug | auc | auc | cug | cug | ggc | uuc | guc | cag | auc | ggg | aag | ggu | gau | gug | 672 |
| Ala | Leu | Ile | Ile | Leu | Leu | Gly | Phe | Val | Gln | Ile | Gly | Lys | Gly | Xaa | Val | |
| | 210 | | | | | 215 | | | | | 220 | | | | | |

| | | | | | | | | | | | | | | | | |
|---|---|---|---|---|---|---|---|---|---|---|---|---|---|---|---|---|
| ucc | aau | cua | gau | ccc | aac | uuc | uca | uuu | gaa | ggc | acc | aaa | cug | gau | gug | 720 |
| Ser | Asn | Leu | Xaa | Pro | Asn | Phe | Ser | Phe | Glu | Gly | Thr | Lys | Leu | Xaa | Val | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| ggg | aac | auu | gug | cug | gca | uua | uac | agc | ggc | cuc | uuu | gcc | uau | gga | gga | 768 |
| Gly | Asn | Ile | Val | Leu | Ala | Leu | Tyr | Ser | Gly | Leu | Phe | Ala | Tyr | Gly | Gly | |
| | | | | 245 | | | | | 250 | | | | | 255 | | |

| | | | | | | | | | | | | | | | | |
|---|---|---|---|---|---|---|---|---|---|---|---|---|---|---|---|---|
| ugg | aau | uac | uug | aau | uuc | guc | aca | gag | gaa | aug | auc | aac | ccc | uac | aga | 816 |
| Trp | Asn | Tyr | Leu | Asn | Phe | Val | Thr | Glu | Glu | Met | Ile | Asn | Pro | Tyr | Arg | |
| | | | 260 | | | | | 265 | | | | | 270 | | | |

| | | | | | | | | | | | | | | | | |
|---|---|---|---|---|---|---|---|---|---|---|---|---|---|---|---|---|
| aac | cug | ccc | cug | gcc | auc | auc | auc | ucc | cug | ccc | auc | gug | acg | cug | gug | 864 |
| Asn | Leu | Pro | Leu | Ala | Ile | Ile | Ile | Ser | Leu | Pro | Ile | Val | Thr | Leu | Val | |
| | | 275 | | | | | 280 | | | | | 285 | | | | |

| | | | | | | | | | | | | | | | | |
|---|---|---|---|---|---|---|---|---|---|---|---|---|---|---|---|---|
| uac | gug | cug | acc | aac | cug | gcc | uac | uuc | acc | acc | cug | ucc | acc | gag | cag | 912 |
| Tyr | Val | Leu | Thr | Asn | Leu | Ala | Tyr | Phe | Thr | Thr | Leu | Ser | Thr | Glu | Gln | |
| | 290 | | | | | 295 | | | | | 300 | | | | | |

| | | | | | | | | | | | | | | | | |
|---|---|---|---|---|---|---|---|---|---|---|---|---|---|---|---|---|
| aug | cug | ucg | ucc | gag | gcc | gug | gcc | gug | gac | uuc | ggg | aac | uau | cac | cug | 960 |
| Met | Leu | Ser | Ser | Glu | Ala | Val | Ala | Val | Asp | Phe | Gly | Asn | Tyr | His | Leu | |
| 305 | | | | | 310 | | | | | 315 | | | | | 320 | |

| | | | | | | | | | | | | | | | | |
|---|---|---|---|---|---|---|---|---|---|---|---|---|---|---|---|---|
| ggc | guc | aug | ucc | ugg | auc | auc | ccc | guc | uuc | gug | ggc | cug | ucc | ugc | uuc | 1008 |
| Gly | Val | Met | Ser | Trp | Ile | Ile | Pro | Val | Phe | Val | Gly | Leu | Ser | Cys | Phe | |
| | | | 325 | | | | | 330 | | | | | 335 | | | |

```
ggc ucc guc aau ggg ucc cug uuc aca ucc ucc agg cuc uuc uuc gug      1056
Gly Ser Val Asn Gly Ser Leu Phe Thr Ser Ser Arg Leu Phe Phe Val
            340                 345                 350 ggg ucc cgg gaa ggc cac cug ccc ucc auc cuc ucc aug auc cac cca      1104
Gly Ser Arg Glu Gly His Leu Pro Ser Ile Leu Ser Met Ile His Pro
        355                 360                 365 cag cuc cuc acc ccc gug ccg ucc cuc gug uuc acg ugu gug aug acg      1152
Gln Leu Leu Thr Pro Val Pro Ser Leu Val Phe Thr Cys Val Met Thr
    370                 375                 380 cug cuc uac gcc uuc ucc aag gac auc uuc ucc guc auc aac uuc uuc      1200
Leu Leu Tyr Ala Phe Ser Lys Asp Ile Phe Ser Val Ile Asn Phe Phe
385                 390                 395                 400 agc uuc uuc aac ugg cuc ugc gug gcc cug gcc auc auc ggc aug auc      1248
Ser Phe Phe Asn Trp Leu Cys Val Ala Leu Ala Ile Ile Gly Met Ile
                405                 410                 415 ugg cug cgc cac aga aag ccu gag cuu gag cgg ccc auc aag gug aac      1296
Trp Leu Arg His Arg Lys Pro Glu Leu Glu Arg Pro Ile Lys Val Asn
            420                 425                 430 cug gcc cug ccu gug uuc uuc auc cug gcc ugc cuc uuc cug auc gcc      1344
Leu Ala Leu Pro Val Phe Phe Ile Leu Ala Cys Leu Phe Leu Ile Ala
        435                 440                 445 guc ucc uuc ugg aag aca ccc gug gag ugu ggc auc ggc uuc acc auc      1392
Val Ser Phe Trp Lys Thr Pro Val Glu Cys Gly Ile Gly Phe Thr Ile
    450                 455                 460 auc cuc agc ggg cug ccc guc uac uuc uuc ggg guc ugg ugg aaa aac      1440
Ile Leu Ser Gly Leu Pro Val Tyr Phe Phe Gly Val Trp Trp Lys Asn
465                 470                 475                 480 aag ccc aag ugg cuc cuc cag ggc auc uuc ucc acg guc cug ugu          1488
Lys Pro Lys Trp Leu Leu Gln Gly Ile Phe Ser Thr Val Leu Cys
                485                 490                 495 cag aag cuc aug cag gug guc ccc cag gag aca uag                      1524
Gln Lys Leu Met Gln Val Val Pro Gln Glu Thr
            500                 505

<210> SEQ ID NO 27
<211> LENGTH: 1590
<212> TYPE: RNA
<213> ORGANISM: Homo sapiens
<220> FEATURE:
<221> NAME/KEY: CDS
<222> LOCATION: (1)..(1590)

<400> SEQUENCE: 27 aug agc cag gac acc gag gug gau aug aag gag gug gag cug aau gag        48
Met Ser Gln Asp Thr Glu Val Xaa Met Lys Glu Val Glu Leu Asn Glu
1               5                   10                  15 uua gag ccc gag aag cag ccg aug aac gcg gcg ucu ggg gcg gcc aug        96
Leu Glu Pro Glu Lys Gln Pro Met Asn Ala Ala Ser Gly Ala Ala Met
                20                  25                  30 ucc cug gcg gga gcc gag aag aau ggu cug gug aag auc aag gug gcg      144
Ser Leu Ala Gly Ala Glu Lys Asn Gly Leu Val Lys Ile Lys Val Ala
            35                  40                  45 gaa gac gag gcg gag gcg gca gcc gcg gcu aag uuc acg ggc cug ucc      192
Glu Asp Glu Ala Glu Ala Ala Ala Ala Lys Phe Thr Gly Leu Ser
        50                  55                  60 aag gag gag cug cug aag gug gca ggc agc ccc ggc ugg gua cgc acc      240
Lys Glu Glu Leu Leu Lys Val Ala Gly Ser Pro Gly Trp Val Arg Thr
65                  70                  75                  80 cgc ugg gca cug cug cug cuc uuc ugg cuc ggc ugg cuc ggc aug cuu      288
Arg Trp Ala Leu Leu Leu Leu Phe Trp Leu Gly Trp Leu Gly Met Leu
                85                  90                  95
```

-continued

| | | |
|---|---|---|
| gcu ggu gcc gug guc aua auc gug cga gcg ccg cgu ugu cgc gag cua<br>Ala Gly Ala Val Val Ile Ile Val Arg Ala Pro Arg Cys Arg Glu Leu<br>                100                        105                       110 | | 336 |
| ccg gcg cag aag ugg ugg cac acg ggc gcc cuc uac cgc auc ggc gac<br>Pro Ala Gln Lys Trp Trp His Thr Gly Ala Leu Tyr Arg Ile Gly Asp<br>                115                        120                       125 | | 384 |
| cuu cag gcc uuc cag ggc cac ggc gcg ggc aac cug gcg ggu cug aag<br>Leu Gln Ala Phe Gln Gly His Gly Ala Gly Asn Leu Ala Gly Leu Lys<br>      130                        135                       140 | | 432 |
| ggg cgu cuc gau uac cug agc ucu cug aag gug aag ggc cuu gug cug<br>Gly Arg Leu Xaa Tyr Leu Ser Ser Leu Lys Val Lys Gly Leu Val Leu<br>145                      150                       155                     160 | | 480 |
| ggu cca auu cac aag aac cag aag gau gau guc gca cag acu gac uug<br>Gly Pro Ile His Lys Asn Gln Lys Xaa Xaa Val Ala Gln Xaa Asp Leu<br>                       165                       170                       175 | | 528 |
| cug cag auc gac ccc aau uuu ggc ucc aag gaa gau uuu gac agu cuc<br>Leu Gln Ile Asp Pro Asn Phe Gly Ser Lys Glu Xaa Phe Asp Ser Leu<br>                180                        185                       190 | | 576 |
| uug caa ucg gcu aaa aaa aag agc auc cgu guc auu cug gac cuu acu<br>Leu Gln Ser Ala Lys Lys Lys Ser Ile Arg Val Ile Leu Asp Leu Xaa<br>                     195                       200                     205 | | 624 |
| ccc aac uac cgg ggu gag aac ucg ugg uuc ucc acu cag guu gac acu<br>Pro Asn Tyr Arg Gly Glu Asn Ser Trp Phe Ser Xaa Gln Val Asp Xaa<br>      210                        215                       220 | | 672 |
| gug gcc acc aag gug aag gau gcu cug gag uuu ugg cug caa gcu ggc<br>Val Ala Thr Lys Val Lys Xaa Ala Leu Glu Phe Trp Leu Gln Ala Gly<br>225                      230                       235                     240 | | 720 |
| gug gau ggg uuc cag guu cgg gac aua gag aau cug aag gau gca ucc<br>Val Xaa Gly Phe Gln Val Arg Asp Ile Glu Asn Leu Lys Xaa Ala Ser<br>                          245                       250                     255 | | 768 |
| uca uuc uug gcu gag ugg caa aau auc acc aag ggc uuc agu gaa gac<br>Ser Phe Leu Ala Glu Trp Gln Asn Ile Thr Lys Gly Phe Ser Glu Asp<br>                260                        265                       270 | | 816 |
| agg cuc uug auu gcg ggg acu aac ucc ucc gac cuu cag cag auc cug<br>Arg Leu Leu Ile Ala Gly Xaa Asn Ser Ser Asp Leu Gln Gln Ile Leu<br>             275                       280                       285 | | 864 |
| agc cua cuc gaa ucc aac aaa gac uug cug uug acu agc uca uac cug<br>Ser Leu Leu Glu Ser Asn Lys Asp Leu Leu Leu Xaa Ser Ser Tyr Leu<br>          290                       295                       300 | | 912 |
| ucu gau ucu ggu ucu acu ggg gag cau aca aaa ucc cua guc aca cag<br>Ser Xaa Ser Gly Ser Xaa Gly Glu His Thr Lys Ser Leu Val Thr Gln<br>305                      310                       315                     320 | | 960 |
| uau uug aau gcc acu ggc aau cgc ugg ugc agc ugg agu uug ucu cag<br>Tyr Leu Asn Ala Xaa Gly Asn Arg Trp Cys Ser Trp Ser Leu Ser Gln<br>                       325                       330                     335 | | 1008 |
| gca agg cuc cug acu ucc uuc uug ccg gcu caa cuu cuc cga cuc uac<br>Ala Arg Leu Leu Xaa Ser Phe Leu Pro Ala Gln Leu Leu Arg Leu Tyr<br>             340                       345                       350 | | 1056 |
| cag cug aug cuc uuc acc cug cca ggg acc ccu guu uuc agc uac ggg<br>Gln Leu Met Leu Phe Thr Leu Pro Gly Thr Pro Val Phe Ser Tyr Gly<br>          355                       360                       365 | | 1104 |
| gau gag auu ggc cug gau gca gcu gcc cuu ccu gga cag ccu aug gag<br>Xaa Glu Ile Gly Leu Xaa Ala Ala Ala Leu Pro Gly Gln Pro Met Glu<br>370                      375                       380 | | 1152 |
| gcu cca guc aug cug ugg gau gag ucc agc uuc ccu gac auc cca ggg<br>Ala Pro Val Met Leu Trp Xaa Glu Ser Ser Phe Pro Asp Ile Pro Gly<br>385                      390                       395                     400 | | 1200 |
| gcu gua agu gcc aac aug acu gug aag ggc cag agu gaa gac ccu ggc<br>Ala Val Ser Ala Asn Met Xaa Val Lys Gly Gln Ser Glu Asp Pro Gly<br>                          405                       410                     415 | | 1248 |

```
ucc cuc cuu ucc uug uuc cgg cgg cug agu gac cag cgg agu aag gag    1296
Ser Leu Leu Ser Leu Phe Arg Arg Leu Ser Asp Gln Arg Ser Lys Glu
        420                 425                 430 cgc ucc cua cug cau ggg gac uuc cac gcg uuc ucc gcu ggg ccu gga    1344
Arg Ser Leu Leu His Gly Asp Phe His Ala Phe Ser Ala Gly Pro Gly
        435                 440                 445 cuc uuc ucc uau auc cgc cac ugg gac cag aau gag cgu uuu cug gua    1392
Leu Phe Ser Tyr Ile Arg His Trp Asp Gln Asn Glu Arg Phe Leu Val
        450                 455                 460 gug cuu aac uuu ggg gau gug ggc cuc ucg gcu gga cug cag gcc ucc    1440
Val Leu Asn Phe Gly Xaa Val Gly Leu Ser Ala Gly Leu Gln Ala Ser
465                 470                 475                 480 gac cug ccu gcc agc gcc agc cuc cca gcc aag gcu gac cuc cug cuc    1488
Asp Leu Pro Ala Ser Ala Ser Leu Pro Ala Lys Ala Asp Leu Leu Leu
                485                 490                 495 agc acc cag cca ggc cgu gag gag ggc ccu cuu gag cug gaa cgc        1536
Ser Thr Gln Pro Gly Arg Glu Glu Gly Ser Pro Leu Glu Leu Glu Arg
                500                 505                 510 cug aaa cug gag ccu cac gaa ggg cug cug cuc cgc uuc ccc uac gcg    1584
Leu Lys Leu Glu Pro His Glu Gly Leu Leu Leu Arg Phe Pro Tyr Ala
        515                 520                 525 gcc uga                                                            1590
Ala
```

METHOD USING NEUTRAL AMINO ACID TRANSPORTER EXPRESSING CELL

CROSS-REFERENCE TO RELATED APPLICATION(S)

This application is a divisional of copending patent application U.S. Ser. No. 09/786,389, filed on Jul. 8, 2001, which application was a §371 application of copending international patent application PCT/JP99/04789filed on Sep. 3, 1999, each of which is incorporated by reference.

FIELD OF THE INVENTION

The present invention relates to an amino acid transporter protein or a part thereof, DNA coding for the protein or a part thereof, RNA coding for the protein or a part thereof, DNA hybridizing to the DNA, an expression vector containing the DNA, a transformed cell transformed by the DNA or by the vector, a cell in which the RNA is introduced, an antibody or a part thereof having a reactivity with the protein or a part thereof, a cell which produces the antibody, a labeled DNA in which a part of the DNA is radiolabeled, a labeled RNA in which a part of the RNA is radiolabeled, a labeled antibody in which the antibody or a part of the antibody is labeled, a kit comprising the labeled DNA, a kit comprising the labeled RNA, a kit comprising the labeled antibody, a pharmaceutical composition containing a part of the DNA, a pharmaceutical composition containing a part of the RNA, a pharmaceutical composition containing the antibody or a part of the antibody, a method for determining whether the protein is expressed or for measuring the expressed amount thereof, a method for identifying a substance having an ability of inhibiting the biological activity of the protein, a method for identifying the substance having an ability of inhibiting the transcription of DNA coding for the protein into mRNA, a method for identifying the substance having an ability of inhibiting the expression of the protein, a substance which is identified by the identifying method and a transgenic mouse into which the DNA coding for the protein of the present invention is introduced.

BACKGROUND ART

Amino acids play a very important role not only as a substrate for protein synthesis but also as a precursor in gluconeogenesis and in biosynthesis of many biomolecules such as porphyrin, purine and pyrimidine.

Most of such a biosynthesis reaction is carried out in cells and, therefore, in the cells, various proteins which are generally called amino acid transporters for incorporating amino acid into the cells from outside of the cells are contained in cell membrane.

The amino acid transporter not only functions for supplying amino acids to each cell but also is incorporated into tissues playing a role of an epithelial transport of amino acids in small intestine and renal tubule and a resorption of neurotransmitter in nervous tissue whereby it is oriented at an important position for the expression of a specific function of tissues.

With regard to an amino acid transport mechanism (an amino acid transport system mediated by amino acid transporter), its identification and classification have been carried out using cultured cells and cell membrane samples since about 1960's and, reflecting the diversity of amino acid molecules, there have been identified amino acid transport systems mediated by various amino acid transporters having different substrate specificity (*Physiol. Rev.* Vol. 70, p. 43-77, 1990).

However, such a transport system does not independently function to each amino acid but each amino acid bears an intracellular transport for more than one amino acids using the more than one amino acids as substrates.

Amino acids are classified into basic amino acids (diamino/monocarboxylic acids) having positive charge, acidic amino acids (monoamino/dicarboxylic acids) having negative charge and neutral amino acids (monoamino/monocarboxylic acids; or those excluding basic amino acids or acidic amino acids). Because of such a charge of amino acid, when a neutral amino acid or an acidic amino acid having negative charge, for example, is transported into cells having negative electric potential against the concentration gradient, it is necessary to carry out an active transport associated with some energy consumption.

From such a viewpoint, in amino acid transporters, that which shows a dependency on sodium ($Na^+$) and that which shows an independency on $Na^+$ are present like in the case of a sugar transport system. The $Na^+$-dependent transporter has a big concentrating ability since it is able to transport the amino acid against the concentration gradient by coupling amino acid transport with $Na^+$ transport and, therefore, it plays an important role in the site in a living body where formation of a big concentration difference mediated by cell membrane is requested (*Annual Rev.* Kidney "Structure and Function of Kidney-Specific Organic Solute Transporters", p. 91-100, 1995, published by Chugai Igakusha). Such a $Na^+$-dependent transporter can be further classified into two families, i.e. an $Na^+/Cl^-$-dependent transporter family and an $Na^+/K^-$-dependent transporter family (*Annual Rev. Neurosci.*, Vol. 16, p. 73-93, 1993 and *FASEB J.*, Vol. 7, p. 1450-1459, 1993).

Further, in combination of such a charge property, amino acid transporters can be classified, in view of the substrate specificity, into molecule where basic amino acid (diamino/monocarboxylic acid) is a substrate, molecule where acidic amino acid (monoamino/dicarboxylic acid) is a substrate and molecule where neutral amino acid (monoamino/monocarboxylic acid; or that excluding basic amino acid or acidic amino acid) is a substrate.

It has been known that, for example, a basic amino acid having amino group or imidazole group on the side chain such as arginine, lysine and histidine (basic amino acid which is nearly neutral) is transported mostly by an $Na^+$-independent amino acid transporter $y^+$ (*J. Membrane Biol.*, Vol. 66, p. 213-225, 1982). It has been known that an acidic amino acid having carboxyl group on the side chain such as glutamic acid and aspartic acid is transported by an $Na^+$-dependent amino acid transporter $X^-_{A,G}$ (*Biochim. Biophys. Acta*, Vol. 732, p. 24-31, 1983). In the case of transport of a neutral amino acid to which many amino acids belong, it has been known that an $Na^+$-independent amino acid transporter L (*Ann. Rev. Physiol.*, Vol. 46, p. 417-433, 1984) and $Na^+$-dependent amino acid transporters A and ASC (*Ann. Rev. Physiol.*, Vol. 46, p. 417-433, 1984 and *J. Membrane Biol.*, Vol. 52, p. 83-92, 1980) play an important role (*Physiol. Rev.*, Vol. 70, p. 43-77, 1990 and *Saishin Igaku*, Vol. 50, p. 1997-2004, 1995).

As mentioned already, amino acids play a very important role as materials in biosynthesis of various biocomponents taking place in cells and, therefore, it is presumed that abnormal transport of the amino acid into cell participates in various symptoms.

It has been known from the studies up to now that the symptoms in which abnormal transport mechanism of the amino acid into cells are participated are aminoaciduia where disorder of amino acid resorption from renal tubule occurs and amyotrophic lateral sclerosis, etc. in which disorder of glutamic acid incorporation and nerve cell death are participated (*Annual Rev.* Kidney "Structure and Function of Kidney-Specific Organic Solute Transporters", p. 91-100, 1995, published by Chugai Igakusha; *Saishin Igaku*, Vol. 50, p. 1997-2004, 1995; and *Saishin Igaku*, Vol. 51, p. 64-70, 1996).

Amino acid transporters play an essential and very important role in incorporation of amino acids necessary for generation, differentiation, proliferation and maintenance of all cells and, therefore, they are believed to participate not only in the above-mentioned symptoms but also in onset of many other symptoms. In addition, when the indispensability of amino acid transporter in living body is taken into consideration, it is hardly concluded that incorporation of various amino acids is not mediated by several already-identified transporters only but it is believed that many other unknown amino acid transporters will be present.

Identification of such unknown amino acid transporters which play a role essential for existence and maintenance of cells, tissues, organs and living body has a possibility of clarification of causes for onset of various diseases for which the causes have not been clarified yet. In addition, if the relation between such amino acid transporters and various diseases is made clear, an effective treatment of such diseases will become possible by regulation of biological function or expression of the amino acid transporters. Accordingly, it is a pressing need to identify new amino acid transporter and to clarify the relation between the transporter molecule and a symptom.

However, in spite of medical and social needs as such, it is a current state that there has been little progress in identification of an amino acid transporter and clarification of an amino acid transport mechanism.

Thus, in order to identify an amino acid transporter molecule, it is necessary to purify the molecule and, in order to analyze the activity of the purified substance, it is necessary to reconstitute the purified substance to cell membrane so that an amino acid transport activity is regenerated. However, an amino acid transporter molecule has a relatively little expression amount as a membrane protein and has a relatively small regenerating efficiency and, therefore, there is a difficulty in the technique in the identification of new molecules.

In addition, identification of an amino acid transporter which is specifically expressed in abnormal cells directly participating in the symptom such as cancer cells (tumor cells) and plays a role of supplying an amino acid to the abnormal cells has a very important significance in the clarification of existence and proliferation of such symptom-related cells and also in the development of therapeutic methods for cancer, etc. However, an amino acid transporter is inherently a molecule essential for the existence of normal cells and is believed to be present in a wide range of cell species and, accordingly, it is not easy to identify an amino acid transporter molecule which is expressed specifically in such abnormal cells.

As a neutral amino acid transporter, ASCT1 and ASCT2 have been cloned as sodium-dependent transporters (Kanai, *Curr. Opin. Cell Biol.*, 9, 565 (1997)). However, the main substrates thereof are alanine, serine, cysteine, threonine and glutamine and their substrate specificity is different from a neutral amino acid transporting system L. Further, glycine transporter and proline transporter have been cloned but their substrate specificity is different from neutral amino acid transport system L (Amara and Kuhar, *Annu. Rev. Neurosci.*, 16, 73 (1993)).

Although not a transporter per se, cDNAs of rBAT and 4F2hc which are a type II membrane glycoprotein having only one transmembrane structure believed to be an activating factor for an amino acid transporter have been cloned and it has been known that, when they are expressed in oocytes of *Xenopus laevis*, uptake of a basic amino acid is activated together with that of a neutral amino acid (Palacin, *J. Exp. Biol.*, 196, 123 (1994)).

Accordingly, it is an effective key for providing a therapeutic method for the symptom and disease that an amino acid transporter molecule which has not been identified yet and is specifically expressed in abnormal cells deeply associated with such a symptom is identified and that the relation between the molecule and existence/proliferation of the abnormal cells is clarified.

Thus, when the biological activity of the amino acid transporter molecule or the expression of the molecule is controlled, it is now possible to treat the diseases.

The present inventors have paid their attention to the already-known cell membrane surface molecule 4F2 (CD98) which is believed to be essential for the proliferation of tumor cells in order to investigate a novel amino acid transporter which is specifically expressed in such symptom-related abnormal cells or, particularly, tumor cells and have succeeded in identifying a novel amino acid transporter molecule named LAT1 (L-type amino acid transporter-1) which is particularly significantly expressed in tumor cells as compared with the expression in normal cells.

Thus, for a quick cell division and continuous growth and proliferation, the tumor cells are to be provided with nutrients such as amino acids and saccharides thereinto and it is believed that such a providing is carried out by means of an up-regulation of an amino acid transporter which is specific to the nutrients (*Physiol. Rev.*, Vol. 70, p. 43-77, 1990). For growth, proliferation and maintenance of the tumor cells, a protein biosynthesis is to be carried out in the cells and, therefore, incorporation of the essential amino acids into the cells (transport from outside of the cells to inside of the cells) is particularly important.

From the studies up to now, it has been believed that, for the proliferation of tumor cells, a known cell membrane surface antigen named 4F2 (CD98) classified into a type II membrane glycoprotein believed to have a function of activating the amino acid transporter which has not been identified yet will play an important role (*J. Immunol.*, Vol. 126, p. 1409-1414, 1981; *J. Immunol.*, Vol. 129, p. 623-628, 1982; *Proc. Natl. Acad. Sci.* USA., Vol. 84, p. 6526-6530, 1987; *Cancer Res.*, Vol. 46, p. 1478-1484, 1986; *J. Biol. Chem.*, Vol. 267, p. 15285-15288, 1992; *Proc. Natl. Acad. Sci.* USA, Vol. 89, p. 5606-5610, 1992; *Biochem. J.*, Vol. 324, p. 535-541, 1997; and *J. Exp. Biol.*, Vol. 196, p. 123-137, 1994).

Under such circumstances, the present inventors have carried out an intensive investigation for identification of human tumor cell membrane surface molecule which conjugates or interacts with a 4F2 molecule and found a gene coding for a novel amino acid transporter LAT1 having the following characteristics whereupon the present invention has been accomplished.

DISCLOSURE OF THE INVENTION

The amino acid transporter LAT1 or, particularly, the amino acid transporter LAT1 derived from human being in accordance with the present invention has the following characteristics.

(1) As a result of a northern blotting using tumor cells derived from human being and mRNA derived from human normal tissues, its expression is noted as a band of about 4.8 kb in tumor cells derived from human being of a wide range including stomach signet ring cell carcinoma (KATO III), malignant melanoma (G-361) and lung small cell carcinoma (RERF-LC-MA). In the human normal tissues, its expression is similarly confirmed as a band of about 4.8 kb only in specific and limited tissues where neogenesis and proliferation of cells are vigorous (placenta, liver of fetus, bone marrow, testicle, brain and peripheral leukocytes).

(2) Open reading frame (ORF; including termination codon) has a base sequence comprising 1,524 bases (a base sequence from 66th to 1589th bases in the base sequence mentioned in SEQ ID NO:1) and the ORF codes for an amino acid sequence comprising 507 amino acids as a whole and has a molecular weight of about 55 kDa (calculated value) (SEQ ID NO:2).

(3) As a result of a hydrophobic plot analysis, human LAT1 has 12 transmembrane regions and is identified as a membrane surface molecule having a phosphorylated site by tyrosine protein kinase (119th Tyr in an amino acid sequence of SEQ ID NO:2) and a phosphorylated site by protein kinase C (189th Ser and 346th Ser in an amino acid sequence of SEQ ID NO:2) in an intracellular region.

(4) In a cell in which human LAT1 and human 4F2hc (4F2 heavy chain) are co-expressed, a very strong incorporation of leucine (Leu), isoleucine (Ile), phenylalanine (Phe), methionine (Met), tyrosine (Tyr), tryptophan (Trp) and valine (Val) which are neutral amino acids and histidine (His) which is a nearly neutral basic amino acid is confirmed. In addition, significant incorporation of threonine, cysteine, asparagine and glutamine which are other neutral amino acids is confirmed as well.

(5) In a cell in which human LAT1 and human 4F2hc are co-expressed, not only the incorporation of the above-mentioned amino acids but also known incorporation of pharmaceuticals such as L-DOPA which is a remedy for Parkinson's disease and physiologically active substance such as triiodothyronine (thyroid hormone) are confirmed. In addition, incorporation of BCH (2-amino-2-norbornane-carboxylic acid) known as an inhibitor for incorporation of neutral amino acids is confirmed as well.

(6) In a Michaelis-Menten kinetic test, a Km value showing the affinity of the human LAT1 with the above-mentioned various substrates is about 21 µM.

(7) The above-mentioned incorporation of various amino acids, pharmaceuticals and physiologically active substances mediated by LAT1 into the cells is not dependent upon $Na^+$ ion and $Cl^+$ ion.

Thus, the present invention discloses, for the first time in the world, an amino acid transporter in which a specific expression is noted in tumor cells of a wide range as compared with normal cells and which is believed to be essential for existence and proliferation of various tumor cells having a wide substrate specificity.

From the above-mentioned characteristics of the amino acid transporter molecule of the present invention, the molecule is quite hopeful as a target in the development of an antitumor agent (anticancer agent) for example. Thus, when a pharmaceutical agent having an activity of suppressing the biological activity of the molecule or the expression of the molecule (such as antisense DNA pharmaceuticals, antisense RNA pharmaceuticals, antibody pharmaceuticals, antibody fragment pharmaceuticals, peptide antagonist pharmaceuticals and non-peptide antagonist pharmaceuticals including low-molecular compounds) is used so as to suppress the incorporation of nutrients (various amino acids and physiologically active substance) into tumor cells mediated by the molecule, it is now possible that the tumor cells are made in a hungry state and that existence and proliferation of the tumor cells are suppressed.

Accordingly, the protein of the present invention or a part thereof, DNA coding for the protein or a part thereof, RNA coding for the protein or a part thereof, DNA hybridizing to the DNA, expression vector containing the DNA, transformed cell transformed by the DNA or by the vector, a cell in which the RNA is introduced, antibody or a part thereof having a reactivity with the protein or a part thereof, a cell which produces the antibody, a labeled DNA in which a part of the DNA is radiolabeled, a labeled RNA in which a part of the RNA is radiolabeled, a labeled antibody in which the antibody or a part of the antibody is labeled, a kit comprising the labeled DNA, a kit comprising the labeled RNA and a kit comprising the labeled antibody are quite useful as a pharmaceutical agent having such an antitumor effect and/or as a reagent in the development of such pharmaceuticals.

In addition, when the above-mentioned DNA, RNA or various substances of the present invention such as transformed cell are used, it is also possible to provide various identifying methods (or assay methods) for such various pharmaceuticals.

BRIEF DESCRIPTION OF THE DRAWINGS

FIG. 1 shows a homology in amino acid sequence of a human amino acid transporter LAT1 with that of a rat amino acid transporter LAT1.

FIG. 24. Upper graph shows the concentration dependency of T24 cells for a leucine incorporation (Michaelis-Menten kinetic test); lower graph shows the result of analysis of concentration dependency of T24 cells for a leucine incorporation by Eadie-Hoffstee plots.

DESCRIPTION OF THE PREFERRED EMBODIMENTS

Figure 2:
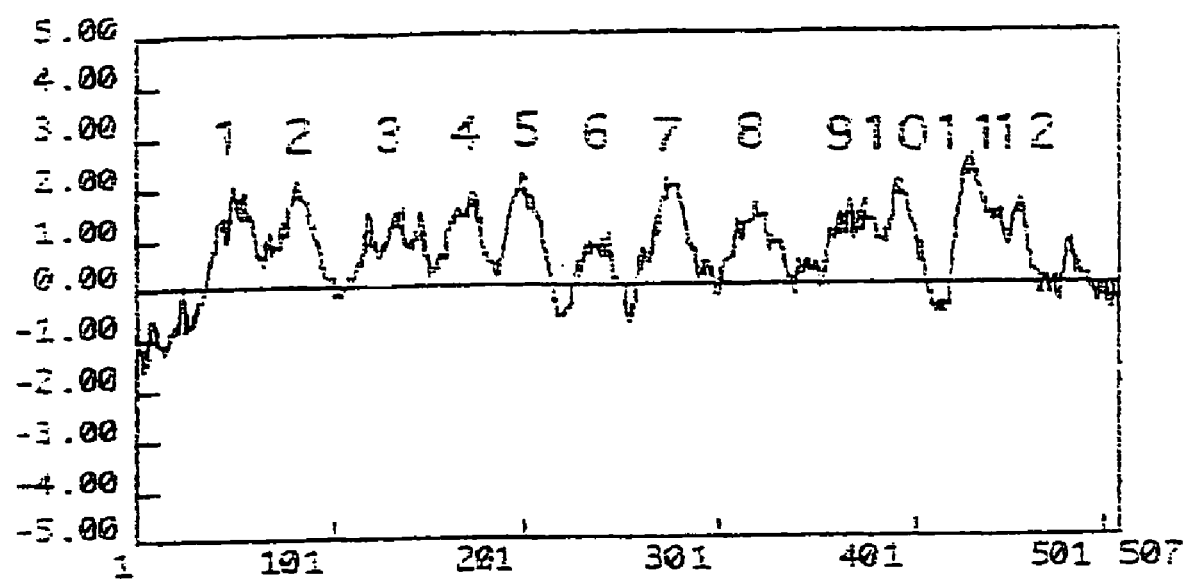
FIG. 2 shows hydrophilic and hydrophobic regions of a human amino acid transporter LAT1 by a hydrophobic plot analysis.

Each of the various inventions in the present application specifically has the following usefulness.

DNA, RNA and transformed cell of the present invention are useful not only in the manufacture of the protein of the present invention as a recombined protein using a gene recombination technique but also as a reagent (tool) for drug design, screening and identification such as for a pharmaceutical agent for controlling (activating, suppressing and inhibiting) the biological activity of the protein of the present invention, a pharmaceutical agent for inhibiting the transcription of the protein of the present invention into mRNA, a pharmaceutical agent for inhibiting the translation of the mRNA into the protein of the present invention, a pharmaceutical agent for inhibiting the interaction of the protein with other molecule, etc.

To be more specific, DNA of the present invention can be used not only in an assay for the identification of a pharmaceutical agent controlling the biological activity of the protein of the present invention but also in an assay for the identification of a pharmaceutical agent controlling the expression of the protein of the present invention.

In the former assay, cells of mammals, etc. are transformed by DNA coding for the amino acid transporter molecule of the present invention to express the molecule in the cells, the transformed cells are incubated in the coexistence of the test substance and the substrate (such as amino acid) for the molecule, the numbers of the substrate incorporated into the cells thereby are compared with the incorporation in the control cells and the activity of the test substance to the control of the biological activity of the amino acid transporter of the present invention is evaluated.

The latter assay is represented by the so-called reporter gene assay which is commonly used in the assay, screening and the identification of such a pharmaceutical agent and by the so-called high through put screening where the reporter gene assay is a principle and the screening is carried out by a machine (robot) (*Soshiki Baiyo Kogaku*, Vol. 23, No. 13, p. 521-524; and U.S. Pat. No. 5,670,113).

In the present invention, DNA coding for the amino acid transporter molecule of the present invention, DNA coding for the expression regulation control region of the DNA and DNA coding for a reporter protein molecule emitting the fluorescence such as luciferase are inserted in such a manner that, depending upon the expression of the transporter molecule, the reporter protein molecule is able to be expressed, the resulting expression vector is used for transformation of the cells which are commonly used in the manufacture of gene recombinant protein, the resulting transformed cells are contacted to the test compound, and the amount of the transporter molecule which is expressed depending upon the action of the compound is indirectly measured by measuring the amount of the fluorescence emitted from the reporter protein which is expressed together with the expression of the molecule whereupon it is analyzed whether the compound affects the expression of the transporter molecule (U.S. Pat. Nos. 5,436,128 and 5,401,629).

Moreover, the RNA of the present invention is able to be used for an assay for the identification of a pharmaceutical agent which controls the biological activity of the amino acid transporter protein molecule of the present invention.

Thus, the present assay is that the RNA coding for the amino acid transporter molecule of the present invention is injected into oocytes of *Xenopus laevis* for example to express the transporter molecule in the cells, an incubation is carried out in the coexistence of the test substance and the substrate (amino acid, etc.) of the molecule and the amount of the substrate incorporated into the cells is compared with the incorporation into the control cells whereupon the activity of the test substance to the control of the biological activity of the amino acid transporter of the present invention is evaluated.

A part of the DNA of the present invention and a part of the RNA thereof may be used as a probe in the case of identification of DNA or RNA which is hybridized in a colony hybridization method or a plaque hybridization method. In addition, a part of the DNA of the present invention may be used as a primer for the amplification of the gene coding for the DNA of the present invention or the transporter molecule of the present invention using a PCR (polymerase chain reaction).

Further, a part of the DNA of the present invention, the DNA which is complementary to the DNA and a part of the RNA of the present invention are not only useful as the reagent as mentioned above but also useful as the so-called antisense DNA pharmaceutical agent or antisense RNA pharmaceutical agent.

Thus, antisense pharmaceutical agent is an agent according to a mechanism of inhibiting the transcription from DNA to mRNA or the translation from the mRNA to protein utilizing the nature of bonding a part of base sequence of DNA, apart of base sequence complementary to the base sequence of the DNA or a part of base sequence of RNA to DNA or RNA having a sequence complementary to the base sequence thereof. When a part of the antisense sequence in the antisense pharmaceutical agent is subjected to a chemical modification, it is possible to modify the properties such as increase in a half life in blood, permeability into cells, targeting efficiency to disease target site, etc.

In the protein of the present invention, the state where the protein molecule is expressed on the cell surface is utilized whereby it is possible as mentioned above to identify the pharmaceutical agent which controls the biological activity of the protein of the present invention or the expression of the protein. In addition, based upon the amino acid sequence of the protein, it is also possible to design a peptide antagonist having an ability of inhibiting the biological activity of the protein. The peptide antagonist designed as such is useful as a pharmaceutical agent where binding of the amino acid transporter which is a protein of the present invention to a substrate or binding of a protein of the present invention to other molecule is competitively inhibited so that the biological function of the protein of the present invention is not achieved.

The protein of the present invention or a part thereof and the cells such as transformed cell expressing the protein are useful as an immunosensitized antigen in the preparation of antibody (antiserum, monoclonal antibody) to the protein of the present invention.

Antiserum (polyclonal antibody) having a reactivity with the amino acid transporter molecule which is a protein of the present invention and a monoclonal antibody are useful as antibody pharmaceutical agents by inhibiting (neutralizing) the achievement of biological activity of the molecule by binding to the molecule.

In addition, the antibody is useful as a reagent in the analysis (immunohistological staining, western blotting, ELISA, etc.) of expressed state of the protein of the present invention in various biosamples (cells, tissues, organs or body fluids) by labeling with various substances which are able to achieve a detectable signal.

Like in such a labeled antibody, the labeled DNA where the DNA of the present invention or a part thereof is labeled with various substances which are able to achieve a detectable signal is useful as a reagent in a test (such as southern blotting, FISH, etc.) in the identification of the gene coding for the protein of the present invention.

In addition, a radiolabeled RNA where the RNA of the present invention or a part thereof is similarly labeled with radioisotope is useful as a reagent in an analysis (such as northern blotting) of expressed state of mRNA coding for the protein of the present invention in cells, tissues or organs.

Further, with regard to the DNA of the present invention, when the DNA of an amino acid transporter derived from human being which is an embodiment of the present invention is introduced into mammals other than human being such as mouse, it is possible to prepare a transgenic animal as a model animal.

It is furthermore possible that a gene coding for the amino acid transporter of the present invention derived from human being is used as a probe to clone a gene coding for a homologue protein derived from rabbit or mouse and, based upon the resulting genetic information, the intrinsic gene coding for the homologue protein of mouse or rabbit is destroyed (inactivated) to prepare a model animal (knockout animal). When physical, biological, pathological and genetic characteristics of such a model animal are analyzed, functions of the amino acid transporter according to the present invention can be clarified in more detail.

In addition, when the model animal where the intrinsic gene is destroyed as such is crossed with the transgenic animal, it is possible to prepare a model animal having only the gene (DNA) which codes for the amino acid transporter of the present invention derived from human being. When the above-mentioned pharmaceutical agent (antisense pharmaceutical agent, peptide antagonist, low-molecular non-peptide compound, antibody, etc.) which controls the biological activity of the amino acid transporter molecule of the present invention or the expression of the molecule is administered to this model animal, it is possible to evaluate the therapeutic effect of the pharmaceutical agent.

Thus, the present invention is to provide the substance, the drug, the reagent and the method having a very high utility in industry as mentioned above which is described in each of the following <1> to <55>.

<1> Protein which is a cell surface protein having an ability of mediating the transport of amino acid into cell and having an ability of mediating the incorporation of at least one amino acid selected from a group consisting of leucine (Leu), isoleucine (Ile), phenylalanine (Phe), methionine (Met), tyrosine (Tyr), tryptophan (Trp), valine (Val) and histidine (His) into the cell in an $Na^+$-independent manner.

<2> The protein according to <1>, wherein, when it coexists with a 4F2hc protein classified under a type II membrane glycoprotein or a part thereof, it has an ability of transportation of neutral amino acid and substances similar thereto.

<3> The protein according to <2>, wherein the 4F2hc protein classified under a type II membrane glycoprotein is a protein having an amino acid sequence mentioned in SEQ ID NO:6 or NO:8 or an amino acid sequence where a part of amino acids thereof is deleted, substituted or added.

<4> The protein according to any of <1> to <3>, wherein it is a protein derived from human being or rat.

<5> The protein according to any of <1> to <4>, wherein it has an amino acid sequence of any of the following (1) and (2).

(1): an amino acid sequence mentioned in SEQ ID NO: 2 or NO:4

(2): an amino acid sequence mentioned in SEQ ID NO:2 or NO:4 where one or more amino acid(s) is/are deleted, substituted or added.

<6> A polypeptide containing a partial amino acid sequence in the amino acid sequence mentioned in SEQ ID NO:2 or NO:4 and having an antigenicity.

<7> DNA coding for any of the protein mentioned in <1> to <5>.

<8> The DNA according to <7>, wherein it is a DNA derived from human being or rat.

<9> DNA coding for a cell surface protein which hybridizes under a stringent condition to the DNA having a base sequence of from 66th to 1586th bases mentioned in SEQ ID NO:1 or having a base sequence of from 64th to 1599th bases mentioned in SEQ ID NO:3 and has an ability of mediating the incorporation of at least one kind of amino acid into cell.

<10> The DNA according to <9>, wherein it codes for a cell surface protein where incorporation of amino acid into the cell is mediated by the coexistence of a 4F2hc protein classified under the type II membrane glycoprotein or a part thereof.

<11> The DNA according to <10>, wherein the 4F2hc protein classified under the type II membrane glycoprotein has an amino acid sequence mentioned in SEQ ID NO:6 or NO:8 or an amino acid sequence where a part of amino acids is deleted, substituted or added.

<12> RNA which is able to be derived from the DNA mentioned in <7> to <11>.

<13> The RNA according to <12>, wherein it is an RNA having a base sequence mentioned in SEQ ID NO:26 or NO:27.

<14> An expression vector containing the DNA mentioned in any of the above <7> to <11>.

<15> A transformant cell which is transformed by the expression vector mentioned in the above <14>.

<16> The transformant cell according to <14> or <15>, wherein the transformant cell is further transformed by a DNA containing a base sequence comprising a base sequence of from 110th to 1696th bases in the base sequence mentioned in SEQ ID NO:5 and any one of nonsense base sequence represented by TAG, TGA or TAA adjacent to the 1696th base.

<17> The transformant cell according to any of the above <14> to <16>, wherein the transformant cell is further transformed by a DNA coding for a reporter protein.

<18> A cell which is not derived from human being into which the RNA mentioned in the above <12> or <13> is introduced.

<19> The cell according to <18>, wherein the cell is an oocyte of *Xenopus laevis*.

<20> An antiserum or a polyclonal antibody having a reactivity with the protein mentioned in any of the above <1> to <5> or to the polypeptide mentioned in the above <6>.

<21> A monoclonal antibody having a reactivity with the protein mentioned in any of the above <1> to <5> or to the polypeptide mentioned in the above <6> or a part of the monoclonal antibody.

<22> The monoclonal antibody or a part of the monoclonal antibody according to <21>, wherein the monoclonal antibody is a recombined chimera monoclonal antibody comprising a variable region of immunoglobulin derived from mammals except human being and a constant region of immunoglobulin derived from human being.

<23> The monoclonal antibody or a part of the monoclonal antibody according to <21>, wherein the monoclonal antibody is a recombined human type monoclonal antibody comprising all or a part of a complementarity-determining region of a hypervariable region of immunoglobulin derived from mammals except human being, a frame region of a hypervariable region of immunoglobulin derived from human being and a constant region of immunoglobulin derived from human being.

<24> The monoclonal antibody or a part of the monoclonal antibody according to any of the above <21> to <23>, wherein the monoclonal antibody is a human monoclonal antibody.

<25> A cell which produces the monoclonal antibody mentioned in any of the above <21> to <24>.

<26> The cell according to the above <25>, wherein the cell is a fused cell prepared by a fusion of a B cell derived from non-human mammals having an ability of producing the monoclonal antibody with a myeloma cell derived from mammals.

<27> The cell according to the above <25>, wherein the cell is a genetically recombined cell transformed by introduction of DNA coding for heavy chain of the monoclonal antibody, DNA coding for light chain thereof or both of the DNA into the cell.

<28> A pharmaceutical composition containing the DNA mentioned in any of the above <7> to <11> and a pharmaceutically acceptable carrier.

<29> The pharmaceutical composition according to <28>, wherein the pharmaceutical composition is used for suppressing the growth of the tumor cells.

<30> A pharmaceutical composition containing the RNA mentioned in the above <12> or <13> and a pharmaceutically acceptable carrier.

<31> The pharmaceutical composition according to <30>, wherein the pharmaceutical composition is used for suppressing the growth of the tumor cells.

<32> A pharmaceutical composition containing the antiserum or the polyclonal antibody mentioned in the above <20> and a pharmaceutically acceptable carrier.

<33> The pharmaceutical composition according to <32>, wherein the pharmaceutical composition is used for suppressing the growth of the tumor cells.

<34> A pharmaceutical composition containing the monoclonal antibody mentioned in any of the above claims <21> to <24> or a part of the monoclonal antibody and a pharmaceutically acceptable carrier.

<35> The pharmaceutical composition according to <34>, wherein the pharmaceutical composition is used for suppressing the growth of the tumor cells.

<36> A labeled monoclonal antibody in which the monoclonal antibody mentioned in any of the above <21> to <24> is labeled with a labeling substance which is able to give a detectable signal either solely or by the reaction with other substance.

<37> The labeled monoclonal antibody according to the above <36>, wherein the labeling substance is enzyme, fluorescent substance, chemiluminescent substance, biotin, avidin or radioisotope.

<38> A kit which is to detect the protein having the amino acid sequence mentioned in SEQ ID NO:2 or a fragment where the kit comprises the labeled monoclonal antibody mentioned in the above <36> or <37>.

<39> A method for the examination whether protein is expressed in a sample or for the examination of the expressed amount, characterized in that, the method comprises:

(1) a step where the sample is contacted to the labeled monoclonal antibody mentioned in the above <36> and <37> and (2) a step where the amount of the labeled monoclonal antibody bonded to the sample is measured by detecting fluorescence, chemiluminescence or radioactivity depending upon the type of the labeling substance bonded to the labeled monoclonal antibody.

<40> The method according to the above <39>, wherein the sample is tumor cell, tumor tissue, tumor-having organ or a part thereof.

<41> A labeled DNA in which the DNA mentioned in any of the above <7> to <11> or a fragment thereof is labeled with enzyme, fluorescent substance, chemiluminescent substance, biotin, avidin or radioisotope.

<42> A radiolabeled RNA in which the RNA mentioned in the above <12> or <13> is labeled with a radioisotope.

<43> A kit for detecting the gene coding for the protein mentioned in any of the above <1> to <5>, characterized in that, the kit comprises the labeled DNA mentioned in the above <41> or the radioactive RNA mentioned in the above <42>. To be more precise, a kit for detecting the gene coding for the protein having an amino acid sequence mentioned in SEQ ID NO:2, characterized in that, the kit comprise the labeled DNA mentioned in the above <41> or the radioactive RNA mentioned in the above <42>.

<44> A method for detecting the action as a substrate of a test substance to the ability for transporting the neutral amino acids of the protein using the protein mentioned in any of <1> to <5>.

<45> The method according to the above <44>, wherein the cell transformed by the DNA mentioned in any of the above <7> to <11> is used.

<46> The method according to the above <44>, wherein an oocyte of *Xenopus laevis* is used.

<47> The method according to any of the above <44> to <46>, wherein the test substance is a substance other than an amino acid.

<48> A method for screening the test substance having an action of suppressing the ability for transport of neutral amino acid and similar substance thereto of the protein using the protein mentioned in any of the above <1> to <5>. To be more precise, a method for identification of a substance having an ability of inhibiting the ability of mediating the incorporation of any one amino acid selected from a group consisting of leucine (Leu), isoleucine (Ile), phenylalanine (Phe), methionine (Met), tyrosine (Tyr), histidine (His), tryptophan (Trp) and valine (Val) into cells which is a biological function of the protein having an amino acid sequence mentioned in SEQ ID NO:2, characterized in that, the method comprises the steps of the following (1) and (2).

(1) a step in which any of the cells mentioned in the following (a) to (d) is incubated in the coexistence of the substance and a radiolabeled amino acid where any one amino acid selected from a group consisting of leucine (Leu), isoleucine (Ile), phenylalanine (Phe), methionine (Met), tyrosine (Tyr), histidine (His), tryptophan (Trp) and valine (Val) is labeled with a radioisotope or in the presence of the radiolabeled amino acid only:

(a) a naturally-occurring cell in which a protein having an amino acid sequence mentioned in SEQ ID NO:2 and a protein having an amino acid sequence mentioned in SEQ ID NO:6 are co-expressed;

(b) a recombinant cell in which a protein having an amino acid sequence mentioned in SEQ ID NO:2 and a protein having an amino acid sequence mentioned in SEQ ID NO:6 are co-expressed by a co-transformation using a DNA containing a base sequence of 66th to 1586th bases in the base sequence mentioned in SEQ ID NO:1 and a base sequence comprising any one nonsense base sequence represented by TAG, TGA or TAA adjacent to the 1586th base and a DNA containing a base sequence of 110th to 1696th bases in the base sequence mentioned in SEQ ID NO:5 and a base sequence comprising any one nonsense base sequence represented by TAG, TGA or TAA adjacent to the 1696th base;

(c) a non-human-derived recombinant cell in which a protein having an amino acid sequence mentioned in SEQ ID NO:2 and a protein having an amino acid sequence mentioned in SEQ ID NO:6 are co-expressed by a co-introduction of an RNA containing a base sequence of 1st to 1521st bases in the base sequence mentioned in SEQ ID NO:26 and a base sequence comprising any one nonsense base sequence represented by UAG, UGA or UAA adjacent to the 1521st base and an RNA containing a base sequence of 1st to 1587th bases in the base sequence mentioned in SEQ ID NO:27 and a base sequence comprising any one nonsense base sequence represented by UAG, UGA or UAA adjacent to the 1587th base; or (d) a tumor cell derived from human being; and (2) a step in which the radioactivity of the cell incubated in the coexistence of the substance and the radiolabeled amino acid and the radioactivity of the cell incubated in the presence of the radiolabeled amino acid only are measured and the difference between them is compared.

<49> The method according to <48>, wherein the cell which is transformed by the DNA mentioned in any of the above <7> to <11> is used.

<50> The method according to <48>, wherein an oocyte of *Xenopus laevis* is used.

<51> A method for the identification of a substance having an ability of inhibiting the transcription of the DNA mentioned in any of the above <7> to <11> to mRNA or the expression of the protein mentioned in any of the above <1> to <5>.

<52> A substance which is detected, screened or identified by a method mentioned in any of the above <44> to <51>.

<53> The substance according to <52>, wherein the substance is a substance having an ability of inhibiting the growth of tumor cell.

<54> A transgenic mouse having an extrinsic gene, characterized in that, a DNA coding for a protein having an amino acid sequence mentioned in SEQ ID NO:2 or NO:4 is incorporated on an intrinsic gene of the mouse whereupon the mouse has a cell expressing the protein in its body.

<55> The transgenic mouse according to <54>, wherein the DNA is a DNA which contains a base sequence comprising a base sequence of from 66th to 1586th bases in the base sequence mentioned in SEQ ID NO:1 and any one nonsense base sequence represented by TAG, TGA or TAA adjacent to the 1586th base or a base sequence comprising a base sequence of from 64th to 1599th bases in the base sequence mentioned in SEQ ID NO:3 and any one nonsense base sequence represented by TAG, TGA or TAA adjacent to the 1599th base.

The present invention will now be illustrated in detail as hereunder by clarifying the meanings of the terms used in the present invention and also the general method for the manufacture of DNA, proteins, antibodies, cells produced by the antibody, transformants, labeled DNA, labeled RNA, labeled antibodies, pharmaceutical compositions, transgenic mice, etc. of the present invention.

The term "mammals" used in the present invention means all mammals such as human being, cattle, horse, pig, goat, sheep, dog, cat, chicken, rabbit, rat, hamster, guinea pig and mouse; preferably, human being, cattle, horse, pig, goat, sheep, dog, cat, chicken, rabbit, rat, hamster, guinea pig and mouse; and, particularly preferably, human being, rat, hamster, guinea pig and mouse.

The terms "mammals except human being" and "non-human mammals" used in the present invention have the same meaning and stand for all mammals except human being in the above-defined mammals.

"Amino acid" used in the present invention means all amino acids present in nature and, preferably, it is the amino acid represented as follows in accordance with the three-letter notation or one-letter notation by alphabets used for representing the amino acid.

Thus, glycine (Gly/G), alanine (Ala/A), valine (Val/V), leucine (Leu/L), isoleucine (Ile/I), serine (Ser/S), threonine (Thr/T), aspartic acid (Asp/D), glutamic acid (Glu/E), asparagine (Asn/N), glutamine (Gln/Q), lysine (Lys/K), arginine (Arg/R), cysteine (Cys/C), methionine (Met/M), phenylalanine (Phe/F), tyrosine (Tyr/Y), tryptophan (Trp/W), histidine (His/H) and proline (Pro/P).

Amino acids are classified into acidic, basic and neutral amino acids according to the state of polarity and charge of the amino acid. When the above-mentioned amino acids are classified according to such a classification, they are classified as follows and, when the degree of polarity and charge are more finely classified or a classification is carried out by taking other parameters into consideration, there are amino acids which are not always suitable for the following classification.

(Acidic amino acids)
Aspartic acid (Asp/D) and glutamic acid (Glu/E).
(Basic amino acids)
Lysine (Lys/K), arginine (Arg/R) and histidine (His/H).
(Neutral amino acids)
Leucine (Leu/L), isoleucine (Ile/I), phenylalanine (Phe/F), methionine (Met/M), tyrosine (Tyr/Y), tryptophan (Trp/W), valine (Val/V), histidine (His/H), threonine (Thr/T), cysteine (Cys/C), asparagine (Asn/N), glutamine (Gln/Q), glycine (Gly/G), alanine (Ala/A), serine (Ser/S) and proline (Pro/P).

The term "protein" used in the present invention means a molecule being derived from the above-mentioned mammals and having a specific amino acid sequence comprising the above-mentioned amino acids.

The "protein" of the present invention is a protein which is mentioned in any of the above-mentioned <1> to <5>. To be more specific, it is "a cell surface protein having an ability of mediating the transport of an amino acid into cell and the protein has an ability of mediating an incorporation of any one amino acid selected from a group consisting of leucine (Leu), isoleucine (Ile), phenylalanine (Phe), methionine (Met), tyrosine (Tyr), histidine (His), tryptophan (Trp) and valine (Val) in the cell in which the protein of the following (1) or (2) is expressed:
(1) a protein having an amino acid sequence mentioned in SEQ ID NO:6 or NO:8; or
(2) a homologous protein to the protein having an amino acid sequence mentioned in SEQ ID NO:6 or NO:8 and being coded by DNA which hybridizes to DNA containing a base sequence mentioned in SEQ ID NO:5 or NO:7 under a stringent condition"

The above-mentioned protein of the present invention therefore means a protein which, when the protein of the present invention is co-expressed on a cell membrane where a human-derived cell membrane surface molecule 4F2hc having an amino acid sequence mentioned in SEQ ID NO:6 or a homologous protein thereto derived from non-human animal is expressed, is able to give a property of inducing the incorporation of any one of the above-mentioned amino acids into the cell.

Here, the "homologous protein" means a protein derived from animal species except human being having a sequence homology to the amino acid sequence (SEQ ID NO:6) of human-derived cell membrane surface molecule 4F2hc, being believed to be derived from the common ancestor protein in terms of evolution and having the same physiological function as that of the human-derived 4F2hc.

Preferably, the protein of the present invention is any of the proteins of the following (1) and (2).

(1) a protein having an amino acid sequence mentioned in SEQ ID NO:2; or (2) a protein having an amino acid sequence where one or more amino acid(s) in the amino acid sequence mentioned in SEQ ID NO:2 is/are deleted, substituted or added and the protein is characterized in having an ability of mediating the incorporation of any one of amino acids selected from a group consisting of leucine (Leu), isoleucine (Ile), phenylalanine (Phe), methionine (Met), tyrosine (Tyr), histidine (His), tryptophan (Trp) and valine (Val) in the cell in which the protein having the amino acid sequence mentioned in SEQ ID NO:6 is expressed.

Here "more amino acids" means plural amino acids. To be more specific, that is 1 to 40 amino acid(s), preferably 1 to 30 amino acid(s), more preferably 1 to 20 amino acid(s) and, particularly preferably, 1 to 10 amino acid(s).

A partial modification (deletion, substitution, insertion and addition) of the amino acid in the amino acid sequence of the protein of the present invention as mentioned above can be introduced by a partial modification of the base sequence coding for the protein. The partial modification of the base sequence can be introduced by a common method using a known site-specific mutagenesis (*Proc. Natl. Acad. Sci.*, USA, Vol. 81, p. 5662-5666, 1984).

The "partial amino acid sequence" in the present invention is an embodiment of the protein of the present invention as mentioned above and it means any partial amino acid sequence (protein fragment) in the amino acid sequence. Preferably, it is a partial sequence containing a site which is necessary for the protein of the present invention to achieve its biological function or a site where the protein of the present invention bonds to or interact with other protein molecule (receptor or ligand).

In addition, "polypeptide containing a partial amino acid sequence and having an antigenicity" in the present invention means a polypeptide containing the above-mentioned partial amino acid sequence and being recognized as a not-one's-own substance or a foreign substance due to the immune response mechanism of the mammal when the polypeptide is administered into the body of the above-mentioned mammal whereby production of an antibody to the polypeptide in the body of the mammal is possible.

The polypeptide containing the protein of the present invention or the partial amino acids in the amino acid sequence of the protein of the present invention can be expressed by an appropriate use of a method known in the technical field such as a chemical synthesis or a cell incubation method or a modified method thereof in addition to the genetic recombination technique which will be mentioned later.

It is also possible that the protein of the present invention is expressed by an injection of the RNA of the present invention which will be mentioned later into various cells such as oocytes of *Xenopus laevis* whereupon a direct translation of the RNA infused into the cells to the protein takes place without the transcription from DNA to mRNA (Special Issue of *Jikken Igaku*, "Method of Experiments of Biosignals", Vol. 11, No. 3, p. 30-38, 1993).

"DNA" of the present invention is that which is mentioned any of the above <7> to <11>. A preferred embodiment is the DNA which codes for the protein or the polypeptide of the present invention. DNA having any base sequence such as cDNA, DNA which is complementary to the cDNA and genomic DNA is covered as well so far as it is a DNA being able to code for the protein of the present invention. The DNA of the present invention further covers any DNA composed of any codon so far as the codon codes for the same amino acid. Further, one preferred embodiment of the DNA of the present invention is a DNA coding for the human-derived protein of the present invention.

More particularly, the DNA of the present invention is a DNA which is mentioned in any of the following (1) to (3).

(1) DNA which codes for the protein mentioned in any of the above <1> to <5>. Here, the DNA covers a DNA having any base sequence such as cDNA, DNA which is complementary to the cDNA and genomic DNA so far as it is a DNA coding for the protein such as a protein comprising the amino acid sequence mentioned in SEQ ID NO:2 or No:4.

(2) DNA which contains a base sequence comprising the base sequence which comprises a base sequence of 66th to 1586th bases in the base sequence mentioned in SEQ ID NO:1 and any one nonsense base sequence represented by TAG, TGA or TAA adjacent to the 1586th base or the base sequence of 64th to 1599th bases in the base sequence mentioned in SEQ ID NO:3 and any one nonsense base sequence represented by TAG, TGA or TAA adjacent to the 1599th base.

Here, "nonsense base sequence" is any of the base sequence of TAG, TGA or TAA which is also called termination codon, stop codon, nonsense codon, termination codon or termination signal and is a base sequence which codes for the termination point of the synthesis of protein.

(3) DNA which codes for the cell surface protein having an ability of mediating the incorporation of at least one amino acid into cell by hybridizing, under a stringent condition, to a DNA having a base sequence which comprises a base sequence of 66th to 1586th bases of the base sequence of SEQ ID NO:1 or a base sequence of 64th to 1599th bases of the base sequence of SEQ ID NO:3 and at least any one nonsense base sequence represented by TAG, TGA or TAA adjacent to the 1599th base where incorporation of the amino acid into cell is mediated without dependent upon the coexistence of any of the proteins of the following (a) and (b).

(a) protein having an amino acid sequence mentioned in SEQ ID NO:6 or NO:8; and (b) protein having an amino acid sequence mentioned in SEQ ID NO:6 or NO:8 where one or more amino acid(s) is/are deleted, substituted or added.

The term "more amino acids" used here has the same meaning as defined already.

The term "under a stringent condition" used here means a condition for carrying out the hybridization and, to be more specific, it means temperature and salt concentration.

The temperature is usually about 36° C. to about 42° C. and, depending upon the length and the degree of complementarily of the probe used, it may be also set as follows.

For example, when a probe having 50 or more bases is used and a hybridization is carried out under 0.9% NaCl, the aim of the temperature (Tm) giving a dissociation of 50% is calculated from the following formula and the temperature of hybridization can be set as shown in the following formula.

$$Tm=82.3° C.+0.41×(G+C)\%−500/n−0.61×(\text{formamide})\%$$

(n is a base number of the probe)
Temperature=Tm−25° C.

When a probe having 100 or more bases (G+C=40 to 50%) is used, the aim is that Tm changes according to the following (1) and (2).

(1) Tm lowers about 1° C. per 1% mismatch.
(2) Tm lowers at the rate of 0.6 to 0.7° C. per 1% formamide.

Accordingly, the temperature condition in the case of a combination of a completely complemented chains may be made as follows.

(A) 65 to 75° C. (when no formamide added)
(B) 35 to 45° C. (in the presence of 50% formamide)

The temperature condition in the case of a combination of incompletely complemented chains may be made as follows.

(A) 45 to 55° C. (when no formamide added)
(B) 35 to 42° C. (in the presence of 30% formamide)

The temperature condition when a probe having 23 or less bases may be made 37° C. or the following formula may be an aim.

$$\text{Temperature}=2° C.×(\text{numbers of } T+A)+4° C.×(\text{numbers of } G+C)−5° C.$$

With regard to a salt concentration, 5×SSC or equivalent thereto may be usually set.

Accordingly, the temperature in a hybridization in the present invention may, for example, be set at about 37° C. while the salt concentration may be set at 5×SSC or equivalent thereto.

The above-mentioned DNA of the present invention may be that which is prepared by any method. For example, complementary DNA (cDNA) prepared from mRNA, DNA prepared from genomic DNA, DNA obtained by chemical synthesis, DNA obtained by amplification by means of a PCR using RNA or DNA as a template and DNA which is constituted by an appropriate combination of those methods are included in the DNA of the present invention.

DNA which codes for the protein of the present invention may be prepared by a method where cDNA is cloned from mRNA of the protein of the present invention by a conventional method, a method where genomic DNA is isolated and subjected to splicing treatment, a chemical synthetic method, etc.

(1) For example, with regard to a method of cloning of cDNA from mRNA of the protein of the present invention, the following method is exemplified.

First, from the above-mentioned tissue or cell wherefrom the protein of the present invention is generated/produced, mRNA which codes for the protein of the present invention is prepared. Preparation of mRNA is carried out, for example, by a method where a whole RNA prepared by a known method such as a guanidine thiocyanate method (Chirgwin, et al., *Biochemistry*, Vol. 18, p. 5294, 1979), a hot phenol method or an AGPC method is subjected to an affinity chromatography using oligo(dT)cellulose or poly-U-Sepharose.

Then cDNA chain is synthesized by, for example, a known method such as that using a reverse transcriptase, e.g. a method by Okayama (*Mol. Cell Biol.*, Vol. 2, p. 161, 1982; and ibid., Vol. 3, p. 280, 1983), a method by Hoffman, et al. (*Gene*, Vol. 25, p. 263, 1983), etc. using the above-prepared mRNA as a template whereupon the cDNA is converted to a double-stranded cDNA. The resulting cDNA is integrated into a plasmid vector or a phage vector and, after *Escherichia coli* is transformed or subjected to an in vitro packaging, it is transfected into *E. coli* whereupon a cDNA library is prepared.

With regard to the plasmid vector used here, there is no particular limitation so far as it is duplicated and held in a host and, with regard to the phage vector used, anything which is able to proliferate in the host may be used. Examples of the vector for cloning which is usually applied are λZipLox, pUC19, λgt10 and λgt11. However, when subjecting to an immunological screening which will be mentioned later, a vector having a promoter which is able to express a gene coding for the protein of the present invention in a host is preferred.

With regard to a method for integration of cDNA into plasmid, an example is a method by Maniatis, et al. which is mentioned in *Molecular Cloning, A Laboratory Manual*, second edition, Cold Spring Harbor Laboratory, No. 1, p. 53, 1989. With regard to a method for integration of cDNA into phage vector, an example is a method by Hyunh, et al., *DNA Cloning, a Practical Approach*, Vol. 1, p. 49, 1985. To be more simple, a commercially available cloning kit (such as that manufactured by Gibco or Takara Shuzo) may be used as well. The recombined plasmid or phage vector prepared as such is introduced into an appropriate host in prokaryotic cells (such as *E. coli*.HB101, DH5α or MC1061/P3, etc.).

With regard to a method for the introduction of plasmid into a host, a calcium chloride method or a calcium chloride/rubidium chloride method mentioned in *Molecular Cloning, a Laboratory Manual*, second edition, Cold Spring Harbor Laboratory, No. 1, p. 74, 1989), an electroporation method, etc. may be exemplified. With regard to a method for the introduction of phage vector into a host, a method where phage DNA is subjected to an in vitro packaging and then introduced into a proliferated host may be exemplified. The in vitro packaging method may be easily carried out using a commercially available in vitro packaging kit (such as that manufactured by Stratagene, Amersham, etc.).

A method for the isolation of cDNA coding for the protein of the present invention from the cDNA library prepared by the above-mentioned method is carried out by a combination of common cDNA screening methods.

For example, a method where DNA which contains a part of or all of the base sequence coding for the amino acid sequence of the protein of the present invention or DNA which has a homology to the base sequence is prepared separately, this is labeled with $^{32}$P or [α-$^{32}$P]dCTP to prepare a probe and then a clone which contains the desired cDNA is screened by a known colony hybridization method (Crunstein, et al., *Proc. Natl. Acad. Sci.* USA, Vol. 72, p. 3961, 1975) or a plaque hybridization method (*Molecular Cloning, A Laboratory Manual*, second edition, Cold Spring Harbor Laboratory, No. 2, p. 108, 1989) and a method where a PCR primer is prepared, the specific region of the protein of the present invention is amplified by a PCR and the clone which has a DNA fragment coding for the region is selected, etc. may be exemplified.

When a cDNA library prepared by the vector which is able to express the cDNA (such as λZipLox or λgt11 phage vector) is used, a desired clone can be selected utilizing an antigen-antibody reaction using an antibody which has a reactivity with the protein of the present invention. When clone is treated in a large scale, it is preferred to use a screening method utilizing a PCR.

The base sequence of the DNA prepared as such can be determined by a method by Maxam-Gilbert (Maxam, et al., *Proc. Natl. Acad. Sci.* USA, Vol. 74, p. 560, 1977), a method where dideoxynucleotide synthetic chain is stopped using phage M13 (Sanger, et al., *Proc. Natl. Acad. Sci.* USA, Vol. 74, p.5463-5467, 1977) or a diterminator cycle sequencing method (manufactured by Applied Biosystems). The gene coding for the protein of the present invention can be prepared by a method where all or a part thereof is excised from the above-prepared clone using a restriction enzyme, etc.

(2) With regard to a method of preparation by isolating the DNA coding for the protein of the present invention from the genomic DNA derived from the cell expressing the protein of the present invention as mentioned above, the following method will be exemplified. Thus, the cell is dissolved preferably using SDS or protenase K, etc. and extraction with phenol is repeated whereby protein is removed from DNA. RNA is digested preferably by ribonuclease. The resulting DNA is partially digested by an appropriate restriction enzyme and the resulting DNA fragment is amplified by an appropriate phage or cosmid to prepare a library. A clone having a desired sequence is detected, for example, by a method where a radiolabeled DNA probe is used and all or a part of the gene coding for the protein of the present invention is excised from the clone by a restriction enzyme or the like and is collected.

(3) Manufacture of the cDNA coding for the protein having the amino acid sequence mentioned in SEQ ID NO:2 which is an embodiment of the DNA of the present invention can be carried out by a conventional method based upon a base sequence mentioned in SEQ ID NO:1.

For example, a rat C6 glioma cell is used as a gene source and mRNA (poly(A) RNA) is prepared therefrom. This is fractionated and each fraction is introduced into oocytes of *Xenopus laevis* together with the cRNA of 4F2hc.

Since cDNA of gene of 4F2hc has been reported already [Broer, et. al, *Biochem. J.*, Vol. 312, p. 863, 1995], it is possible to easily prepare the gene of 4F2hc from this sequence information using a PCR, etc. From the resulting cDNA of 4F2hc, it is possible to synthesize an RNA which is complementary thereto (cRNA) (capped one) using T3 or T7 RNA polymerase, etc.

With regard to the oocyte into which cRNA of 4F2hc and mRNA are introduced, transport (incorporation) of the substrate into the cell is measured using leucine or the like as a substrate and an mRNA fraction showing a high incorporation activity is selected whereby the mRNA of LAT1 can be concentrated. A cDNA library is prepared using this concentrated mRNA as a base. From the cDNA of the library, cRNA (capped one) is prepared where one group consists of about 500 clones and each group is introduced into oocytes together with cRNA of 4F2hc and, using the incorporation activity of the substrate as an index, a positive group is selected. When a positive group is found, it is further classified into subgroups and the same operation is repeated whereupon clones containing cDNA of LAT1 gene can be obtained.

With regard to the resulting cDNA, its base sequence is determined by a common method and a translation region is analyzed whereby the protein coded thereby or, in other words, the amino acid sequence of LAT1 can be determined.

The fact that the resulting cDNA is a cDNA of a neutral amino acid transporter gene or, in the other words, that the genetic product coded by the cDNA is a neutral amino acid transporter can, for example, be ascertained as follows. Thus, the cRNA prepared from the resulting cDNA of LAT1 gene is expressed by introducing into oocytes together with the cRNA of 4F2hc and the ability of transport (incorporation) of the neutral amino acid into the oocytes can be confirmed in the same manner as mentioned above by measuring the incorporation of the substrate into the oocytes according to a conventional incorporation test (Kanai and Hediger, *Nature*, 360, 467-471 (1992)) using an appropriate neutral amino acid as a substrate.

The same incorporation experiment is applied to the expressed cell whereby it is possible to investigate the characteristic of LAT1 such as the characteristic that LAT1 carries out an exchange of amino acids, a substrate specificity of LAT1, etc.

When the resulting cDNA of LAT1 gene is used and an appropriate cDNA library or genomic DNA library prepared from different gene sources is screened, it is possible to isolate the homologous gene, chromosomal gene, etc. derived from different tissues and different organisms.

Further, when a common PCR (polymerase chain reaction) is carried out using a synthetic primer designed based upon the information of the disclosed base sequence of the gene of the present invention (a base sequence shown in SEQ ID NO:1 or a part thereof), it is possible to isolate a gene from a cDNA library or a genomic DNA library.

SEQ ID NO:3 of the Sequence Listing which will be mentioned later shows a full-length cDNA base sequence (about 3.5 kbp) of gene of a neutral amino acid transporter (rat LAT1) derived from a rat C6 glioma cell line and an amino acid sequence (512 amino acids) of the protein coded to the translation region thereof. SEQ ID NO:4 of the Sequence Listing shows an amino acid sequence (512 amino acids) of a neutral amino acid transporter (rat LAT1) derived from a rat C6 glioma cell line.

A DNA library such as a cDNA library or a genomic DNA library can be prepared by a method mentioned, for example, in *Molecular Cloning* (by Sambrook, J., Fritsh, E. F. and Maniatis, T., published by Cold Spring Harbor Press in 1989). Alternatively, a commercially available library may be used if available.

In the preparation of a cDNA coding for the protein derived from human being, it can be also prepared by the following manner that a cosmid library into which human genomic DNA (chromosomal DNA, genomic DNA) is further introduced (*Laboratory Manual Human Genome Mapping*, edited by Masaaki Hori and Yusuke Nakamura, published by Maruzen) is prepared, then the cosmid library is screened to give a positive clone containing the DNA of the coding region of the desired protein and a coding DNA excised from the positive clone is used as a probe for carrying out a screening of the above-mentioned cDNA library.

SEQ ID NO:1 of the Sequence Listing which will be mentioned later shows a full-length cDNA base sequence (about 4.5 kbp) of the gene of a neutral amino acid transporter (human LAT1) derived from human being and an amino acid sequence (507 amino acids) of the protein coded to the translation region thereof. SEQ ID NO:2 of the Sequence Listing shows an amino acid sequence (507 amino acids) of a neutral amino acid transporter (human LAT1) derived from human being.

SEQ ID NO:5 of the Sequence Listing shows a full-length cDNA base sequence (about 1.8 kbp) of the gene of 4F2hc protein derived from human being and an amino acid sequence (529 amino acids) of the protein coded to the translation region thereof and SEQ ID NO:6 of the Sequence Listing shows an amino acid sequence (529 amino acids) of the 4F2hc protein derived from human being. SEQ ID NO:7 of the Sequence Listing shows a full-length cDNA base sequence (about 1.8 kbp) of the gene of 4F2hc protein derived from rat and an amino acid sequence (527 amino acids) of the protein coded to the translation region thereof and SEQ ID NO:8 of the Sequence Listing shows an amino acid sequence (527 amino acids) of the 4F2hc protein derived from rat.

"Expression vector" of the present invention means a recombinant vector containing the DNA of the present invention. There is no particular limitation for the recombinant vector of the present invention so far as it is able to conduct a self-multiplication in various hosts such as prokaryotic cells and/or eukaryotic cell including plasmid vector and phage vector.

In a simple manner, the recombinant vector can be prepared by linking the DNA of the present invention by a common method to a vector for recombination available in the art (plasmid DNA and bacteriophage DNA). Specific examples of the applicable vector for recombination in the case of plasmid derived from *Escherichia coli* are pBR322, pBR325, pUC12, pUC13 and pUC19; in the case of plasmid derived from yeast are pSH19 and pSH15; and in the case of plasmid derived from *Bacillus subtilis* are pUB110, pTP5 and pC194. Examples of the phage are bacteriophage such as λ phage and also animal and insect virus such as retrovirus, vaccinia virus and nuclear polyhedrosis virus (pVL 1393 manufactured by Invitrogen). Further example is pZL1.

For an object of expression of the protein of the present invention, expression vector is useful. With regard to an expression vector, there is no particular limitation therefor so far as it has an ability of expressing the protein of the present invention in various host cells of prokaryotic cells and/or eukaryotic cells. For example, pMAL C2, pEF-BOS (*Nucleic Acid Research*, Vol. 18, p. 5322, 1990; etc.) or pME18S (*Handbook of Genetic Engineering*, Supplementary Issue of *Jikken Igaku*, 1992; etc.) may be exemplified.

When bacteria, particularly *Escherichia coli*, are used as a host cell, an expression vector is usually constituted at least from promoter-operator region, initiation codon, DNA coding for the protein of the present invention, termination codon, terminator region and replicable unit.

When yeast, animal cell or insect cell is used as a host, it is preferred that an expression vector contains at least promoter, initiation codon, DNA coding for the protein of the present invention and termination codon. It may further contain DNA coding for a signal peptide, enhancer sequence, non-translated region on 5'- and 3'-sides of the gene coding for the protein of the present invention, splicing conjugated part, polyadenylation site, selective marker region or duplicable unit. Depending upon an object, it may also contain gene for gene amplification (marker) which is commonly used.

Promoter-operator region for expressing the protein of the present invention in bacteria contains promoter, operator and Shine-Dalgarno (SD) sequence (such as AAGG). When the host is a bacterium of genus *Escherichia*, appropriate examples are those which contain Trp promoter, lac promoter, rec A promoter, λPL promoter, lpp promoter and tac promoter. Examples of the promoter for expressing the protein of the present invention in yeast are PH05 promoter, PGK promoter, GAP promoter and ADH promoter and, when the host belongs to genus *Bacillus*, the examples are SL01 promoter, SP02 promoter and penP promoter. When the host is a eukaryotic cell such as a mammalian cell, its examples are promoter derived from SV40, promoter for retrovirus and heat shock promoter. Preferred examples are SV-40 and retrovirus. However, there is no particular limitation to the above. Utilization of enhancer is an effective method for the expression as well.

With regard to the suitable initiation codon, methionine codon (ATG) is exemplified.

With regard to the termination codon, commonly used termination codons (such as TAG, TGA and TAA) are exemplified.

With regard to the terminator region, commonly used natural or synthetic terminator may be used.

Duplicable unit means the DNA having an ability of being able to duplicate its total DNA sequence in host cells and includes natural plasmid, artificially modified plasmid (DNA fragment prepared from natural plasmid) and synthetic plasmid. With regard to a suitable plasmid, plasmid pBR322 or artificially modified product thereof (DNA fragment obtained by treating pBR322 with an appropriate restriction enzyme) in the case of *E. coli*, yeast 2µ plasmid or yeast chromosomal DNA in the case of yeast; and plasmid pRS-Vneo (ATCC 37198), plasmid pSV2dhfr (ATCC 37145), plasmid pdBPV-MMTneo (ATCC 37224), plasmid pSV2neo (ATCC 37149), etc. in the case of mammalian cells.

With regard to the enhancer sequence, polyadenylation site and splicing combination site, those which are commonly used by the persons skilled in the art such as each of those derived from SV40 may be used.

With regard to the selective marker, those which are commonly used may be used by a conventional method. For example, gene which is resistant to antibiotics such as tetracycline, ampicillin, neomycin or kanamycin is exemplified.

With regard to the gene for a gene amplification, dihydrofolic acid reductase (DHFR) gene, thymidinekinase gene, neomycin-resistant gene, glutamic acid-synthetic enzyme gene, adenosinedeaminase gene, ornithinedecarboxylase gene, hygromycin B phosphotransferase gene, aspartate transcarbamylase, etc. are exemplified.

The expression vector of the present invention can be prepared by continuously and cyclically linking at least the above-mentioned promoter, initiation codon, DNA coding for the protein of the present invention, termination codon and terminator region to an appropriately duplicable unit. If necessary in that case, it is also possible to use an appropriate DNA fragment (such as linker, other restriction site, etc.) by a common method such as digestion with a restriction enzyme or ligation using a T4 DNA ligase.

The "transformed cell" of the present invention is a cell which is transformed by the above-mentioned expression vector or DNA of the present invention and can be prepared by introducing the DNA or expression vector into prokaryotic cell or eukaryotic cell as a host cell.

With regard to the host cell used in the present invention, there is no particular limitation so far as it is adapted to the above-mentioned expression vector and is able to be transformed and its examples are various cells such as natural cell or artificially established recombinant cell which are commonly used in the technical field of the present invention such as bacteria (belonging to genus *Escherichia* and genus *Bacillus*), yeast (belonging to genus *Saccharomyces*, genus *Pichia*, etc.), animal cells and insect cells.

Preferably, it is *Escherichia coli* or animal cells and, to be more specific, *E. coli* (DH5α, TB1, HB101, etc.), mouse-derived cells (COP, L, C127, Sp2/0, NS-1 and NIH3T3, etc.), rat-derived cells (PC12, PC12h, etc.), hamster-derived cells (BHK and CHO, etc.), monkey-derived cells (COS1, COS3, COS7, CV1 and Velo, etc.) and human-derived cells (HeLa, cells derived from diploid fibroblast, HEK293 cells, myeloma cells and Namalwa, etc.) may be exemplified.

Introduction of expression vector into host cells (transformation (character transfer)) may be carried out by a method which has been known already.

Thus, the transformation can be carried out, for example, by a method of Cohen, et al. (*Proc. Natl. Acad. Sci.* USA, Vol. 69, p. 2110, 1972), a protoplast method (*Mol. Gen. Genet.*, Vol. 168, p. 111, 1979) and a competent method (*J. Mol. Biol.*, Vol. 56, p. 209, 1971) in the case of bacteria (*Escherichia coli*, *Bacillus subtilis*, etc.); for example, by a method of Hinnen, et al. (*Proc. Natl. Acad. Sci.* USA, Vol. 75, p. 1927, 1978) and a lithium method (*J. Bacteriol.*, Vol. 153, p. 163, 1983) in the case of *Saccharomyces cerevisiae*; for example, by a method of Graham (*Virology*, Vol. 52, p. 456, 1973) in the case of animal cells; and, for example, by a method of Summers, et al. (*Mol. Cell. Biol.*, Vol. 3, p. 2156-2165, 1983) in the case of insect cell; respectively.

The "protein" of the present invention can be expressed by incubation of the above-prepared transformant cell (hereinafter, this will be used in a sense of covering the substance into which the character is transferred) containing the expression vector in a nutritive medium.

It is preferred that the nutritive medium contains carbon source, inorganic nitrogen source or organic nitrogen source necessary for the growth of the host cell (transformant). With regard to the carbon source, glucose, dextran, soluble starch, sucrose, etc. may be exemplified; and with regard to the inorganic nitrogen source or an organic nitrogen source, ammonium salts, nitrates, amino acid, corn steep liquor, peptone, casein, meat extract, soybean cake, potato extract, etc. may be exemplified. If desired, other nutrients (such as inorganic salt [e.g., calcium chloride, sodium dihydrogen phosphate and magnesium chloride], vitamins, antibiotic substances [e.g., tetracycline, neomycin, ampicillin and kanamycin], etc.) may be contained therein.

The incubation may be carried out by a method which has been known in the art. The incubating conditions such as temperature, pH of the medium and incubating time may be appropriately selected so as to abundantly express the protein of the present invention.

As hereunder, the specific media and incubating conditions which are used depending upon the host cell will be exemplified although the present invention is not limited thereto at all.

When the host is bacteria, *Actinomyces*, yeast or filamentous fungi, a liquid medium containing the above-mentioned nutrients is appropriate for example. Preferably, it is a medium where the pH is 5-8.

When the host is *E. coli*, examples of the preferred medium are LB medium, M9 medium (Miller, et al., *Exp. Mol. Genet.*, Cold Spring Harbor Laboratory, p. 431, 1972), etc. In that case, the incubation may be carried out usually at 14-43° C. for about 3-24 hours together, if necessary, with aeration and stirring.

When the host is genus *Bacillus*, the incubation may be carried out usually at 30-40° C. for about 16-96 hours, if necessary, with aeration and stirring.

When the host is yeast, it is preferred that the medium is, for example, a Burkholder minimum medium (Bostian, *Proc. Natl. Acad. Sci.* USA, Vol. 77, p. 4505, 1980) and the pH is preferably 5-8. Incubation is carried out usually at about 20-35° C. for about 14-144 hours and, if necessary, aeration and stirring may be conducted.

When the host is animal cells, MEM medium containing about 5-20% of bovine fetus serum (*Science*, Vol. 122, p. 501, 1952), DMEM medium (*Virology*, Vol. 8, p. 396, 1959), RPMI 1640 medium (*J. Am. Med. Assoc.*, Vol. 199, p. 519, 1967), 199 medium (*Proc. Soc. Exp. Biol. Med.*, Vol. 73, p.1, 1950), etc. may be used as a medium. The pH of the medium is preferably about 6-8 and the incubation is carried out usually at about 30-40° C. for about 15-72 hours. If necessary, aeration and stirring may be conducted as well.

When the host is insect cells, Grace's medium containing bovine fetus serum (*Proc. Natl. Acad. Sci.* USA, Vol. 82, p. 8404, 1985), etc. may be used for example and its pH is preferably about 5-8. The incubation is carried out usually at about 20-40° C. for about 15-100 hours and, if necessary, aeration and stirring may be conducted as well.

The protein of the present invention can be expressed by such a manner that the transformant which is prepared as above using the expression vector or the DNA of the present invention as mentioned above is incubated under the above-mentioned incubating condition.

When the protein of the present invention is prepared as a soluble protein, the cells are collected after the cell incubation and suspended in an appropriate buffer solution and, after the cell walls and/or cell membranes of the cell, etc. are destroyed by, for example, means of ultrasonic wave, lysozyme, freeze-thaw, etc., a method such as centrifugation, filtration, etc. is carried out whereupon the membrane fraction containing the protein of the present invention is obtained. The membrane fraction is solubilized using a surface-active agent such as Triton-X 100 to give a crude solution. The crude solution is subjected to a commonly used purifying method so as to purify and isolate the protein whereupon the protein of the present invention can be isolated as a soluble protein.

With regard to a method for isolation and for purification, there may be exemplified a method where the solubility is utilized such as salting-out and solvent precipitation methods; a method where the difference in molecular weights is utilized such as dialysis, ultrafiltration, gel filtration and a sodium dodecylsulfate-polyacrylamide gel electrophoresis method; a method where the charge is utilized such as ion exchange chromatography and hydroxylapatite chromatography; a method where the specific affinity is utilized such as affinity chromatography; a method where the difference in hydrophobicity is utilized such as a reversed phase high-performance chromatography; and a method where the difference in isoelectric points is utilized such as isoelectric focusing.

The "RNA" of the present invention is an RNA which is mentioned in the above <5> and will be mentioned later.

"an RNA which contains a base sequence of base numbers of from 1st to 1521st of the base sequence mentioned in SEQ ID NO:26 and a base sequence comprising any of one nonsense base sequence represented by UAG, UGA or UAA adjacent to the base of the base number of 1521st"

Here, the term "nonsense base sequence" means any of the base sequences of UAG, UGA and UAA which is also called termination codon, stop codon, nonsense codon, termination codon or termination signal and is a base sequence coding for the termination point of the translation to the protein.

The RNA of the present invention can be prepared by a common method using a commercially available RNA polymerase (such as T7 RNA polymerase) using a DNA sequence complementary to the DNA mentioned in the above <1>, i.e. "DNA which contains a base sequence of from 66th to 1586th bases of the base sequence mentioned in SEQ ID NO:1 and any one of the nonsense base sequences of TAG, TGA and TAA adjacent to the 1586th base" as a template.

The RNA of the present invention can be used for expressing the protein of the present invention in various cells. Thus, when the RNA of the present invention is injected into oocytes of *Xenopus laevis*, it is possible to directly express the protein of the present invention in the cells from the injected RNA without a transcription from DNA to mRNA (Special Issue of *Jikken Igaku*, "Method of Experiments of Biosignals", Vol. 11, No. 3, p. 30-38, 1993).

Another feature of the present invention is the DNA as mentioned in the above <4> which will be given as follows.

"DNA which contains a partial base sequence in the base sequence mentioned in SEQ ID NO:1 or DNA where a part of the DNA is chemically modified, or DNA which contains a base sequence which is complementary to the partial base sequence or DNA where a part of the DNA is chemically modified and has the following characteristics (1) and (2).

(1) the partial base sequence is a base sequence which is not so completely identical with the partial base sequence of the base sequence mentioned in SEQ ID NO:3; and (2) the DNA or the chemically modified DNA hybridizes to the gene coding for the protein having an amino acid sequence mentioned in SEQ ID NO:2.

Here, "a partial base sequence in the base sequence mentioned in SEQ ID NO:1" means a partial base sequence comprising optional numbers of base in any site contained in the base sequence mentioned in SEQ ID NO:1".

The DNA is useful as a probe in an operation of a DNA hybridization or an RNA hybridization. In an object of using the DNA as a probe, there may be exemplified a partial base sequence of continuous 20 or more bases, preferably a partial base sequence of continuous 50 or more bases, more preferably a partial base sequence of continuous 100 or more bases, still more preferably a partial base sequence of continuous 200 or more bases and, particularly preferably, a partial base sequence of continuous 300 or more bases as the partial base sequence.

The above-mentioned DNA is also useful as a primer in a PCR. In an object of using the DNA as a primer in a PCR, there may be exemplified a partial base sequence of continuous 5 to 100 bases, preferably a partial base sequence of continuous 5 to 70 bases, more preferably a partial base sequence of continuous 5 to 50 bases and, still more preferably, a partial base sequence of continuous 5 to 30 bases as the partial base sequence.

Further, the above-mentioned DNA is useful as an antisense pharmaceutical agent as well. Thus, the DNA hybridizes to the RNA or the DNA coding for the protein having an amino acid sequence mentioned in SEQ ID NO:2 whereby transcription of the DNA to mRNA or translation of the mRNA to protein can be inhibited as well.

In an object of using the above DNA as an antisense pharmaceutical agent, there may be exemplified a partial base sequence of continuous 5 to 100 bases, preferably a partial base sequence of continuous 5 to 70 bases, more preferably a partial base sequence of continuous 5 to 50 bases and, still more preferably, a partial base sequence of continuous 5 to 30 bases as the partial base sequence.

When the DNA is used as an antisense pharmaceutical, it is possible to subject a part of the base sequence of the DNA to a chemical modification so as to increase its half life (stability) in blood when the DNA is administered into the body of a patient, to increase a permeability in the intracellular membrane, to increase the resistance to decomposition in or the absorption with a digestive organs in the case of an oral administration, etc. With regard to the chemical modification, that of a phosphoric acid bond in the oligonucleotide structure, ribose, nucleic acid base, saccharide site, 3'- and/or 5'-terminal(s), etc. may be exemplified.

With regard to a modification of the phosphoric acid bond, a change of one or more the bond(s) to any of phosphodiester bond (D-oligo), phosphorothioate bond, phosphorodithioate bond (S-oligo), methyl phosphate bond (MP-oligo), phosphoroamidate bond, non-phosphoric acid bond and methyl phosphonothioate or to a combination thereof may be given. With regard to a modification of ribose, a change to 2'-fluororibose, to 2'-O-methylribose, etc. may be given. With regard to a modification of nucleic acid base, a change to 5-propynyluracil, to 2-aminoadenine, etc. may be given.

Another feature of the present invention is the RNA mentioned in the above <6> which will be as follows.

"an RNA containing a partial base sequence in the base sequence of RNA having a base sequence complementary to the base sequence mentioned in SEQ ID NO:26 or an RNA in which a part of the RNA is chemically modified, wherein the RNA or the chemically modified RNA is characterized in hybridizing to an RNA which codes for the protein having an amino acid sequence mentioned in SEQ ID NO:2"

Here, "partial base sequence" means a partial base sequence comprising any numbers of bases at any site.

The above-mentioned RNA is useful as an antisense pharmaceutical agent, as well. Thus, the RNA hybridizes to the RNA or the DNA coding for the protein having an amino acid sequence mentioned in SEQ ID NO:2 whereby transcription of the DNA to mRNA or translation of the mRNA to protein can be inhibited.

In an object of using the above RNA as an antisense pharmaceutical agent, there may be exemplified a partial base sequence of continuous 5 to 100 bases, preferably a partial base sequence of continuous 5 to 70 bases, more preferably a partial base sequence of continuous 5 to 50 bases and, still more preferably, a partial base sequence of continuous 5 to 30 bases as the partial base sequence.

When the RNA is used as an antisense pharmaceutical agent, it is possible to subject a part of the base sequence of the RNA to a chemical modification so as to increase its half life in blood when the RNA is administered into the body of a patient, to increase a permeability in the intracellular membrane, to increase the resistance to decomposition in or the absorption with a digestive organs in the case of an oral administration, etc. With regard to the chemical modification, that which is applied to the above-mentioned antisense DNA may be exemplified.

The "antibody" of the present invention is a polyclonal antibody (antiserum) or a monoclonal antibody and, preferably, a monoclonal antibody.

To be more specific, it is an antibody having a reactivity with the protein of the present invention or a part thereof.

The "antibody" of the present invention covers an antibody of a natural type which is prepared by immunizing non-human mammal such as mouse, rat, hamster, guinea pig, chicken, rabbit, goat, sheep, etc. by a conventional method using the protein of the present invention or a part thereof (including natural substance, recombinant and chemically synthesized substance) or the cells in which the protein is expressed (regardless of natural cell, transformant cell, normal cell, tumor cell, etc.) as immunogen (antigen); a recombinant chimera monoclonal antibody and recombinant human-type monoclonal antibody (CDR-grafted antibody) which can be manufactured by means of genetic recombination technique; and a human antibody which can be manufactured using human antibody-producible transgenic animal, etc.

In the case of a monoclonal antibody, there is covered a monoclonal antibody having any isotype such as IgG, IgM, IgA, IgD and IgE. Preferably, it is IgG or IgM.

The polyclonal antibody (antiserum) and the monoclonal antibody of the present invention can be manufactured by the already-known general manufacturing methods.

Thus, for example, the above-mentioned immunogen (antigen) is immunized to mammal, preferably to mouse, rat, hamster, guinea pig, rabbit, chicken, cat, dog, pig, goat, horse or cattle or, more preferably, to mouse, rat, hamster, guinea pig or rabbit together, if necessary, with a Freund's adjuvant.

The polyclonal antibody (antiserum) can be prepared from the serum obtained from the immunologically sensitized animal.

The monoclonal antibody can be manufactured in such a manner that a hybridoma is prepared from the antibody-producing cell (spleen, lymph node, bone marrow or tonsil; preferably, B cell of spleen) obtained from the immunologically sensitized animal with a cell of a bone marrow type (myeloma cell) having no ability of autoantibody production, the hybridoma is cloned and a clone which produces a monoclonal antibody showing a specific affinity to the antigen used for immunization of mammal is selected by an immunological measuring method (such as ELISA).

To be more specific, the monoclonal antibody can be manufactured as follows. Thus, the protein of the present invention or a part thereof (including natural substance, recombinant and chemically synthesized substance) or cell wherein the protein is expressed (regardless of natural cell, transformant cell, normal cell or tumor cell) is used as an immunogen and the immunogen is injected, once or several times, or transplanted to mouse, rat, hamster, guinea pig, chicken or rabbit or, preferably, to mouse, rat or hamster (including a transgenic animal which is prepared so as to produce an antibody derived from other animal such as human antibody-producing transgenic mouse) subcutaneously, intramuscularly, intravenously, into hood pad or intraperitoneally whereupon an immunological sensitization is carried out together, if necessary, with a Freund's adjuvant. Usually, one to four immunization(s) is/are carried out every 1 to 14 day(s) from the initial immunization and antibody-producing cells can be obtained from the mammal which is immunologically sensitized for about 1 to 5 day(s) from the final immunization.

Preparation of a hybridoma secreting a monoclonal antibody can be carried out by a modifying method of Köhler and Milstein (*Nature*, Vol. 256, p. 495-497, 1975) or by a method similar thereto.

Thus, it can be prepared by a cell fusion of antibody-producing cells contained in spleen, lymph node, bone marrow or tonsil or, preferably, in spleen obtained from immunologically sensitized mammal as above with myeloma cells having no ability of autoantibody production derived from mammal such as, preferably, mouse, rat, guinea pig, hamster, rabbit or human being or, more preferably, mouse, rat or human being.

With regard to the myeloma cells used for the cell fusion, it is possible to use, for example, mouse-derived myeloma P3/X63-AG8.653 (653; ATCC No. CRL 1580), P3/NSI/1-Ag4-1 (NS-I), P3/X63-Ag8.U1 (P3U1), SP2/0-Ag14 (Sp2/0, Sp2), PAI, F0 or BW5147; rat-derived myeloma 210RCY3-Ag.2.3.; and human-derived myeloma U-266AR1, GM1500-6TG-A1-2, UC729-6, CEM-AGR, D1R11 or CEM-T15.

Screening of hybridoma clone producing the monoclonal antibody is carried out by incubating the hybridoma in, for example, a microtiter plate and by measuring the reactivity of the incubated supernatant liquid of the well where the growth is noted to immunized antigen used in the above immunological sensitization of mouse by means of an enzyme immunoassay such as RIA or ELISA.

Manufacture of a monoclonal antibody from a hybridoma can be carried out either in vitro or in vivo in the peritoneal effusion of mouse, rat, guinea pig, hamster or rabbit, preferably in mouse or rat or, more preferably, in mouse followed by isolating from the resulting incubated supernatant liquid or peritoneal effusion of the mammal.

When an incubation in vitro is carried out, it is possible to carry out in such a manner that the hybridoma is proliferated, maintained and stored depending upon the various conditions such as characteristic of the cell species to be incubated, object of the test study, method of incubation, etc. and the known nutrient medium to be used for the production of a monoclonal antibody in the supernatant fluid of the culture liquid or every nutrient medium induced and prepared from a known basal medium is used.

With regard to a basal medium, a low-calcium medium such as Ham F12 medium, MCDB153 medium or low-calcium MEM medium; a high-calcium medium such as MCDB104 medium, MEM medium, D-MEM medium, RPMI 1640 medium, ASF104 medium or RD medium; etc. may be exemplified. Depending upon the object, the basal medium may contain serum, hormone, cytokine and/or various inorganic or organic substances.

Isolation and purification of the monoclonal antibody can be carried out, for example, by subjecting the above-mentioned incubated supernatant liquid or peritoneal effusion to saturated ammonium sulfate euglobulin precipitating method, caproic acid method, caprylic acid method, ion-exchange chromatography (DEAE, DE52, etc.), affinity column chromatography using anti-immunoglobulin column, protein A column, etc. and the like.

It is also possible that the gene coding for the monoclonal antibody is cloned from the hybridoma, transgenic cow, goat, sheep or pig where the antibody coding gene is integrated in an intrinsic gene is prepared by means of a transgenic animal preparing technique and, from the milk of the transgenic animal, the monoclonal antibody derived from the antibody gene is obtained in a large amount (*Nikkei Science*, issue of April 1997, p. 78-84).

The "recombinant chimera monoclonal antibody" of the present invention is a monoclonal antibody which is prepared by a genetic engineering means and, to be more specific, it means a chimera monoclonal antibody such as mouse/human chimera monoclonal antibody, characterized in that for example, its variable region is that which is derived from mouse immunoglobulin while its constant region is that which is derived from human immunoglobulin.

The constant region derived from human immunoglobulin has its own amino acid sequence depending upon the isotypes of IgG, IgM, IgA, IgD and IgE and the constant region of the recombinant chimera monoclonal antibody in the present invention may be a constant region of human immunoglobulin belonging to any isotype. Preferably, it is a constant region of human IgG.

The chimera monoclonal antibody of the present invention may, for example, be manufactured as follows. It goes without saying however that the manufacture is not limited to such a method only.

For example, a mouse/human chimera monoclonal antibody can be prepared by referring to *Jikken Igaku* (Special Issue), Vol. 16, No. 10, 1988 and Japanese Patent Publication No. 73280/1991.

Thus, $C_H$ gene (C gene coding for H chain constant region) obtained from DNA coding for human immunoglobulin is arranged in an expressible manner to the downstream of active $V_H$ gene (rearranged VDJ gene coding for H chain variable region) obtained from DNA coding for a mouse monoclonal antibody isolated from a hybridoma which produces the mouse monoclonal antibody or $C_L$ gene (C gene coding for L chain constant region) obtained from DNA coding for human immunoglobulin is arranged in an expressible manner to downstream of active $V_L$ gene (rearranged VJ gene coding for L chain variable region) obtained from DNA coding for a mouse monoclonal antibody isolated from the hybridoma whereby it is inserted into one or separate expression vector(s), host cell is transformed by the expression vector and the transformed cell is incubated to prepare an aimed one.

To be more specific, DNA is extracted from a mouse monoclonal antibody-producing hybridoma by a common method and the DNA is digested by an appropriate restriction enzyme (such as EcoRI, Hind III, etc.), subjected to an electrophoresis (using a 0.7% agarose gel for example) and subjected to a southern blotting. The migrated gel is stained by ethidium bromide for example and photographed, position of the marker is marked and the gel is washed with water twice and dipped in a 0.25M HCl solution for 15 minutes. Then, it is dipped in a 0.4N NaOH solution for 10 minutes and, during that period, it is gently shaken. It is transferred to a filter by a common method and, after 4 hours, the filter is recovered and washed with 2×SSC twice. After the filter is well dried, it is subjected to a baking (75° C. for 3 hours). After completion of the baking, the filter is placed in a 0.1×SSC/0.1% SDS solution and treated at 65° C. for 30 minutes. Then it is dipped in a 3×SSC/0.1% SDS solution. The resulting filter is placed in a vinyl bag together with a prehybridization solution and treated at 65° C. for 3-4 hours.

Then a probe DNA labeled with $^{32}P$ and a hybridization solution are placed therein and made to react at 65° C. for around 12 hours. After completion of the hybridization, the filter is washed under appropriate salt concentration, reaction temperature and time (e.g., 2×SSC-0.1% SDS solution at room temperature for 10 minutes). The filter is placed in a vinyl bag and a small amount of 2×SSC is added, tightly sealed and subjected to an autoradiography.

Rearranged VDJ gene and VJ gene coding for H chain and L chain of the mouse monoclonal antibody, respectively, are identified by the above-mentioned southern blotting. The region containing the identified DNA fragments is fractionated by a sucrose density gradient centrifugation, integrated into a phage vector (such as Charon 4A, Charon 28, λEMBL3, λEMBL4, etc.) and *Escherichia coli* (such as LE392, NM539, etc.) is transformed by the phage vector to prepare a genome library. The genome library is subjected to a plaque hybridization using an appropriate probe (H chain J gene, L chain (κ) J gene, etc.) according to, for example, a Benton-Davis method (*Science*, Vol. 196, p. 180-182, 1977) to prepare a positive clone containing each rearranged VDJ gene and VJ gene. A restriction enzyme map of the resulting clone is prepared and a base sequence is determined whereupon it is confirmed that a gene containing the aimed rearranged $V_H$ (VDI) gene or $V_L$ (VI) gene is obtained.

In the meanwhile, human $C_H$ gene and human $C_L$ gene each for the preparation of chimera is isolated separately. For example, in the manufacture of a chimeric antibody with human IgG1, $C\gamma_1$ gene which is a $C_H$ gene and Cκ gene which is a $C_L$ gene are isolated. Utilizing the high homology in base sequence of mouse immunoglobulin gene with human immunoglobulin gene, those genes can be obtained by isolating from human genome library using mouse $C\gamma_1$ gene and mouse Cκ gene corresponding to human $C\gamma_1$ gene and human Cκ gene as probes.

To be more specific for example, DNA fragment containing human Cκ gene and holding an enhancer region is isolated from human lambda Charon 4A HaeIII-AluI genome library (Cell, Vol. 15, p. 1157-1174, 1978) using Hind III-BamHI fragment of 3 kb from clone Ig 146 (Proc. Natl. Acad. Sci. USA, Vol. 75, p. 4709-4713, 1978) and EcoRI fragment of 6.8 kb from clone MEP 10 (Proc. Natl. Acad. Sci. USA, Vol. 78, p. 474-478, 1981) as probes. In addition, for example, human fetal hepatic cell DNA is cleaved by Hind III and fractionated by an agarose gel electrophoresis, a band of 5.9 kb is inserted into λ788 and the above-mentioned probe is used whereupon human Cγ gene is isolated.

Using the mouse $V_H$ gene and the mouse $V_L$ gene and also the human $C_H$ gene and the human $C_L$ gene isolated as such, the human $C_H$ gene to the downstream of the mouse $V_H$ gene or the human $C_L$ gene to the downstream of the mouse $V_L$ gene is integrated to an expression vector such as pSV2gpt or pSV2neo using an appropriate restriction enzyme and DNA ligase according to a conventional method taking the promoter region and the enhancer region, etc. into consideration. At that time, chimera genes of mouse $V_H$ gene/ human $C_H$ gene and mouse $V_L$ gene/human $C_L$ gene may be arranged in one expression vector at the same time or may be arranged in each separate expression vector.

The expression vector into which chimera gene is inserted prepared as such is introduced into a bone marrow cell which does not produce antibody by itself such as P3X63.Ag8.653 cell or SP210 cell by means of a protoplast fusion method, a DEAE-dextran method, a calcium phosphate method or an electroporation method. The transformed cell is selected by incubation in a medium containing a pharmaceutical agent corresponding to the pharmaceutical-resistant gene introduced into the expression vector whereupon the aimed chimera monoclonal antibody-producing cell is obtained.

A desired chimera monoclonal antibody is prepared from the supernatant fluid of the incubated antibody-producing cell selected as such.

The "human type antibody (CDR-grafted antibody) of the present invention is a monoclonal antibody which is prepared by a genetic engineering means and, to be more specific, it means a human type monoclonal antibody which is characterized in that a part of or all of the complementarity-determining region of its hypervariable region is a complementarity-determining region of the hypervariable region derived from the mouse monoclonal antibody, that a frame region of its variable region is a frame region of the variable region derived from human immunoglobulin and that its constant region is a constant region derived from human immunoglobulin.

Here, the complementarity-determining region of the hypervariable region means three regions (complementarity-determining residues: CDR1, CDR2 and CDR3) which are present in the hypervariable region of the variable region in the antibody and are the sites directly bonding to the antigen complementarily while a frame region of the variable region means the relatively conserved four regions (frameworks: FR1, FR2, FR3 and FR4) intervening before and after the three complementarity-determining regions.

In other words, all regions which are other than a part of or all of the complementarity-determining region of hypervariable region of mouse monoclonal antibody for example mean a monoclonal antibody which is substituted for the corresponding region of human immunoglobulin.

A constant region derived from human immunoglobulin has each specific amino acid sequence by an isotype of IgG, IgM, IgA, IgD and IgE and the constant region of a human-type monoclonal antibody in the present invention may be a constant region of human immunoglobulin belonging to any of the isotypes. Preferably, it is a constant region of human IgG. There is no limitation for the frame region of the variable region derived from human immunoglobulin as well.

The human-type monoclonal antibody of the present invention can be manufactured, for example, as follows although it goes without saying that the manufacture is not limited to such a manufacturing method only.

For example, a recombinant human-type monoclonal antibody derived from mouse monoclonal antibody can be prepared by a genetic engineering means by referring to JP-W-4-506458 and Japanese Patent Laid-Open No. 296890/1987.

Thus, at least one mouse H chain CDR gene and at least one mouse L chain CDR gene corresponding to the mouse H chain CDR gene are isolated from a hybridoma which produces a mouse monoclonal antibody while, from human immunoglobulin gene, a human H chain gene coding for whole regions except the human H chain CDR corresponding to the above mouse H chain CDR and a human L chain gene coding for all regions except the human L chain CDR corresponding to the above mouse L chain CDR are isolated.

The mouse H chain CDR gene and the human H chain gene isolated as such are introduced into an appropriate expression vector in an expressible manner while, in a similar way, the mouse L chain CDR gene and the human L chain gene are introduced into another appropriate expression vector in an expressible manner. Alternatively, it is also possible that the mouse H chain CDR gene/human H chain gene and mouse L chain CDR gene/human L chain gene are introduced into the same expression vector in an expressible manner. When a host cell is transformed by the expression vector prepared as such, a transformed cell which is able to produce a human-type monoclonal antibody is obtained and, when the transformed cell is incubated, an aimed human-type monoclonal antibody is obtained from the incubated supernatant liquid.

The "human antibody" of the present invention is an immunoglobulin derived from the gene in which all regions including variable region of H chain and constant region of H chain and variable region of L chain and constant region of L chain constituting immunoglobulin code for human immunoglobulin.

The human antibody can be manufactured in the same manner as in the above-mentioned method for the manufacture of polyclonal antibody or monoclonal antibody by a conventional method such as that a transgenic animal prepared by incorporation of at least human immunoglobulin gene into locus of mammal except human being such as mouse is subjected to an immunological sensitization with antigen.

For example, a transgenic mouse which produces human antibody can be prepared by a method mentioned in *Nature Genetics*, Vol. 15, p. 146-156, 1997; *Nature Genetics*, Vol. 7, p. 13-21, 1994; JP-W-4-504365; International Patent Laid-Open No. WO 94/25585; *Nikkei Science*, issue of June, p. 40-50, 1995; *Nature*, Vol. 368, p. 856-859, 1994; and JP-W-6-500233.

"A part of the antibody" in the present invention means a part of the region of the above-mentioned antibody or, preferably, the monoclonal antibody of the present invention and, to be more specific, it is F(ab')$_2$, Fab', Fab, Fv (variable fragment of antibody), sFv, dsFv (disulphide stabilised Fv) or dAb (single domain antibody) (*Exp. Opin. Ther. Patents*, Vol. 6, No. 5, p. 441-456, 1996).

Here, "F(ab')$_2$" and "Fab" are the antibody fragments which are manufactured by the treatment of immunoglobulin (monoclonal antibody) with a protease such as pepsin or papain and is produced by digestion before and after the disulfide bond existing between the two H chains in a hinge region. For example, when IgG is treated with papain, it is cleaved at the upstream of the disulfide bond existing between the two H chains in the hinge region to manufacture two homologous antibody fragments where L chain consisting of $V_L$ (L chain variable region) and $C_L$ (L chain constant region) and H chain fragment consisting of $V_H$ (H chain variable region) and CHγ1 (γ1 region in H chain constant region) are bonded by a disulfide bond at the C terminal region. Each of those two homologous antibody fragments is called Fab'.

When IgG is treated with pepsin, it is cleaved at the downstream of a disulfide bond existing between two H chains in a hinge region to manufacture an antibody fragment where the above two Fab' are bonded in a hinge region and the size is a bit larger than the above. This antibody fragment is called F(ab')$_2$.

The "monoclonal antibody-producing cell" of the present invention means any cell which produces the above-mentioned monoclonal antibody of the present invention. To be more specific, it is a cell mentioned in any of the following (1) to (3).

(1) The monoclonal antibody-producing B cell derived from non-human mammal which produces the protein of the present invention as mentioned above, the protein of the present invention obtained by immunization of non-human mammal by a part thereof or by cells, etc. which express the protein or monoclonal antibody having a reactivity with a part thereof.

(2) The above-mentioned hybridoma (fused cell) obtained by subjecting the antibody-producing B cell obtained as such to a cell fusion with a myeloma cell derived from mammal.

(3) The monoclonal antibody-producing transformed cell (genetically recombined cell) obtained by transformation of cell except the monoclonal antibody-producing B cell or monoclonal antibody-producing hybridoma with a gene (anyone of gene coding for heavy chain and gene coding for light chain or both of them) coding for the monoclonal antibody isolated from the monoclonal antibody-producing B cell or monoclonal antibody-producing hybridoma.

Here, the monoclonal antibody-producing transformed cell (genetically recombined cell) mentioned in the above (3) means the genetically recombined cell which produces a genetic recombinant of the monoclonal antibody produced by the above B cell (1) or the above hybridoma (2). This recombined monoclonal antibody-producing cell can be manufactured by the same method as used for the manufacture of the above-mentioned chimera monoclonal antibody and human-type antibody.

The "pharmaceutical composition" of the present invention is a pharmaceutical composition consisting of, for example, any of the following (a) to (c) with a pharmaceutically acceptable carrier.

(a) the above-defined antibody (preferably, monoclonal antibody; that is not limited to an antibody derived from nature or a recombined antibody) or a part of the antibody.

(b) DNA fragment useful as an antisense pharmaceutical agent such as the following DNA:

"DNA containing a partial base sequence in the base sequence mentioned in SEQ ID NO:1 or NO:3 or, preferably, the partial base sequence having 14 or more bases or DNA where a part of the DNA is chemically modified; or DNA containing a base sequence complementary to the partial base sequence or DNA where a part of the DNA is chemically modified"

(c) RNA fragment which is useful as an antisense pharmaceutical agent such as the following RNA:

"in an RNA containing a partial base sequence of the base sequence of RNA having a base sequence complementary to the base sequence mentioned in SEQ ID NO:26 or NO:27 or RNA where a part of the RNA is chemically modified, the RNA which is characterized in that the RNA or the chemically modified RNA is hybridized to an RNA coding for the protein having an amino acid sequence mentioned in SEQ ID NO:2".

Here, "pharmaceutically acceptable carrier" is, for example, excipient, diluent, filler, disintegrating agent, stabilizer, preservative, buffer, emulsifier, aromatizer, coloring agent, sweetener, thickener, corrigent, solubilizing aid and other additives. One or more of such carrier(s) is/are used whereby a pharmaceutical composition in a form of tablets, pills, diluted powder, granules, injections, liquids, capsules, troches, elixirs, suspensions, emulsions, syrups, etc. can be prepared.

Such a pharmaceutical composition can be administered either orally or parenterally. Other forms for a parenteral administration include liquid agent for external use, suppositories for enteric administration and pessaries containing one or more active substance(s) and being formulated according to a conventional method.

The dose may vary depending upon age, sex, body weight and symptom of the patient, therapeutic effect, administering method, treating time, type of the active ingredient (the above-mentioned protein or antibody) contained in the pharmaceutical composition, etc. but, usually, it is within a range of from 10 µg to 1,000 mg (or from 10 µg to 500 mg) for one administration to an adult. However, the dose varies according to various conditions and, therefore, less amount than the above may be sometimes sufficient or more than the above range may be sometimes necessary.

Especially in the case of an injection preparation, it is prepared, for example, by dissolving or suspending the ingredient in a non-toxic pharmaceutically acceptable carrier such as a physiological saline or commercially available distilled water for injection so as to make the concentration of from 0.1 µg antibody/ml carrier to 10 mg antibody/ml carrier.

The injection preparation prepared as such may be administered to a human patient to be treated from one to several times a day in a dose of from 1 µg to 100 mg or, preferably, from 50 µg to 50 mg per kg body weight for each administration. Examples of the dosage form are medically appropriate dosage forms such as intravenous injection, subcutaneous injection, intracutaneous injection, intramuscular injection and intraperitoneal injection. Intravenous injection is preferred.

In some cases, an injection preparation may be prepared as a suspension or an emulsion using a non-aqueous diluent (for example, propylene glycol, polyethylene glycol, vegetable oil such as olive oil, alcohol such as ethanol, etc.).

Aseptization of such an injection preparation can be carried out by means of a filtration sterilization passing through a bacteria-retaining filter, compounding of bactericide or irradiation. Injection preparation can be manufactured in a form of to-be-prepared-before-use. Thus, an aseptic solid composition is prepared by means of freeze-drying or the like and may be used by dissolving in aseptic distilled water for injection or other solvent before use.

The pharmaceutical composition of the present invention is able to inhibit the biological activity of the amino acid transporter molecule of the present invention or expression of the molecule and to inhibit the incorporation of the amino acid which is an essential nutrient for the existence or the proliferation of tumor cell into cells and can be used for the therapy of cancer.

The "transgenic mouse" of the present invention is a transgenic mouse where DNA (cDNA or genomic DNA) coding for the protein derived from human being included in the protein of the present invention is integrated onto the intrinsic locus of the mouse and the protein of the present invention is expressed in the body.

To be more specific, it is a transgenic mouse mentioned in the above <52> or <53> and is shown in the following (1) or (2).

(1) in a transgenic mouse having an extrinsic gene, a transgenic mouse which is characterized in that, in the mouse, DNA coding for the protein having an amino acid sequence mentioned in SEQ ID NO:2 is incorporated onto its intrinsic gene whereby cells expressing the protein are present in the body.

(2) the transgenic mouse according to the above (1), wherein the DNA is a DNA containing a base sequence consisting of the base sequence of from 66th to 1586th bases of the base sequence mentioned in SEQ ID NO:1 and any one of the nonsense base sequences represented by TAG, TGA and TAA adjacent to the 1586th base.

The transgenic mouse can be prepared by a usual method which is commonly used in the manufacture of transgenic animals (e.g., refer to *Newest Manual for Animal Cell Tests*, published by LIC, Chapter 7, p. 361-408, 1990).

To be more specific, embryonic stem cell (ES cell) obtained from blastocyst of normal mouse is transformed by an expression vector into which marker gene (such as neomycin resistant gene) and gene coding for the protein having an amino acid sequence mentioned in SEQ ID NO:2 of the present invention are inserted in an expressible manner. The ES cell where the gene coding for the protein is integrated onto the intrinsic gene is selected by a conventional method depending upon the fact whether the marker gene is expressed. Then, the ES cell selected as such is microinjected into a fertilized ovum (blastocyst) obtained from another normal mouse (*Proc. Natl. Acad. Sci.* USA, Vol. 77, No. 12, pp. 7380-7384, 1980; U.S. Pat. No. 4,873, 191). The blastocyst is used as a preliminary parent and is transplanted to uterus of another normal mouse. As such, a founder mouse (child mouse) is born from the preliminary parent mouse. The founder mouse is crossed with a normal mouse to give a heterogeneic transgenic mouse. The heterogeneic transgenic mice are crossed to give a homogeneic transgenic mouse according to Mendel's laws.

It is also possible to prepare the so-called "knockout mouse" based upon a base sequence of DNA (particularly, genomic DNA) coding for protein derived from mouse involved in the present invention, that is, DNA (particularly, genomic DNA) coding for a mouse homologue of human-derived amino acid transporter having an amino acid sequence mentioned in SEQ ID NO:2.

The knockout mouse is a mouse where the intrinsic gene coding for the mouse homologue protein is knocked out (inactivated) and can be prepared, for example, by a positive negative selection method applying a homologous recombination (U.S. Pat. Nos. 5,464,764, 5,487,992 and 5,627, 059; *Proc. Natl. Acad. Sci.* USA, Vol. 86, p. 8932-8935, 1989; *Nature*, Vol. 342, p. 435-438, 1989; etc.). Such a knockout mouse is an embodiment of the present invention as well.

"Labeled DNA" of the present invention is a DNA labeled with enzyme, fluorescent substance, chemiluminescent substance, biotin, avidin or radioisotope (such as $^3$H, $^{14}$C, $^{125}$I, $^{131}$I, etc.) used for the labeling of "labeled monoclonal antibody" which will be mentioned later.

For example, a radiolabeled DNA which is labeled with a radioisotope can be used as a reagent in various test methods, such as southern blotting, for identification of gene coding for the protein of the present invention (*Jikken Igaku*, Supplementary Issue, "Handbook of Genetic Engineering", published by Yodosha, p. 133-140, 1992).

In addition, a labeled DNA which is labeled with a radioactive substance or with a non-radioactive substance such as biotin can be used as a reagent in an in situ hybridization for the analysis of the position of genomic DNA coding for the protein of the present invention on chromosomes (e.g., FISH (fluorescence in situ hybridization), *Jikken Igaku*, Supplementary Issue, "Handbook of Genetic Engineering", published by Yodosha, 1992, p. 271-277).

"Radiolabeled RNA" of the present invention is an RNA where the RNA of the present invention is labeled with a radioisotope such as $^3$H, $^{14}$C, $^{125}$I, $^{131}$I, etc.

The radiolabeled RNA is useful as a reagent for the analysis of expressed state of mRNA coding for the protein of the present invention in cells, tissues or organs such as a northern blotting (*Jikken Igaku*, Supplementary Issue, "Handbook of Genetic Engineering", published by Yodosha, p. 133-140, 1992).

The "labeled substance which can achieve a detectable signal by itself or by the reaction with another substance" for labeling "labeled monoclonal antibody" of the present invention means a substance which is used for a step where it is bonded to the above-defined monoclonal antibody by a physicochemical bond, etc. so that the presence of the monoclonal antibody can be detected.

To be more specific, it is enzyme, fluorescent substance, chemiluminescent substance, biotin, avidin, radioisotope, or the like.

To be still more specific, enzyme such as peroxidase (e.g., horseradish peroxidase), alkaline phosphatase, β-D-galactosidase, glucose oxidase, glucose-6-phosphate dehydrogenase, alcohol dehydrogenase, malic acid dehydrogenase, penicillinase, catalase, apoglucose oxidase, urease, luciferase and acetylcholine esterase; fluorescent substance such as fluorescein isothiocyanate, phycobiliprotein, rare earth metal chelate, dansyl chloride and tetramethyl rhodamine isothiocyanate; radioisotope such as $^3$H, $^{14}$C, $^{123}$I and $^{131}$I; biotin; avidin; and chemiluminescent substance may be exemplified.

Here, each of a radioisotope and a fluorescent substance is solely able to give a detectable signal. On the contrary, each of enzyme, chemiluminescent substance, biotin and avidin is solely unable to give a detectable signal and, therefore, a detectable signal is resulted upon the reaction with one or more other substance(s). For example, in the case of enzyme, at least a substrate is necessary and, depending upon a method for the measurement of the enzymatic activity (e.g., colorimetric method, fluorescent method, bioluminescent method, chemiluminescent method, etc.), various substrates are used. For example, in the case of peroxidase, hydrogen peroxide is used as a substrate. In the case of biotin, it is common to conduct a reaction using at least avidin or an enzyme-modified avidin (such as streptoavidin-β-galactosidase) as a substrate although that is not a limitation. If necessary, various coloring substances depending upon the substrate may be used. For example, when streptoavidin-β-galactosidase is used as a substrate for biotin, it is possible to use 4-methyl-umbelliferyl-β-D-galactosidase as a coloring substance.

The "labeled monoclonal antibody" of the present invention and the above-mentioned "labeled DNA" mean a monoclonal antibody and DNA, respectively, which are labeled with various labeling substances as mentioned above.

The labeled monoclonal antibody can be used for the detection or the quantitative determination of the above-mentioned protein of the present invention. To be more specific, it can be used for the detection of the expression or for the measurement of the expressed amount of the protein of the present invention in various living body samples such as cells (regardless of normal cells, abnormal cells such as tumor cell derived from a living body suffering from disease, natural cells and genetically recombined cells), tissues (regardless of the source whether they are from healthy organism or from organism suffering from disease) or organs (regardless of the source whether they are from healthy organism or from organism suffering from disease). Such a measurement can be carried out according to a conventional method using a commonly used immunohistological technique (*Jikken Igaku*, Supplementary Issue, "Handbook of Cell Engineering", Yodosha, p. 207-213, 1992).

Further, the labeled monoclonal antibody of the present invention can be used not only for the above-mentioned immunohistological test but also for a western blotting method where a soluble membrane protein is prepared from the cell, tissue, organ or a part thereof as a sample to be tested by a conventional method and the soluble membrane protein is made to react with the labeled monoclonal antibody whereby the presence or absence of the protein of the present invention in the soluble membrane protein can be confirmed (*Jikken Igaku*, Supplementary Issue, "Handbook of Cell Engineering", Yodosha, p. 201-206, 1992).

In the immunohistological measurement mentioned as above, any labeled monoclonal antibody which is labeled with any of the above-mentioned labeling substances may be used but, when high detection sensitivity or quantitative sensitivity and convenience in the operation are taken into consideration, it is preferred to use a monoclonal antibody which is labeled with an enzyme such as peroxidase or with biotin.

The present invention also relates to a method for the detection or for the quantitative determination of the protein of the present invention by an immunohistological technique using the above-mentioned labeled monoclonal antibody. To be more specific, it is a method as mentioned above containing, for example, the following steps (1) and (2).

(1) a step where the sample is contacted to the labeled monoclonal antibody of the present invention; and (2) a step where the amount of the labeled monoclonal antibody bonded to the sample is measured by the detection of fluorescence, chemiluminescence or radioactivity depending upon the type of the labeling substance bonded to the labeled monoclonal antibody.

Here, "cell" covers a primary culture cell obtained from human organism, cell line made into subculturable and genetically recombined cell (transformed cell) where a genetic operation is carried out and, preferably, it is a primary culture cell. The cell further covers normal cell and abnormal cell obtained from organism of a patient suffering from disease. Examples of the abnormal cell are various tumor cells. The term "tissue" means any tissue derived from organism of a healthy animal or of a patient suffering from disease and examples of the tissue derived from organism of the patient are tumor tissues. The term "organ or a part thereof" means any organ derived from organism of a healthy animal or of a patient suffering from disease or a part thereof. Examples of the organ derived from the patient are organs having tumor.

To be more specific, the method of the present invention may, for example, include the following steps although this is not a limitation.

(step 1) a step where normal cell, normal tissue or normal organ which is derived, for example, from a healthy person which is excised upon surgical operation and discarded or a part thereof or tumor cell, tumor tissue or tumor-having organ derived from a patient suffering from cancer or a part thereof (the organ or a part thereof may, if necessary, be sliced to give a slice) is fixed with para-formaldehyde or the like to prepare a fixed sample;

(step 2) a step where the labeled monoclonal antibody of the present invention which is labeled with biotin or enzyme such as peroxidase is added to the fixed sample to carry out an antigen-antibody reaction;

(step 3) a step where the fixed sample is washed if necessary and then substrate depending upon the type of the enzyme used or avidin or enzyme-modified avidin such as streptoavidin-β-galactosidase is added whereupon the labeled substance on the labeled antibody is made to react with the substrate, avidin or enzyme-modified avidin (with regard to the substrate, it is possible to add hydrogen peroxide together with diaminobenzidine, 4-chloro-1-naphthol or aminoethylcarbazole in case a labeled antibody which is labeled with enzyme such as peroxidase is used in step 2; avidin or enzyme-modified avidin is used when a labeled antibody which is labeled with biotin is used in step 2);

(step 4) a step where, in case an enzyme-modified avidin is used in step 3, a substrate depending upon the type of the enzyme used for the modification (such as 4-methyl-umbelliferyl-β-D-galactoside) is added whereupon the substrate is made to react with the enzyme bonded to avidin;

(step 5) a step where the fixed sample is washed if necessary so that an enzymatic reaction and a coloring reaction are stopped; and (step 6) a step where the fixed sample is observed under a microscope to measure the color intensity, fluorescence intensity or luminescence intensity.

Since the amino acid transporter protein of the present invention shows a specific expression in a broad range of tumor cells as compared with the expression in normal cells, there is a possibility to judge whether the cell or tissue to be tested is normal or abnormal such as tumor cell when the expression of the protein is detected in various cells or tissues of organism using the above-mentioned immunohistological method.

Another feature of the present invention is to identify a substance which has an ability of inhibiting the biological activity of the protein of the present invention. To be specific, it is a method which was mentioned already for example.

"A method for identifying a substance having an action of suppressing the ability for mediating the incorporation of any one amino acid selected from a group consisting of leucine (Leu), isoleucine (Ile), phenylalanine (Phe), methionine (Met), tyrosine (Tyr), histidine (His), tryptophan (Trp) and valine (Val) into cells where the ability is a biological function of the protein having an amino acid sequence mentioned in SEQ ID NO:2 or NO:4, characterized in that, the method comprises the steps of the following (1) and (2).

(1) a step in which any of the cells mentioned in the following (a) to (d) is incubated in the coexistence of the substance and a radiolabeled amino acid where any one amino acid selected from a group consisting of leucine (Leu), isoleucine (Ile), phenylalanine (Phe), methionine (Met), tyrosine (Tyr), histidine (His), tryptophan (Trp) and valine (Val) is labeled with a radioisotope or in the presence of the radiolabeled amino acid only:

(a) a naturally-occurring cell in which a protein having an amino acid sequence mentioned in SEQ ID NO:2 or NO:4 and a protein having an amino acid sequence mentioned in SEQ ID NO:6 are co-expressed;

(b) a recombinant cell in which a protein having an amino acid sequence mentioned in SEQ ID NO:2 and a protein having an amino acid sequence mentioned in SEQ ID NO:6 or NO:8 are co-expressed by a co-transformation using a DNA containing a base sequence of a translation region in the base sequence mentioned in SEQ ID NO:1 or NO:3;

(c) a non-human-derived recombinant cell in which a protein having an amino acid sequence mentioned in SEQ ID NO:2 and a protein having an amino acid sequence mentioned in SEQ ID NO:6 are co-expressed by a co-introduction of an RNA containing a base sequence of 1st to 1521st bases in the base sequence mentioned in SEQ ID NO:26 and a base sequence comprising any one nonsense base sequence represented by UAG, UGA or UAA adjacent to the 1521st base and an RNA containing a base sequence of 1st to 1587th bases in the base sequence mentioned in SEQ ID NO:27 and a base sequence comprising any one nonsense base sequence represented by UAG, UGA or UAA adjacent to the 1587th base; or (d) a tumor cell derived from human being; and (2) a step in which the radioactivity of the cell incubated in the coexistence of the substance and the radiolabeled amino acid and the radioactivity of the cell incubated in the presence of the radiolabeled amino acid only are measured and the difference between them is compared.

Thus, the method of the present invention is a method which is characterized in that a property of a cell in which the amino acid transporter protein of the present invention (having an amino acid sequence mentioned in SEQ ID NO:2) and the human-derived cell membrane surface molecule 4F2hc (having an amino acid sequence mentioned in SEQ ID NO:6) are co-expressed has an ability of incorporating at least any amino acid from leucine (Leu), isoleucine (Ile), phenylalanine (Phe), methionine (Met), tyrosine (Tyr), histidine (His), tryptophan (Trp) and valine (Val).

Thus, the inhibiting activity of the test substance can be measured by a comparison of the amount of the labeled amino acid incorporated by the cell in an incubation of the cell in the presence of any of the above-mentioned amino acids labeled with a radioisotope ($^{3}$H, $^{14}$C, $^{125}$I or $^{131}$I, etc.) and the test substance with the amount of the labeled amino acid incorporated by the cell in an incubation of the cell in the presence of the labeled amino acid only containing no the test substance.

With regard to the cell, any cell may be utilized so far as it is a cell which co-expresses the two protein molecules. For example, any of the natural cell mentioned in the above (a), the transformed cell (genetically recombined cell) which is transformed by two DNA's coding for each of the both protein molecules as mentioned in (b), the cell into which RNA coding for each of the both protein molecules as mentioned in (c) is introduced and the tumor cell derived from human being as mentioned in (d) may be used.

With regard to the host cell used for the preparation of the transformed cell, various cells which are mentioned in the passage where a method for the expression of the protein of the present invention using the DNA of the present invention is mentioned in detail may be used.

For example, various cells such as natural cell or artificially established recombinant cell which are commonly used in the technical field of the present invention (e.g., bacteria (such as those belonging to genus *Escherichia* and to genus *Bacillus*), yeast (genus *Saccharomyces, Pichia*, etc.), animal cells or insect cells) may be exemplified.

Preferred ones are *Escherichia coli* and animal cells and, to be more specific, *E. coli* (DH5α, TB1, HB101, etc.), cells derived from mouse (COP, L, C127, Sp2/0, NS-1, NIH3T3, etc.), cells derived from rat (PC12, PC12h, etc.), cells derived from hamster (BHK, CHO, etc.), cells derived from monkey (COS1, COS3, COS7, CV1, Velo, etc.) and cells derived from human being (HeLa, cells derived from diploid fibroblast, HEK293 cell, myeloma cell, Namalwa, etc.) may be exemplified.

With regard to the cell into which the RNA is infused, oocytes of *Xenopus laevis* may be exemplified (Special Issue of *Jikken Igaku*, "Experimental Methods for Biosignals", Vol. 11, No. 3, p. 30-38, 1993).

With regard to the tumor cell derived from human being, any tumor cell may be used although it is preferred to use a tumor cell where the protein having an amino acid sequence mentioned in SEQ ID NO:2 and the protein having an amino acid sequence mentioned in SEQ ID NO:6 are confirmed to be co-expressed.

Here, "substance" means a natural substance existing in nature and any substance which is artificially prepared. The substance may be roughly classified into "peptide substance" and "non-peptide substance".

With regard to the "peptide substance", the above fully mentioned antibody of the present invention (preferably monoclonal antibody and, particularly preferably, recombined human-type monoclonal antibody or human monoclonal antibody), oligopeptide and chemically modified substance of any of them. With regard to the oligopeptide, a peptide comprising 5 to 30 amino acids or, preferably, 5 to 20 amino acids may be exemplified. The chemical modification may be designed depending upon various objects such as an increase in half life in blood when administered to organism, an increase in resistance to decomposition or absorption in a digestive organ when administered orally, etc.

With regard to the "non-peptide substance", there may be exemplified "DNA containing a partial base sequence or chemically modified DNA prepared by a chemical modification thereof" useful as an antisense pharmaceutical agent fully mentioned in the definition of the invention in the above-mentioned <4>, "RNA containing a partial base sequence or chemically modified RNA prepared by a chemical modification thereof" useful as an antisense pharmaceutical agent fully mentioned in the definition of the invention in the above-mentioned <6> and chemically synthesized any "compound". Here, with regard to the "compound", there may be exemplified a compound having a molecular weight of about 100 to about 1,000, preferably from about 100 to about 800 or, more preferably, from about 100 to about 600 except DNA, RNA and the above-mentioned peptide substance.

With regard to the substance which can identified by the method for the identification of the present invention, a substance having an ability of inhibiting the proliferation of any tumor cell generated in any tissue of human body is desired. Examples of the tissue are brain, neck, liver, spleen, kidney, large intestine, small intestine, duodenum, prostate gland, lung, stomach, heart, skin, bone marrow, uterus, ovary, testicle, mouth, tongue, bone and chest.

Still another feature of the present invention is a method for the identification of a substance having an ability of inhibiting the transcription of the gene coding for the protein of the present invention to mRNA or the expression of protein of the present invention. To be more specific, it is the following method which was mentioned already.

"a method for the identification of a substance having an ability of inhibiting the transcription of the gene coding for the protein having an amino acid sequence mentioned in SEQ ID NO:2 or NO:4 to mRNA or the expression of the protein having an amino acid sequence mentioned in SEQ ID NO:2 or 4 which is characterized in containing the following steps:

(1) a step where a cell which is a cell co-transformed by the DNA of the following (a), (b) and (c) and the cell is transformed in such a manner that, depending upon the expression of the protein having an amino acid sequence of SEQ ID NO:2 coded by the DNA of the (a), a reporter protein coded by the DNA of the (c) is expressed at the same time is incubated in the presence or absence of the substance:

(a) DNA containing a base sequence of the translation region of the base sequence mentioned in SEQ ID NO:1 or NO:3;

(b) DNA containing a base sequence of the translation region of the base sequence mentioned in SEQ ID NO:5 or NO:7;

(c) DNA coding for a reporter protein; and (2) a step where expressed amounts of the reporter protein in each of the cells incubated in the presence of the substance and those incubated in the absence of the substance are measured and compared".

The method is the so-called "reporter gene assay" and, to be more specific, it is a method where DNA coding for the amino acid transporter molecule of the present invention, DNA coding for the expression adjustment controlling region of the DNA and DNA coding for reporter protein generating fluorescence (luciferase derived from firefly, umishiitake [a kind of marine plants], etc.; GFP (green fluorescence protein) derived from jellyfish; etc,) are inserted in such a manner that the reporter protein molecular can be expressed depending upon the expression of the transporter molecule, cell which is commonly used for the manufacture of genetically recombined protein is transformed by the above-prepared expression vector, the resulting one is contacted to the test compound and the amount of transporter molecule expressed depending upon the action of the compound is indirectly measured by measuring the amount of fluorescence generated by the reporter protein which is expressed together with the expression of the molecule whereupon it is analyzed whether the compound affects the expression of the transporter molecule (U.S. Pat. Nos. 5,436,128 and 5,401,629 may be referred to for example).

Incidentally, although the identification of the compound using the present assay is possible by means of a manual operation, that can be carried out quickly and easily using the so-called high through-put screening where the assay is carried out automatically using a machine (robot) (*Soshiki Baiyo Kogaku*, Vol. 23, No. 13, p. 521-524; U.S. Pat. No. 5,670,113).

The terms "cell" and "substance" used in the above-mentioned method are the same as those defined already.

EXAMPLES

The present invention will now be illustrated in more detail by way of Examples although it goes without saying that the present invention is not limited to the embodiments mentioned in those Examples only.

Incidentally, in the following Examples, each operation was carried out according to the method mentioned in *Molecular Cloning* (by Sambrook, J., Fritsh, E. F. and Maniatis, T.; published by Cold Spring Harbor Press in 1989) unless otherwise mentioned or, when a commercially available reagent or kit was used, it was used according to the directions for use thereof.

Example 1

Isolation of cDNA of Human Cell Membrane Surface Molecule 4F2hc and Preparation of cRNA (1) Preparation of cDNA Fragment Coding for Rat 4F2hc by Means of an RT-PCR.

According to the conventional method, pure poly(A)$^+$ RNA was prepared from liver of rat. 5'-Primer (SEQ ID NO:9) and 3'-primer (SEQ ID NO:10) were also synthesized based upon a cDNA sequence (*Biochem. J.*, Vol. 312, p. 863, 1995) coding for rat 4F2hc.

An RT-PCR (reverse transcription-polymerase chain reaction; *Jikken Igaku*, Supplementary Issue, "PCR and Its Applications", Vol. 8, No. 9, 1990; and "Gene Amplification PCR—Its Basis and New Developments", published by Kyoritsu Shuppan, 1992) was carried out using the two primers and Taq polymerase (manufactured by Takara) where the poly(A)$^+$RNA was used as a template. The reaction was carried out according to the protocol attached the polymerase using a DNA Thermal Cycler (manufactured by Perkin Elmer Cetus).

The amplified cDNA was subjected to an agarose electrophoresis and purified using a DNA extraction kit (manufactured by Qiagen) to prepare a fragment of rat 4F2hc gene (from 34th to 479th bases of the base sequence mentioned in SEQ ID NO:7).

Incidentally, the cDNA sequence coding for the rat 4F2hc and the corresponding amino acid sequence were mentioned in SEQ ID NO:7 and NO:8, respectively.

(2) Manufacture of cDNA Coding for Human 4F2hc and Preparation of cRNA.

A kit for the synthesis of cDNA (trade name: Superscript Choice System; manufacture by Gibco) is used and, according to the experimental operation method attached to the kit, human cDNA was prepared from poly(A)⁻RNA (manufactured by Clontech) derived from human placenta and the cDNA was integrated into a cleaved site of a phage vector λZipLox (manufactured by Gibco) with a restriction enzyme EcoRI using a DNA ligase (manufactured by Gibco) to prepare a human cDNA library.

The gene fragment of rat 4F2hc prepared in the above (1) was labeled with $^{32}$P-dCTP to manufacture a probe and that was used as a probe for a plaque hybridization.

The above-prepared human cDNA library was screened as follows using the probe.

The cDNA library was sown on an agar plate and a replica was prepared using a commercially available filter membrane. A hybridization was carried out at 37° C. for one night in a hybridization solution using the replica and the radioactive probe. With regard to the solution for the hybridization, a buffer of pH 6.5 containing 5×SSC, 3×Denhard's solution, 0.2% of SDS, 10% of dextran sulfate, 50% of formamide, 0.01% of Antifoam B (an antifoaming agent manufactured by Sigma), 0.2 mg/ml of salmon sperm-modified DNA, 2.5 mM of sodium pyrophosphate and 25 mM of MES was used. The filter membrane was washed with 0.1×SSC/0.1% SDS at 37° C.

The positive clone selected by the hybridization was isolated by a single plaque, subjected to an in vivo excision, recombined to a plasmid pZL1 (manufactured by Gibco) and recovered as a plasmid DNA. The plasmid DNA was further subcloned to a pBlueScriptII SK (-) (manufactured by Stratagene).

In order to determine the base sequence of cDNA of human 4F2hc contained in the resulting clone, seven kinds of primers were synthesized (SEQ ID NO:11 to SEQ ID NO:17). The base sequence of cDNA was determined by a dyeterminator cycle sequencing method (by Applied Biosystems) using the seven kinds of synthetic primers and T7 primers and SP6 primers which were the commercially available universal primers (manufactured by Stratagene). As a result, it was confirmed that the cloned cDNA was that of the gene of human 4F2hc.

Incidentally, the cDNA sequence coding for the human 4F2hc and the corresponding amino acid sequence were mentioned in SEQ ID NO:5 and SEQ ID NO:6, respectively.

From the plasmid containing the cDNA of human 4F2hc prepared as above, cRNA (an RNA complementary to cDNA; SEQ ID NO:27) was prepared according to a conventional method using a T7 RNA polymerase (manufactured by Stratagene) (Special Issue of *Jikken Igaku*, "Method of Experiments of Biosignals", Vol. 11, No. 3, p. 33-34, 1993).

Example 2

Isolation of cDNA of Human Amino Acid Transporter LAT1 and Preparation of cRNA

Human cDNA was prepared from poly(A)⁺RNA (purchased from Clontech) derived from human teratocarcinoma cell line PA-1 using a kit for the synthesis of cDNA (trade name: Superscript Choice System; manufactured by Gibco) according to an experimental operation method attached to the kit and then the cDNA was integrated into a site of a phage vector λZipLox (manufactured by Gibco) cleaved by a restriction enzyme EcoRI using a DNA ligase (manufactured by Gibco) to prepare a human cDNA library.

cDNA (DDBJ/EMBL/Gen Bank registration No: AB015432; a segment corresponding to 1135th to 1529th bases of SEQ ID NO:3) coding for a rat amino acid transporter LAT1 was excised by a restriction enzyme BamHI. Incidentally, an amino acid sequence of the rat amino acid transporter LAT1 was mentioned in SEQ ID NO:4.

This DNA segment was labeled with $^{32}$P-dCTP to prepare a probe and it was used as a probe for a plaque hybridization.

The above-prepared human cDNA library was screened as follows using the probe.

The cDNA library was sown on an agar plate and a replica was prepared using a commercially available filter membrane. A hybridization was carried out for one night at 37° C. in a hybridization solution using the replica and the radioactive probe. With regard to the solution for the hybridization, a buffer of pH 6.5 containing 5×SSC, 3×Denhard's solution, 0.2% of SDS, 10% of dextran sulfate, 50% of formamide, 0.01% of Antifoam B (an antifoaming agent manufactured by Sigma), 0.2 mg/ml of salmon sperm-modified DNA, 2.5 mM of sodium pyrophosphate and 25 mM of MES was used. The filter membrane was washed with 0.1×SSC/0.1% SDS at 37° C.

The positive clone selected by the hybridization was isolated by a single plaque, subjected to an in vivo excision, recombined to a plasmid pZL1 (manufactured by Stratagene) and recovered as a plasmid DNA. The plasmid DNA was excised by a restriction enzyme PstI to give three cDNA fragments having the sizes of 1.8 kb, 2.5 kb and 4.3 kb. Each of the fragments of 1.8 kb and 2.5 kb was subcloned to a pBlueScriptII SK (-) (manufactured by Stratagene). The cDNA fragment of 4.3 kb was subjected to a self-ligation.

In order to determine the base sequence of cDNA of human amino acid transporter LAT1 contained in each of the plasmids having the three cDNA fragments, eight kinds of primers were synthesized (SEQ ID NO:18 to SEQ ID NO:25). The base sequence of cDNA was determined by a diterminator cycle sequencing method (by Applied Biosystems) using the eight kinds of synthetic primers and M13 forward primer and M13R reverse primer which were the commercially available universal primers (manufactured by Stratagene).

The resulting sequence of full-length cDNA coding for the human amino acid transporter LAT1 and the corresponding amino acid sequence were mentioned in SEQ ID NO:1 and SEQ ID NO:2, respectively.

Further, from the resulting plasmid containing the cDNA of human 4F2hc coding for the human amino acid transporter LAT1, cRNA (SEQ ID NO:26; an RNA complementary to cDNA) was prepared using a T3 RNA polymerase (manufactured by Stratagene).

When a homology in the amino acid sequences for a rat amino acid transporter LAT1 and for a human amino acid transporter LAT1 was analyzed, the human LAT1 had an amino acid homology of about 91% to the rat LAT1. The result is shown in FIG. 1.

When an amino acid sequence of the human amino acid transporter LAT1 was analyzed by a hydrophobic plot analysis (Kyte-Doolittle hydropathy analysis), it was estimated that the human LAT1 was a cell membrane surface molecule having 12 transmembrane domains (membrane-spanning domains). The result is shown in FIG. 2.

Example 3

Analysis of Expression of mRNA of Human Amino Acid Transporter LAT1 in Various Tissues of Human Being The cDNA coding for the human amino acid transporter LAT1 (cDNA fragment corresponding to 649th to 1128th bases of SEQ ID NO:1) was excised by a restriction enzyme SmaI and labeled with $^{32}$P-dCTP to prepare a hybridization probe. A northern blotting to various tissues of human being was carried out using the probe as follows.

Figure 3:
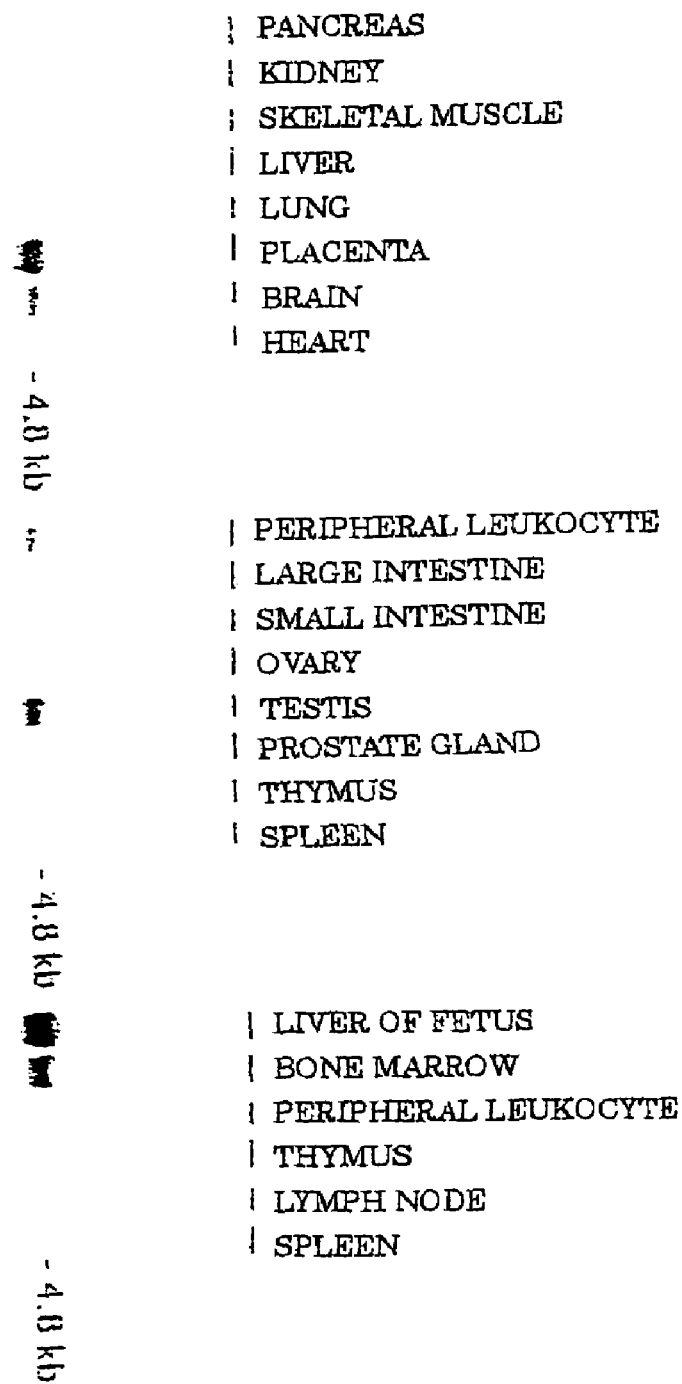
FIG. 3 shows an expressed state of mRNA of a human amino acid transporter LAT1 in various human tissues by a northern blotting.

A Nylon membrane where human poly(A)+RNA was blotted (trade name: MTN Blot; manufactured by Clontech) was subjected to hybridization and washing using the $^{32}$P-dCTP-labeled human LAT1 probe according to the protocol attached to the kit. The result is shown in FIG. 3.

As a result, expression of mRNA of human LAT1 having a size of about 4.8 kb was noted in placenta, brain, testis, bone marrow and fetal liver. A weak expression of mRNA was noted in peripheral leukocytes as well.

Example 4

Analysis of Biological Activity of Human Amino Acid Transporter LAT1

(1) Analysis of Ability of Mediating the Transport of Amino Acid into the Cell.

From the studies up to now concerning the proliferation of tumor cells, it has been predicted that the known heavy chain (4F2hc) of a cell membrane surface antigen which is a heterodimer of heavy chain classified under a glycoprotein of type II and light chain and named 4F2 (CD98) may play an important role in activation of an amino acid transporter which has not been identified yet (*J. Immunol.*, Vol. 126, p. 1409-1414, 1981; *J. Immunol.*, Vol. 129, p. 623-628, 1982; *Proc. Natl. Acad. Sci.* USA, Vol. 84, p. 6526-6530, 1987; *Cancer Res.*, Vol. 46, p. 1478-1484, 1986; *J. Biol. Chem.*, Vol. 267, p. 15285-18288, 1992; *Proc. Natl. Acad. Sci.* USA, Vol. 89, p. 5606-5610, 1992; *Biochem. J.*, Vol. 324, p. 535-541, 1997; and *J. Expt. Biol.*, Vol. 196, p. 123-137, 1994).

In view of the above, the fact whether the amino acid transporter LAT1 of the present invention carries the transport of the amino acid into the cells was analyzed by such a method that the cells in which only human LAT1 was expressed and other cells in which both human LAT1 and human 4F2hc were expressed together were used and the incorporated amounts of leucine (neutral amino acid) into each cells were measured.

Incidentally, such a test method is based upon a method where oocytes of *Xenopus laevis* which are commonly used in the incorporation test of various substances into cells are used (Special Issue of *Jikken Igaku*, "Method of Experiments of Biosignals", Vol. 11, No. 3, p. 30-38, 1993).

A sole cRNA (25 ng) coding for the human LAT1 prepared in the above Example, a sole cRNA (25 ng) coding for the human 4F2hc prepared in the above Example, or the cRNA (17.5 ng) coding for the human LAT1 together with the cRNA (7.5 ng) coding for the human 4F2hc was injected into oocytes of *Xenopus laevis* and incubated for 2 or 5 days whereupon oocytes expressing the human LAT1 only, oocytes expressing the human 4F2hc only and oocytes co-expressing the human LAT1 and the human 4F2hc were prepared, respectively.

A radiolabeled leucine which was radiolabeled with $^{14}$C was used as a substrate and incorporation of the labeled leucine for each oocytes was carried out as follows according to a method by Kanai, et al. (Kanai and Hediger, *Nature*, Vol. 360, p. 467-471, 1992).

Figure 4:
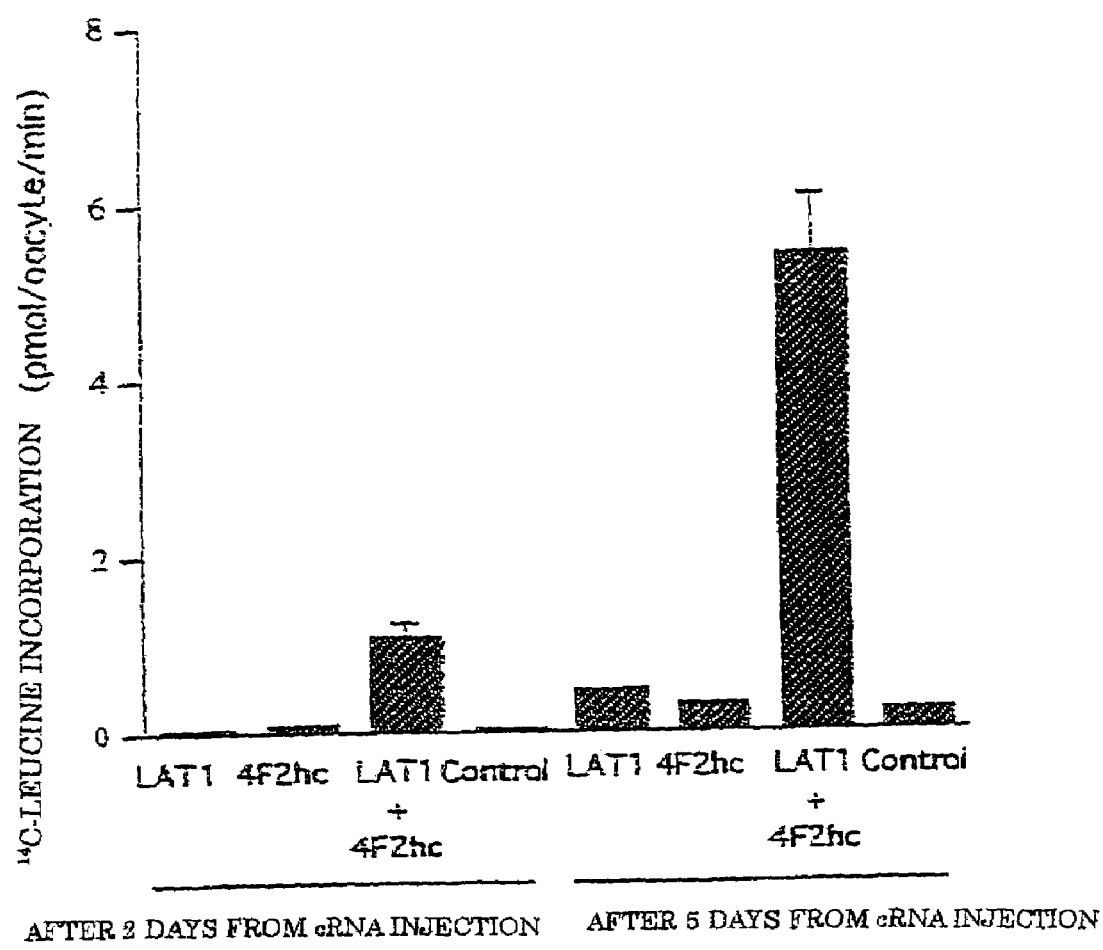
FIG. 4 shows an incorporation activity of leucine into the cells of *Xenopus laevis* oocytes wherein a human amino acid transporter LAT1 and a human cell membrane surface molecule 4F2hc are co-expressed.

Thus, to be specific, each oocytes were incubated for 30 minutes in a choline chloride uptake solution (consisting of 100 mM of choline chloride, 2 mM of potassium chloride, 1.8 mM of calcium chloride, 1 mM of magnesium chloride and 5 mM of HEPES; pH 7.4) containing $^{14}$C-labeled leucine (50 µM) whereby the amount of the $^{14}$C-labeled leucine incorporated into the oocytes was determined by measuring the radioactivity of the oocytes by means of a scintillation counter. Incidentally, as a control, the same experiment was carried out using the oocytes where any of the above RNA was not injected but only water was infused. The result is shown in FIG. 4.

The result was that, in the oocytes where only human LAT1 was expressed, incorporation of leucine was rarely noted like in the case of oocytes into which only water was injected as a control while, in the case of oocytes where both human LAT1 and human 4F2hc were expressed, a large incorporation of leucine was confirmed. The result was believed to be due to the fact that human 4F2hc is necessary in order that the human amino acid transporter LAT1 achieves the function of mediating the incorporation of amino acid.

(2) Analysis of Salt-Dependency of the Transport of Amino Acid into the Cells.

The fact whether there is a salt-dependency of the human amino acid transporter LAT1 in the ability of mediating the transport of amino acid into the cells was analyzed as follows. To be specific, the analysis was carried out by observing the changes in the incorporated amount of leucine into the cells by changing the type of the uptake solution which incubated the oocytes in the above-mentioned Example 4(1).

The oocytes of *Xenopus laevis* co-expressing the human LAT1 and the human 4F2hc prepared in Example 4(1) were incubated for 30 minutes in the above-mentioned choline chloride uptake solution containing $^{14}$C-labeled leucine (50 µM, a sodium uptake solution containing $^{14}$C-labeled leucine (50 µM) (100 mM of choline chloride in the above choline uptake solution were changed to 100 mM of sodium chloride) or a gluconic acid uptake solution containing $^{14}$C-labeled leucine (50 µM) (100 mM of sodium chloride in the above sodium uptake solution were changed to 100 mM of sodium gluconate).

Figure 5:
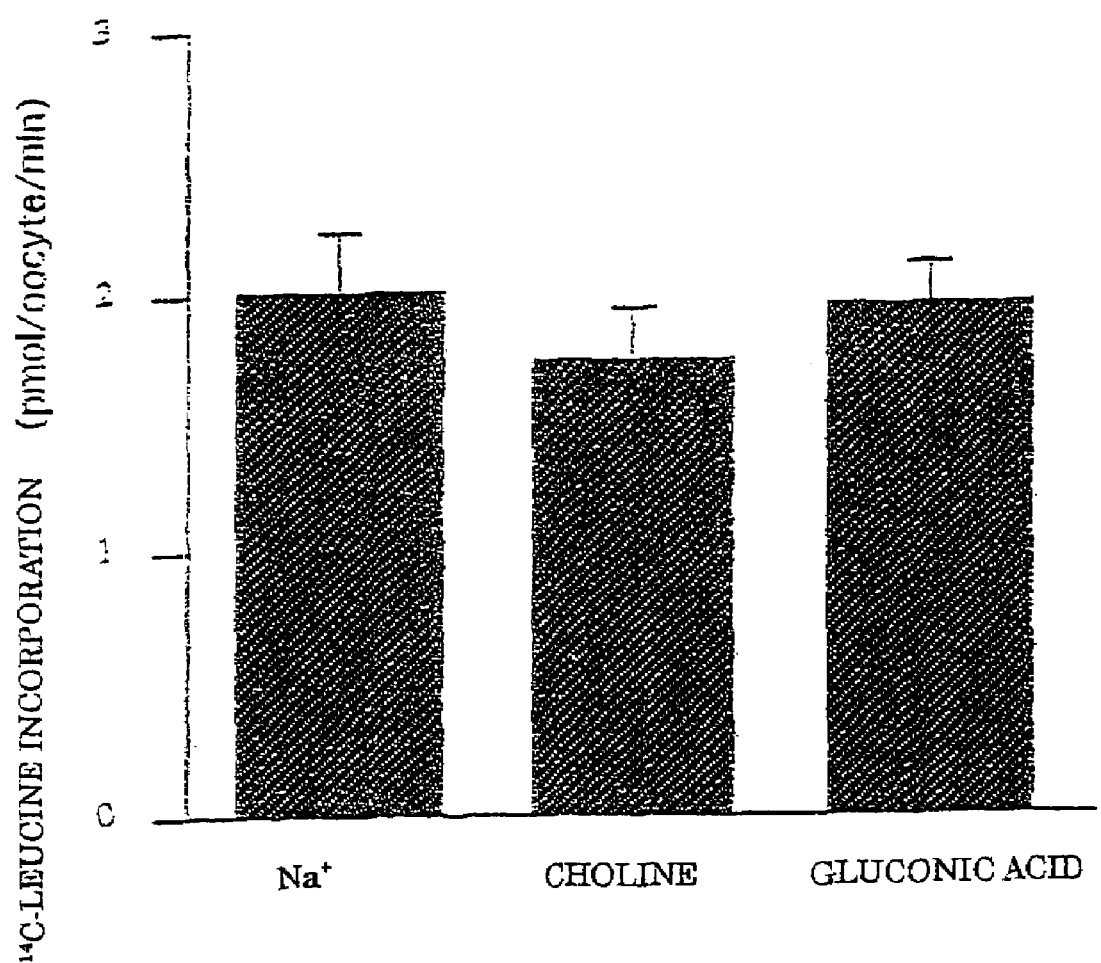
FIG. 5 shows the amount of leucine incorporated into the cells when *Xenopus laevis* oocytes wherein a human amino acid transporter LAT1 and a human cell membrane surface molecule 4F2hc are co-expressed are incubated in the presence of various salts.

Amount of the $^{14}$C-labeled leucine incorporated into the oocytes was determined by measuring the radioactivity of the oocytes by means of a scintillation counter. The result is shown in FIG. 5.

The result shows that, even when choline outside the oocytes was changed to sodium or even when chlorine ion outside the oocytes was changed to gluconic acid ion, that did not affect the incorporation of leucine into the oocytes at all. Therefore, if was noted that the human amino acid transporter LAT1 was a transporter molecule which acted independently upon sodium ion and chlorine ion.

(3) Affinity of the Human Amino Acid Transporter LAT1 to the Substrate.

In order to analyze the affinity of the human amino acid transporter LAT1 to the substrate, a Michaelis-Menten kinetic test (*Dictionary of Biochemistry*, second edition, p. 1307-1308, 4th printing, 1992) was carried out.

This kinetic test was carried out by checking the changes in the incorporated rate of leucine depending upon the difference in the concentration of leucine as a substrate.

Figure 6:
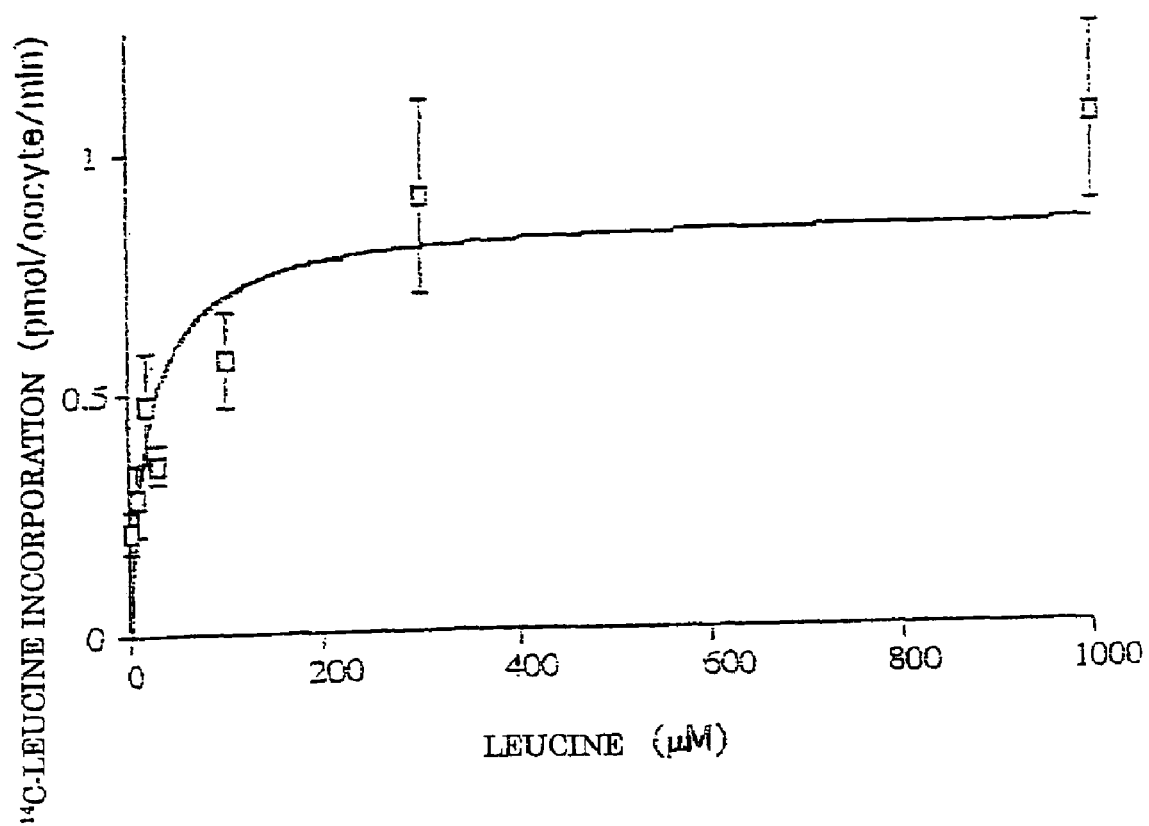
FIG. 6 shows an affinity of a human amino acid transporter LAT1 to the substrate in a Michaelis-Menten kinetic test.

The incorporation experiment of leucine was carried out according to the method mentioned in the above Example 4(1) using oocytes of *Xenopus laevis* where the human LAT1 and the human 4F2hc were co-expressed. The result is shown in FIG. 6.

As a result, the Michaelis constant (Km) was about 21 µM.

(4) Analysis of Substrate Specificity of the Human Amino Acid Transporter LAT1 (No.1)

The substrate specificity of the human amino acid transporter LAT1 (type of the substrate incorporated into the cells mediated by LAT1) was analyzed by a competitive antagonism test.

To be specific, oocytes of *Xenopus laevis* which co-expressed the human LAT1 and the human 4F2hc were analyzed by measuring the changes in the incorporated amount of $^{14}$C-labeled leucine as a substrate into the oocytes when incubated in the presence of a test substance (various amino acid, pharmaceuticals, physiologically active substances or other low-molecular synthetic compounds). When the incorporated amount of the $^{14}$C-labeled leucine decreased as compared with the control where no test substance was added, it was noted that the test substance was incorporated into the oocytes mediated by the human amino acid transporter LAT1.

Oocytes of *Xenopus laevis* co-expressing the human LAT1 and the human 4F2hc prepared in Example 4(1) were incubated for 30 minutes in a choline chloride uptake solution containing $^{14}$C-labeled leucine (20 μM) and any of the following test substances (2 mM).

Incidentally, as a control, incubation was similarly carried out in a choline uptake solution containing $^{14}$C-labeled leucine but containing none of the test substance.

[Test Substances]

Glycine, alanine, serine, threonine, cysteine, leucine, isoleucine, phenylalanine, methionine, tyrosine, histidine, tryptophan, valine, asparagine, glutamine, aspartic acid, glutamic acid, lysine, arginine, proline and BCH (2-amino-2-norbornane-carboxylic acid).

Figure 7:
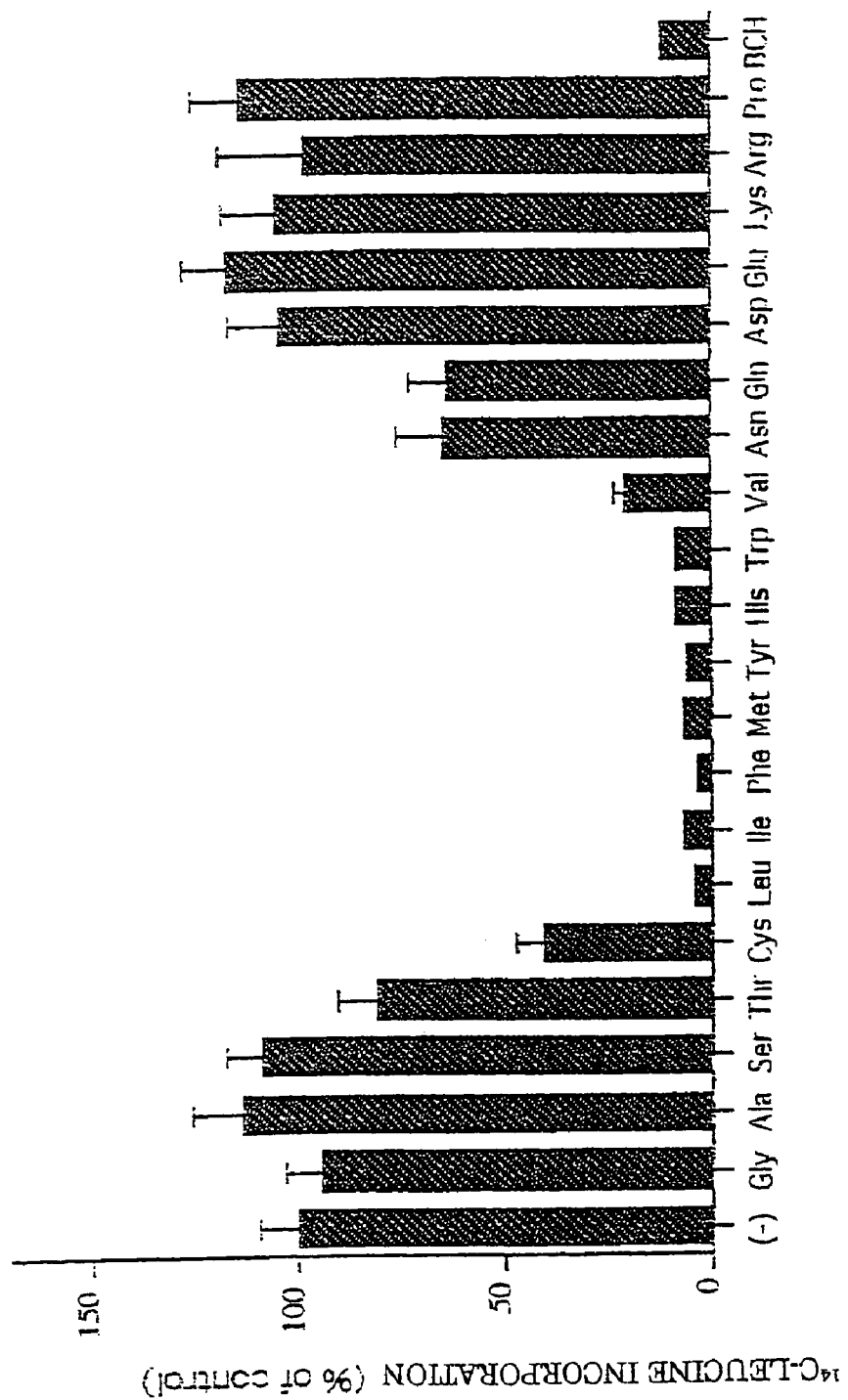
FIG. 7 shows the amount of radiolabeled leucine as a substrate incorporated into the cells when *Xenopus laevis* oocytes wherein a human amino acid transporter LAT1 and a human cell membrane surface molecule 4F2hc are co-expressed are incubated in the presence of various amino acids.

Amount of the $^{14}$C-labeled leucine incorporated into the oocytes was determined by measuring the radioactivity of the oocytes by means of a scintillation counter. The result is shown in FIG. 7.

Further, incorporation of the following test substances into oocytes was also tested according to the above-mentioned method using $^{14}$C-labeled phenylalanine instead of $^{14}$C-labeled leucine. As a control, incubation in a choline uptake solution containing $^{14}$C-labeled phenylalanine but containing none of the test substance was carried out similarly.

[Test Substances]

L-DOPA (a therapeutic agent for Parkinson's disease) and triiodothyronine (a thyroid hormone).

Figure 8:
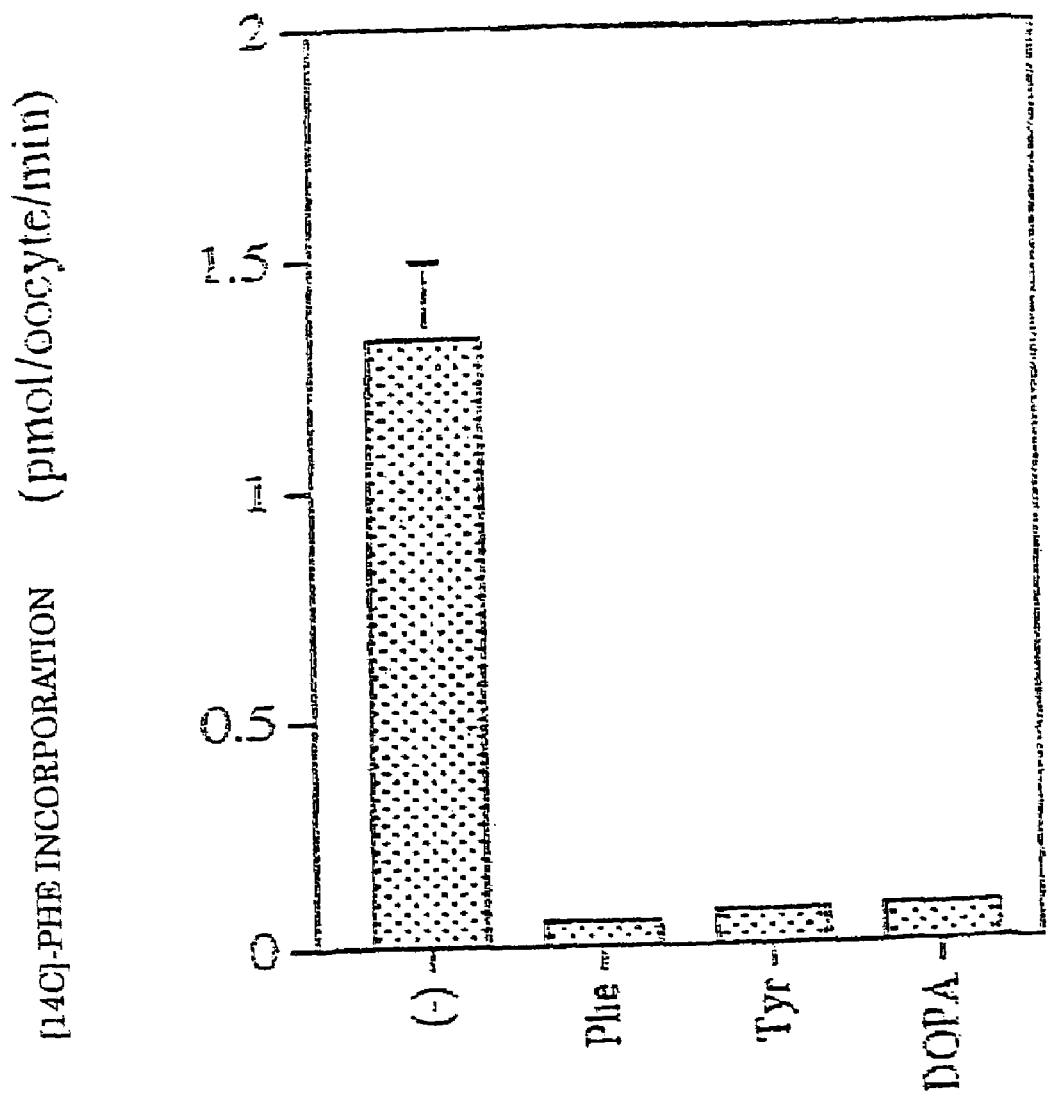
FIG. 8 shows the amount of radiolabeled phenylalanine as a substrate incorporated into the cells when *Xenopus laevis* oocytes wherein a human amino acid transporter LAT1 and a human cell membrane surface molecule 4F2hc are co-expressed are incubated in the presence of amino acid or a pharmaceutical agent.
Figure 9:
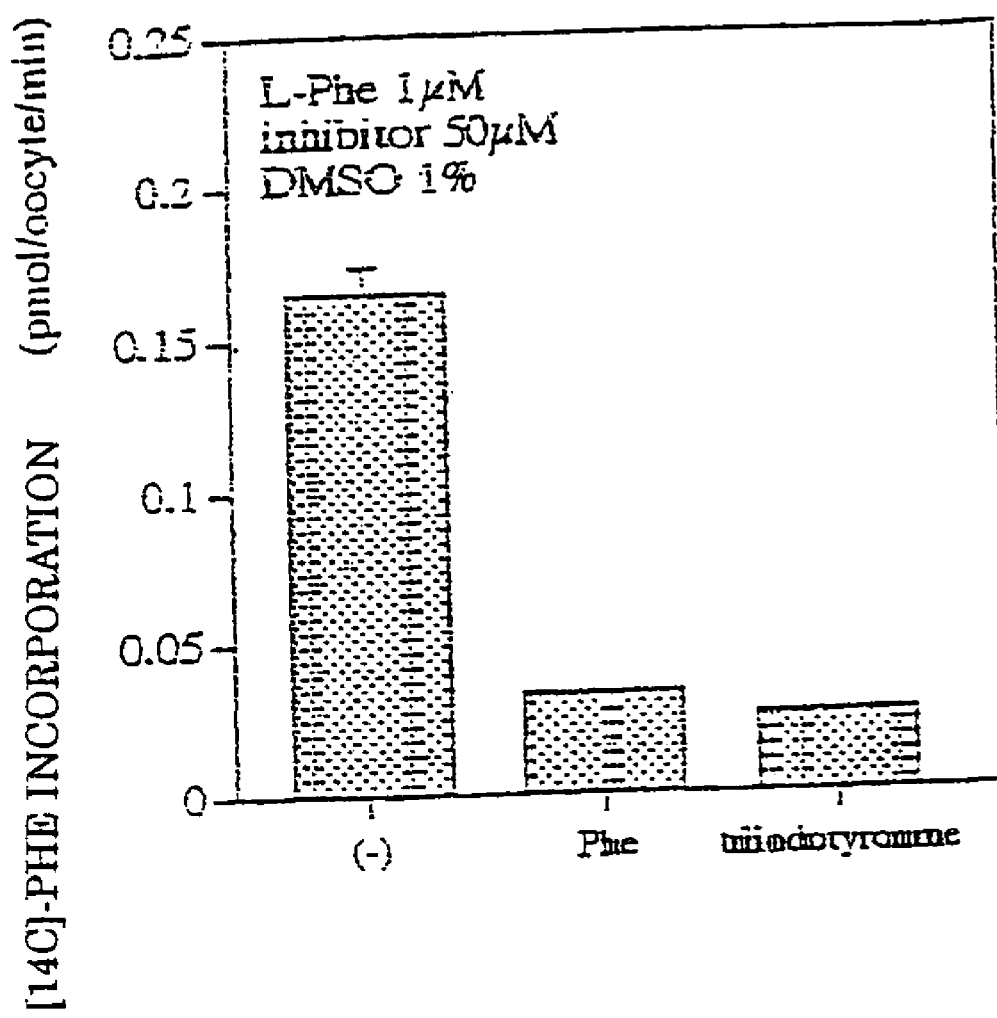
FIG. 9 shows the amount of radiolabeled leucine as a substrate incorporated into the cells when *Xenopus laevis* oocytes wherein a human amino acid transporter LAT1 and a human cell membrane surface molecule 4F2hc are co-expressed are incubated in the presence of amino acid or physiologically active substance.

The result is shown in FIG. 8 and FIG. 9.

As a result, in various amino acids, pharmaceuticals and physiologically active substances, a cis-inhibiting action for incorporation of $^{14}$C-labeled leucine or $^{14}$C-labeled phenylalanine into the cells (oocytes) was observed. Particularly, leucine, isoleucine, phenylalanine, methionine, tyrosine, histidine, tryptophan and valine strongly inhibited the incorporation of $^{14}$C-labeled leucine mediated by the human LAT1 and, therefore, it was strongly suggested that any of the amino acids was transported into the oocytes mediated by the human LAT1. 2-Amino-2-norbornane-carboxylic acid (BCH) which was known as an inhibitor for incorporation of neutral amino acids also inhibited the incorporation of $^{14}$C-labeled leucine. Further, incorporation of $^{14}$C-labeled phenylalanine into oocytes was strongly inhibited by the pharmaceutical agents such as L-DOPA (a therapeutic agent for Parkinson's disease) and the physiologically active substances such as triiodothyronine (thyroid hormone). On the contrary, when acidic amino acids (such as glutamic acid and aspartic acid) or basic amino acids (such as lysine and arginine) were used as the test substances, incorporation of $^{14}$C-labeled leucine mediated by the human LAT1 was not affected at all.

The result strongly suggests that the human amino acid transporter LAT1 mediates the transport of various amino acids (particularly neutral or nearly neutral amino acids), various pharmaceuticals, various physiologically active substances and other low-molecular synthetic compounds into cells.

(5) Analysis of the Substrate Specificity of the Human Amino Acid Transporter LAT1 (No. 2).

Based upon the result of Example 4(4), an analysis was carried out whether leucine, isoleucine, phenylalanine, methionine, tyrosine, histidine, tryptophan and valine were incorporated into oocytes mediated by the human LAT1.

The test was carried out in the same manner as in Example 2(1) using each of the following $^{14}$C-labeled amino acids prepared by labeling each of the above-mentioned amino acids with $^{14}$C instead of $^{14}$C-labeled leucine as a substrate.

[$^{14}$C-Labeled Amino Acids]

$^{14}$C-Labeled leucine, $^{14}$C-labeled isoleucine, $^{14}$C-labeled phenylalanine, $^{14}$C-labeled methionine, $^{14}$C-labeled tyrosine, $^{14}$C-labeled histidine, $^{14}$C-labeled tryptophan and $^{14}$C-labeled valine.

Figure 10:
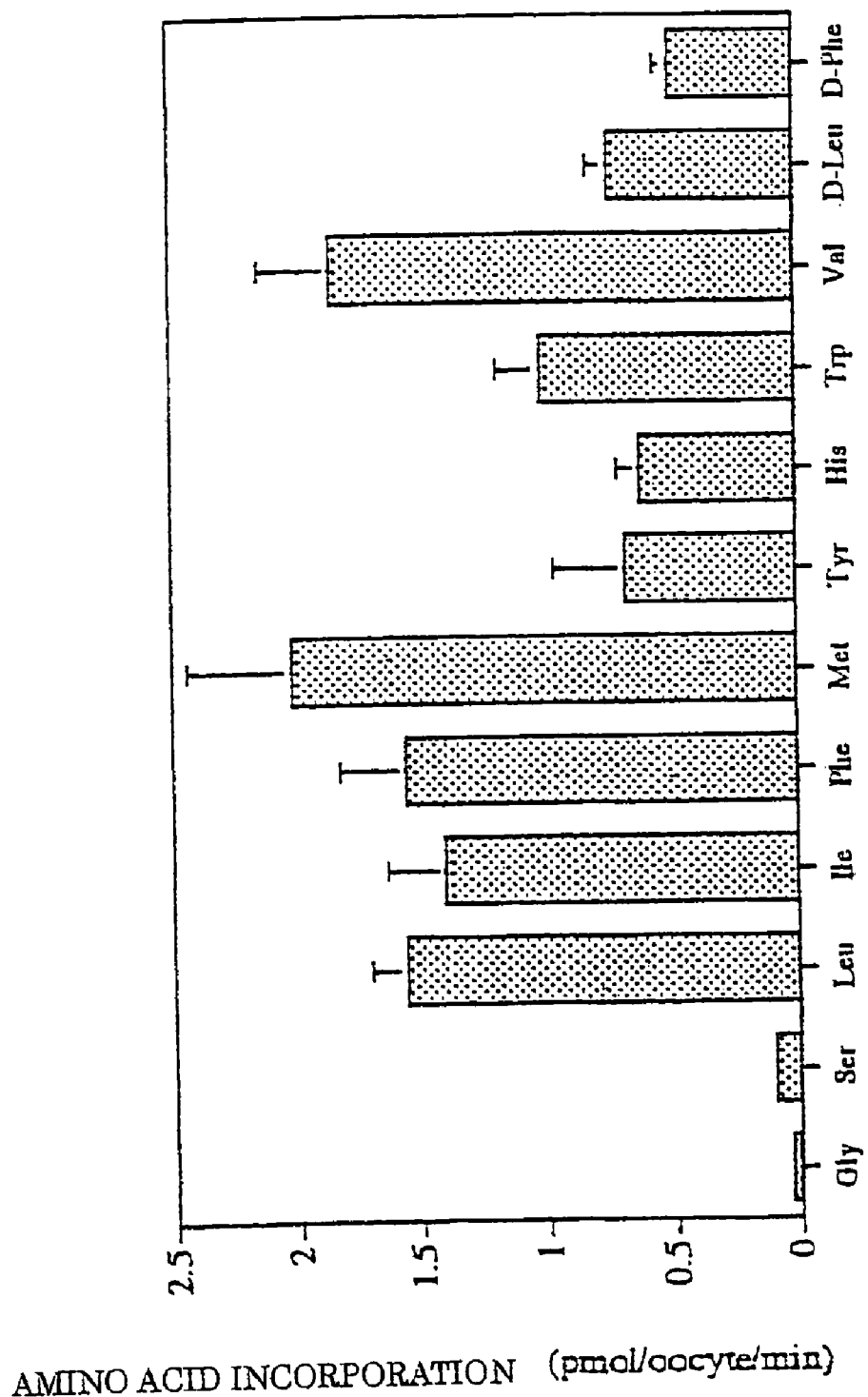
FIG. 10 shows the amount of various radiolabeled amino acids as substrates incorporated into the cells of *Xenopus laevis* oocytes wherein a human amino acid transporter LAT1 and a human cell membrane surface molecule 4F2hc are co-expressed.

For the sake of comparison, the same test was carried out using $^{14}$C-labeled glycine, $^{14}$C-labeled serine, $^{14}$C-labeled D-leucine and $^{14}$C-labeled D-phenylalanine. The result is shown in FIG. 10.

As a result, it was confirmed that leucine, isoleucine, phenylalanine, methionine, tyrosine, histidine, tryptophan and valine were significantly incorporated into oocytes. In addition, D-leucine and D-phenylalanine were also shown to be incorporated into the oocytes.

Example 5

Analysis of Expression of mRNA of the Human Amino Acid Transporter LAT1 in Various Tumor Cells Derived from Human Being Total RNA was collected from various tumor cells derived from human being by a conventional method using Isogen (trade name; manufactured by Nippon Gene) and the RNA was subjected to an agarose electrophoresis by a conventional method and blotted to a nitrocellulose membrane.

The cDNA fragment coding for the human amino acid transporter LAT1 prepared in Example 3 was subjected to a northern blotting using a hybridization probe prepared by labeling with $^{32}$P-dCTP. The northern blotting was carried out according to a protocol attached to a commercially available Nylon membrane for northern blotting (such as MTN Blot [trade name] manufactured by Clontech) where various poly(A)$^+$RNA was blotted.

As a result of the northern blotting, expression of mRNA coding for the human LAT1 in various tumor cells derived from human being was able to be confirmed.

Example 6

Cloning of a Rat Neutral Amino Acid Transporter (1) Isolation of cDNA of Rat 4F2hc and Preparation of cRNA.

A cDNA library was prepared from poly(A)$^+$RNA purified from rat liver using a kit for the synthesis of cDNA (trade name: Superscript Choice System; manufactured by Gibco) and integrated into the excised site of the restriction enzyme EcoRI of a phage vector λZipLox (manufactured by Gibco). A segment corresponding to from 135th to 580th bases of a rat 4F2hc gene (Broer, et al., *Biochem. J.*, Vol. 312, p. 863, 1995) was amplified by a PCR and labeled with $^{32}$P-dCTP and the resulting probe was used for the screening of a rat liver cDNA library. Hybridization was carried out for one night in a solution for hybridization of 37° C. and the filter membrane was washed with 0.1×SSC/0.1% SDS at 37° C. With regard to the solution for the hybridization, a buffer of pH 6.5 containing 5×SSC, 3×Denhard's solution, 0.2% of SDS, 10% of dextran sulfate, 50% of formamide, 0.01% of Antifoam B (an antifoaming agent manufactured by Sigma), 0.2 mg/ml of salmon sperm-modified DNA, 2.5 mM of sodium pyrophosphate and 25 mM of MES was used. The cDNA moiety of the λZipLox phage into which cDNA was incorporated was incorporated into a plasmid pZL1 and then further subcloned to a plasmid pBluescript II SK− (manufactured by Stratagene).

With regard to the resulting clone, i.e. a clone containing cDNA of rat 4F2hc, a base sequence of cDNA was determined by a dideoxy method using a synthetic primer for the determination of base sequence and a kit for the determination of base sequence (trade name: Sequenase ver. 2.0; manufactured by Amersham). As such, it was confirmed that the cloned cDNA was that of a rat 4F2hc gene. The base sequence of the resulting 4F2hc was shown in SEQ ID NO:2 in the Sequence Listing which will be given later.

From the above-prepared plasmid containing the cDNA of the rat 4F2hc, cRNA (an RNA complementary to cDNA) was prepared using a T7 RNA polymerase.

(2) Cloning of a Rat Neutral Amino Acid Transporter LAT1.

This was carried out as follows by means of an expression cloning method according to a method by Kanai, et al. (Kanai and Hediger, *Nature*, Vol. 360, p. 467-471, 1992).

A rat C6 glioma cell poly(A)+RNA (400 μg) was fractionated by a gel electrophoresis.

Each of the fractions obtained by the fractionation was injected into oocytes together with the cRNA of rat 4F2hc obtained in the above (1) followed by incubating for two days.

Figure 11:
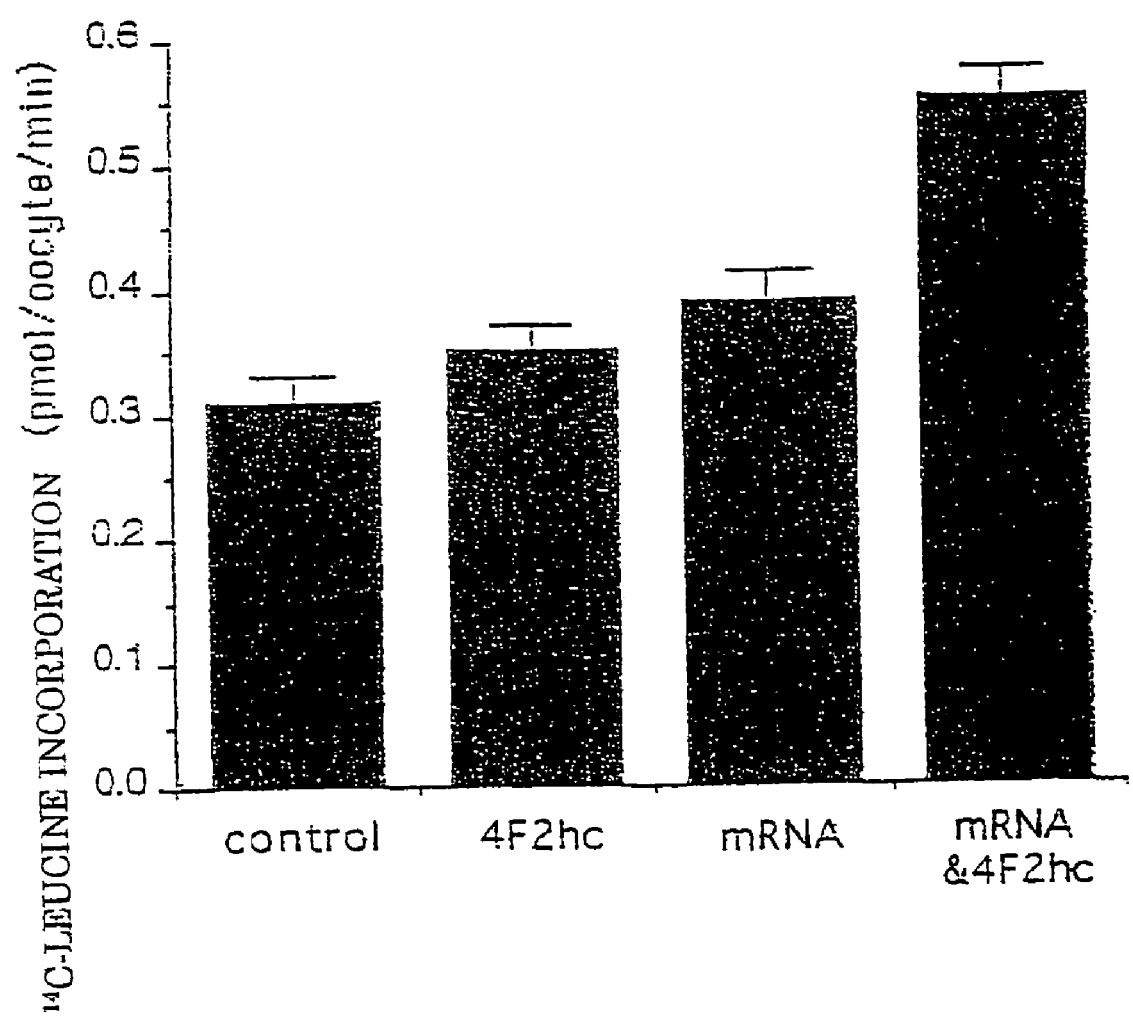
FIG. 11 shows the result of the experiment of leucine incorporation by oocytes into which mRNA derived from rat C6 glioma and/or cRNA of rat 4F2hc gene are/is injected.

For the oocytes into which RNA was injected, an experiment of incorporation of a substrate was carried out using leucine as a substrate as follows according to a method by Kanai, et al. (Kanai and Hediger, *Nature*, Vol. 360, p. 467-471, 1992). Thus, the oocytes were incubated for 30 minutes in a choline chloride uptake solution containing 50 μM of $^{14}$C-leucine as a substrate (100 mM of choline chloride, 2 mM of potassium chloride, 1.8 mM of calcium chloride, 1 mM of magnesium chloride and 5 mM of HEPES; pH 7.4) and the incorporated rate of the substrate was measured by counting the radioactivity which was incorporated into the oocytes. Incidentally, in this system, it was confirmed that a synergistic enhancement in the incorporation was noted in the oocytes into which both rat C6 glioma cell poly(A)+RNA (mRNA) and cRNA of rat 4F2hc were injected as compared with the oocytes into which each of them was solely infused (FIG. 11).

Among the RNA fractions prepared by the fractionation, the oocytes into which RNA was infused selected a fraction showing the highest incorporation rate of leucine. A cDNA library was prepared for the poly(A)+RNA (2.8-4.0 kb) of this fraction using a kit for the synthesis of cDNA and a plasmid cloning (trade name: Superscript Plasmid System; manufactured by Gibco). Those DNA's were integrated into the sites recognizing the restriction enzymes Sal1 and Not1 of the plasmid pSPORT1 (manufactured by Gibco) and the resulting recombined plasmid DNA was introduced into a competent cell of *Escherichia coli* DH10B strain (trade name: Electro Max DH10B Competent Cell; manufactured by Gibco). The resulting transformant was incubated on a nitrocellulose membrane to give about 500 colonies per plate. A plasmid DNA was prepared from those colonies followed by excising with a restriction enzyme NotI. The resulting DNA was subjected to an in vitro transcription to synthesize a capped cRNA.

The resulting cRNA (about 45 ng) was infused into oocytes together with the rat 4F2hc cRNA (5 ng) obtained hereinabove (1). With regard to those oocytes, a screening for positive clone was carried out by conducting a leucine incorporation experiment according to the same way as mentioned above. In conducting the screening, the group where DNA extracted from plural clones was pooled was checked and, when incorporation of leucine was confirmed in some groups, they were further subdivided into plural groups and a screening was further carried out.

With regard to the resulting clone, i.e. the clone containing cDNA of the rat neutral amino acid transporter LAT1, the base sequence thereof was determined by a dideoxy method using a synthetic primer for the determination of group sequence and a kit for the determination of base sequence, (trade name: Sequenase ver. 2.0; manufactured by Amersham).

As a result, a base sequence of the rat neutral amino acid transporter LAT1 gene was obtained. In addition, the base sequence of cDNA was analyzed by a conventional method and the translation region of cDNA and the amino acid sequence of LAT1 encoded there were determined. The translation region was 64th to 1599th bases.

Those sequences were shown in SEQ ID NO:4 (amino acid sequence) and NO:3 (base sequence) in the Sequence Listing which will be given later.

Figure 12:
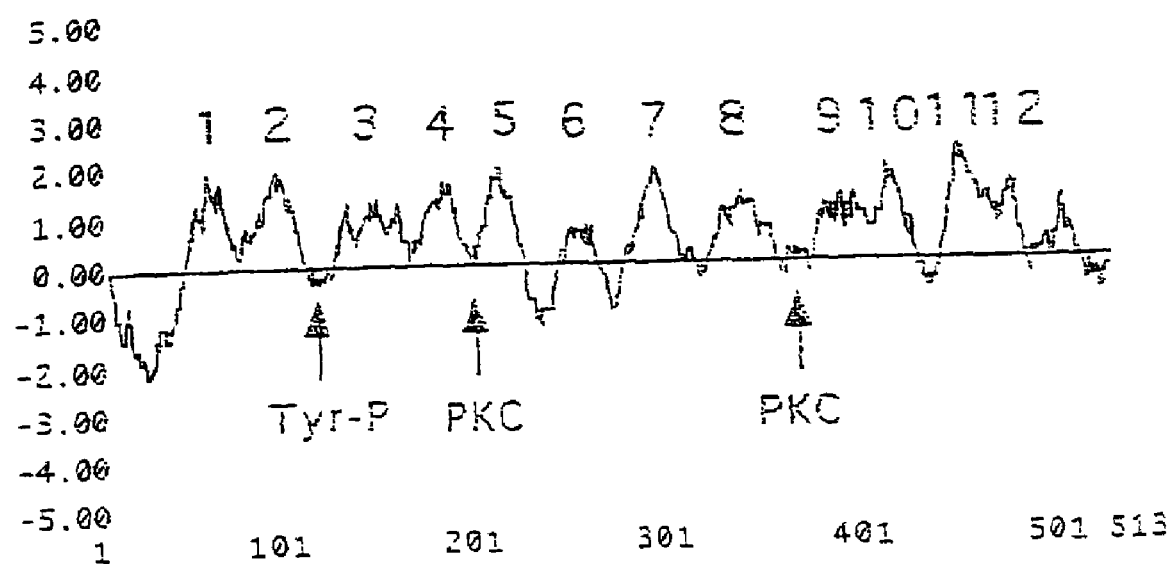
FIG. 12 shows hydrophobic plots of a rat neutral amino acid transporter LAT1.

As a result of analysis of the amino acid sequence of LAT1 by means of a Kyte-Doolittle hydropathy analysis (hydrophobic plot), 12 transmembrane regions (membrane-spanning domains) were predicted as shown in FIG. 12. Further, in the second hydrophilic loop, there was a tyrosine phosphorylated site and, in the fourth and eighth hydrophilic loops, there were two sites supposed to be proteinkinase-C-dependent phosphorylated sites.

(3) Expression of LAT1 Gene in Various Tissues of Rat and in an Cultured Rat Cell Line (Analysis by Northern Blotting).

A cDNA fragment corresponding to 202nd to 1534th bases of the rat LAT1 gene was labeled with $^{32}$P-dCTP and, using it as a probe, a northern blotting was carried out as follows for the RNA extracted from various tissues of rat and from cultured tumor cell line derived from rat. Thus, 3 μg of poly(A)+RNA were subjected to an electrophoresis using 1% agarose/formaldehyde gell and transferred to a nitrocellulose filter. The filter was subjected to a hybridization for one night in a hybridization solution containing the LAT1 cDNA fragment labeled with $^{32}$P-dCTP at 42° C. The filter was washed with 0.1×SSC containing 0.1% of SDS at 65° C.

Figure 13:
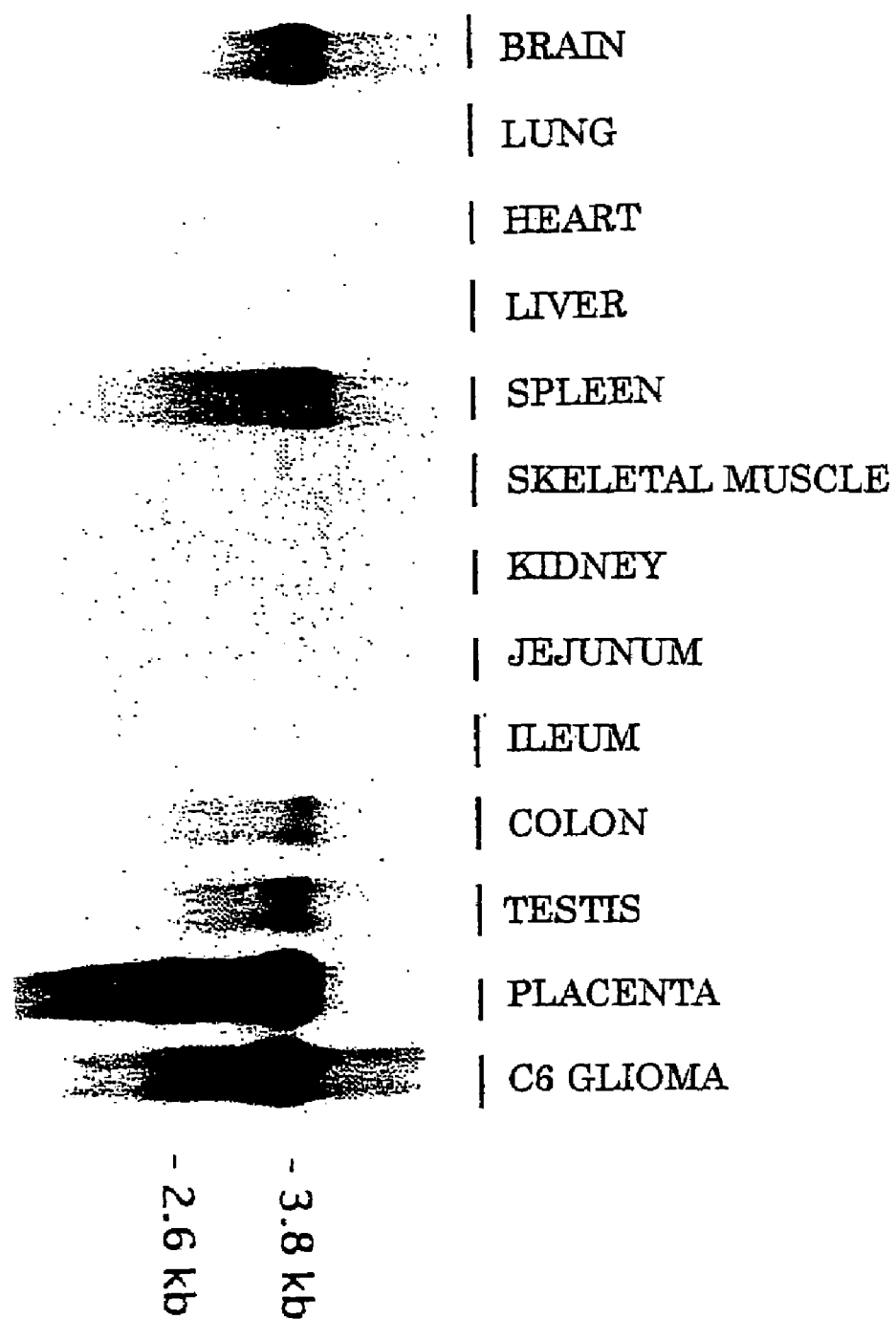
FIG. 13 is a photograph as a substitute for a drawing which shows the result of analysis of expression of LAT1 gene mRNA in various organ tissues of rat by a northern blotting.
Figure 14:
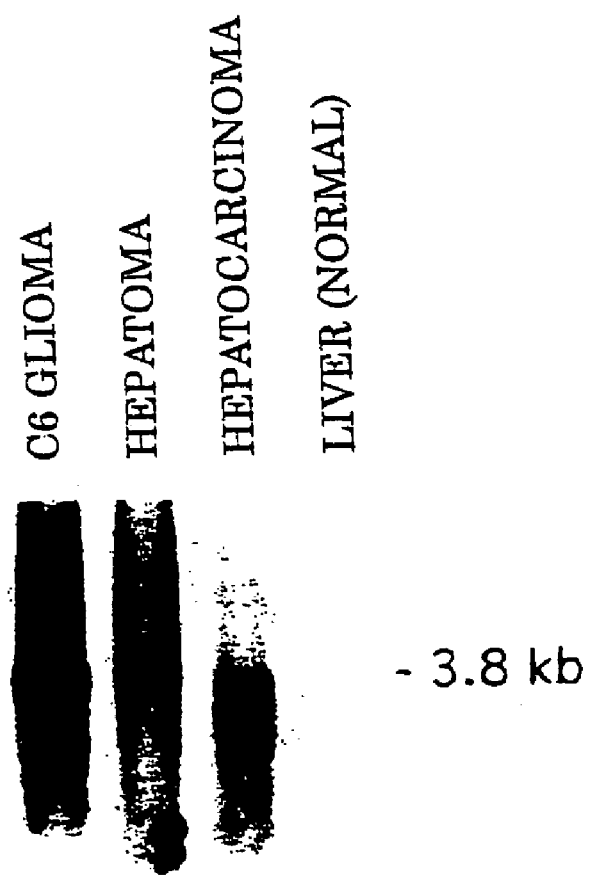
FIG. 14 is a photograph as a substitute for a drawing which shows the result of comparison of expression of LAT1 gene mRNA in each culture cell line of rat with expression of LAT1 gene mRNA in the liver of rat by a northern blotting.

As a result of the northern blotting (FIG. 13), bands were detected at about 3.8 kb in C6 glioma cell, placenta, brain, spleen, large intestine and testis and, in placenta, another band was detected at about 2.6 kb in addition to the above whereupon expression was noted. Although the expression was very weak in normal liver, a strong band was detected at about 3.8 kb in rat hepatoma cell line and rat hepatocarcinoma cell line whereupon an expression was noted (FIG. 14).

Further, upon long exposure, a faint band was noted at about 3.8 kb even in other tissues.

(4) Expression of LAT1 Gene in a Human Tumor Cell Line (Analysis by a Northern Blotting).

A cDNA fragment corresponding to 202nd to 1534th bases of the rat LAT1 gene was labeled with $^{32}$P-dCTP and, using this as a probe, RNA extracted from an cultured tumor cell line derived from human being was subjected to a northern blotting as follows. Poly(A)+RNA (3 μg) was subjected to an electrophoresis by 1% agarose/formaldehyde gel and transferred to a nitrocellulose filter. The filter was subjected to a hybridization for one night in a hybridization solution containing the rat LAT1 cDNA fragment labeled with $^{32}$P-dCTP at 37° C. The filter was washed with 0.1× SSC containing 0.1% of SDS at 37° C.

Figure 15:
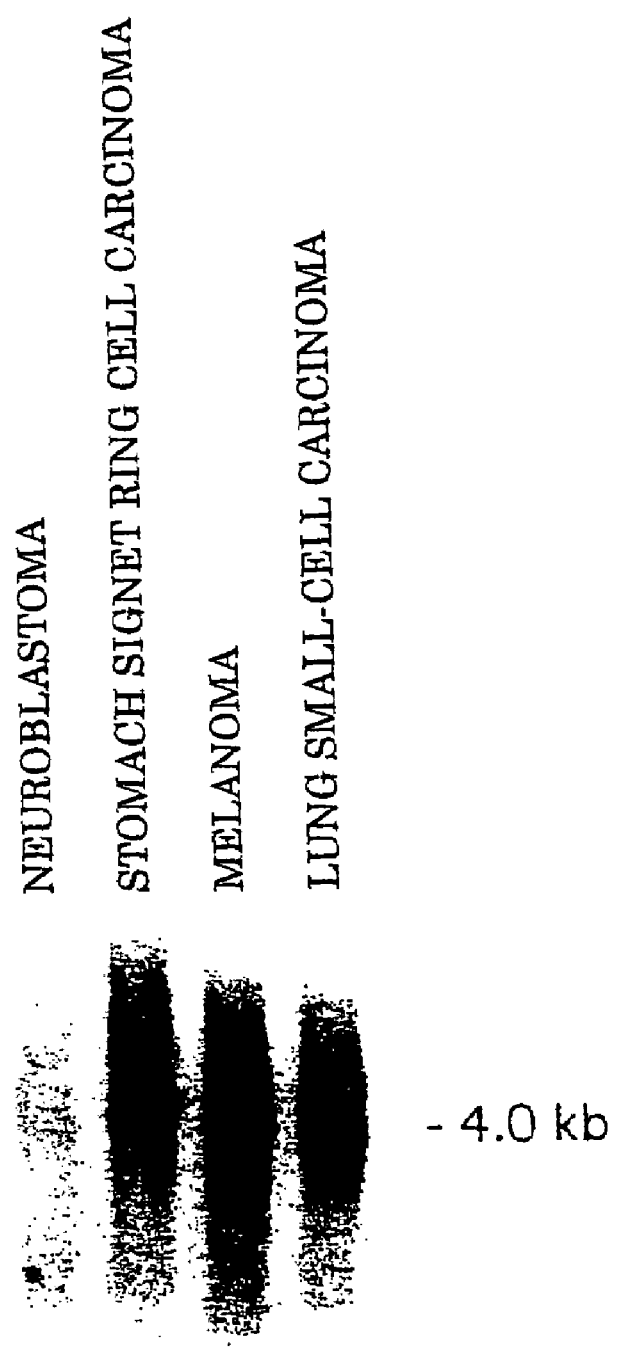
FIG. 15 is a photograph as a substitute for a drawing which shows the result of analysis of expression of LAT1 gene mRNA in each culture cell line of human being by northern blotting.

As a result of the northern blotting (FIG. 15), strong bands were detected at about 4.0 kb in stomach signet ring cell carcinoma cell line, lung small-cell carcinoma cell line and melanoma cell line while a weak band was detected at 4.0 kb in neuroblastoma cell line whereupon an expression was noted.

Example 7

Characterization of the Neutral Amino Acid Transporter LAT1

(1) Role of 4F2hc in the Transporting Activity of LAT1.

Activities in the incorporation of leucine in case the rat LAT1 gene cRNA was solely expressed in oocytes and in case the rat LAT1 gene cRNA and the 4F2hc gene cRNA were simultaneously expressed in oocytes were compared.

Rat LAT1 gene cRNA (25 ng), rat 4F2hc gene cRNA (25 ng) or rat LAT1 gene cRNA (12.5 g)/rat 4F2hc gene cRNA (12.5 ng) was expressed by injecting into the oocytes and incubated for 2 days or 5 days.

An experiment of the incorporation of leucine was carried out as follows in accordance with a method mentioned in the above Example 6(2). Thus, the oocytes into which rat LAT1 gene cRNA, rat 4F2hc gene cRNA or rat LAT1 gene cRNA/rat 4F2hc gene cRNA was injected were incubated for 30 minutes in an uptake solution containing $^{14}$C-leucine (50 μM) and incorporation of radioactivity into the oocytes was measured.

Figure 16:
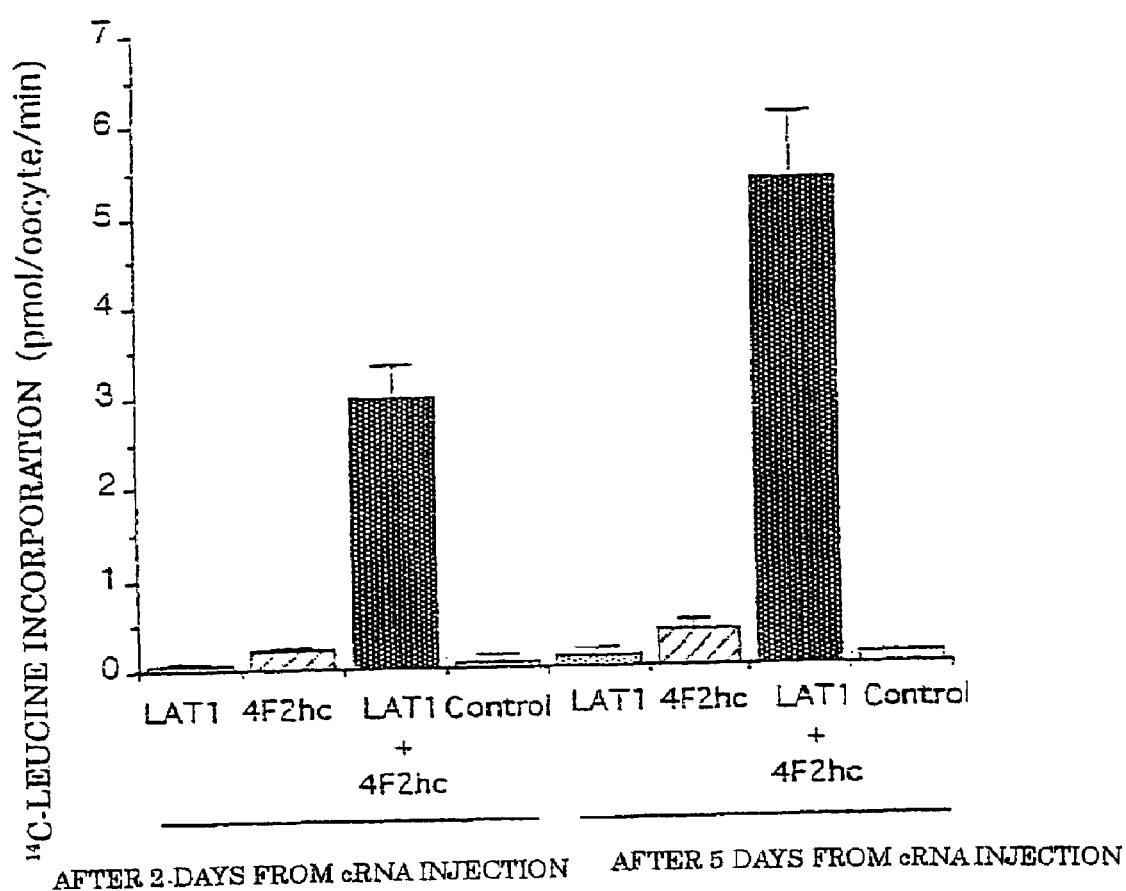
FIG. 16 shows the result where an experiment of incorporation of leucine using oocytes into which rat LAT1 gene cRNA and/or rat 4F2hc gene cRNA are/is injected is carried out after 2 or 5 days after injection of cRNA.

The result (FIG. 16) was that, in the oocytes into which only LAT1 was expressed, incorporation of leucine was in the same level as in the oocytes into which water was injected as a control but, in the oocytes into which both LAT1 and 4F2hc were expressed, a big incorporation of leucine was noted whereupon 4F2hc was believed to be necessary for LAT1 for achieving its function.

(2) Salt-Dependency of the Transport Activity of LAT1.

Influence of a salt added to the medium was tested in a test of incorporation of leucine into the oocytes when both rat LAT1 gene cRNA and 4F2hc gene cRNA were used.

An experiment of the incorporation of leucine was carried out according to a method mentioned in the above Example 6(2) using the oocytes into which both rat LAT1 gene cRNA and rat 4F2hc gene cRNA were injected. With regard to an uptake solution however, a sodium uptake solution (100 mM choline chloride was changed to 100 mM sodium chloride) was used instead of a choline chloride uptake solution when an influence of sodium ion was checked. When an influence of chlorine ion was checked, a gluconic acid uptake solution (100 mM sodium chloride was changed to 100 mM sodium gluconate) was used instead of a sodium uptake solution.

Figure 17:
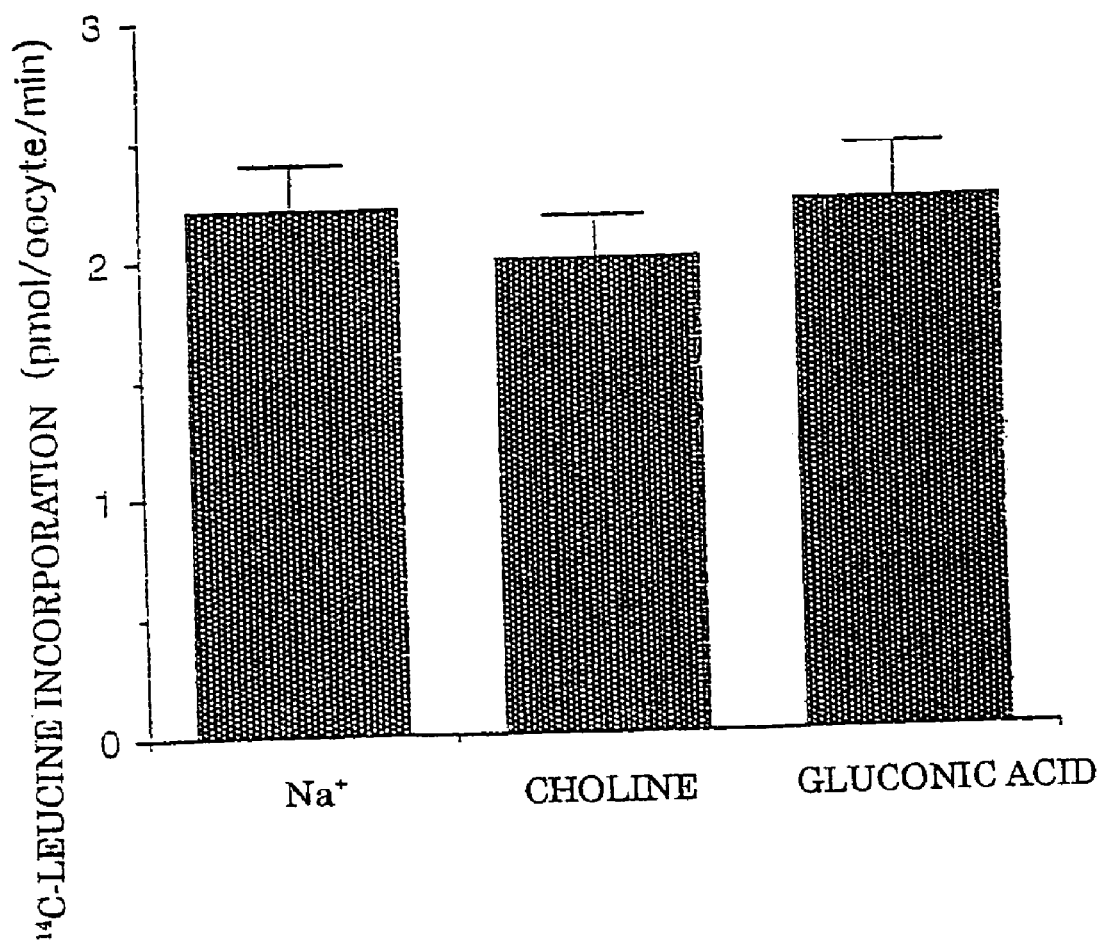
FIG. 17 shows the result of testing the influence of added salt in an experiment of incorporation of leucine using oocytes into which rat LAT1 gene cRNA and rat 4F2hc gene cRNA are injected.

The result (FIG. 17) was that, even when choline outside the oocytes was changed to sodium and even when chlorine ion outside the oocytes was changed to gluconic acid ion, there was no affection in the incorporation of leucine at all. From the result, it was shown that LAT1 was a transporter which acted independently of sodium ion and chlorine ion.

(3) Michaelis-Menten Kinetic Test of LAT1.

A Michaelis-Menten kinetic test was carried out for a neutral amino acid transporter. By checking the changes in the incorporating rate of leucine with the difference in the concentrations of the substrate leucine, a Michaelis-Menten kinetic test of the neutral amino acid transporter was carried out.

Figure 18:
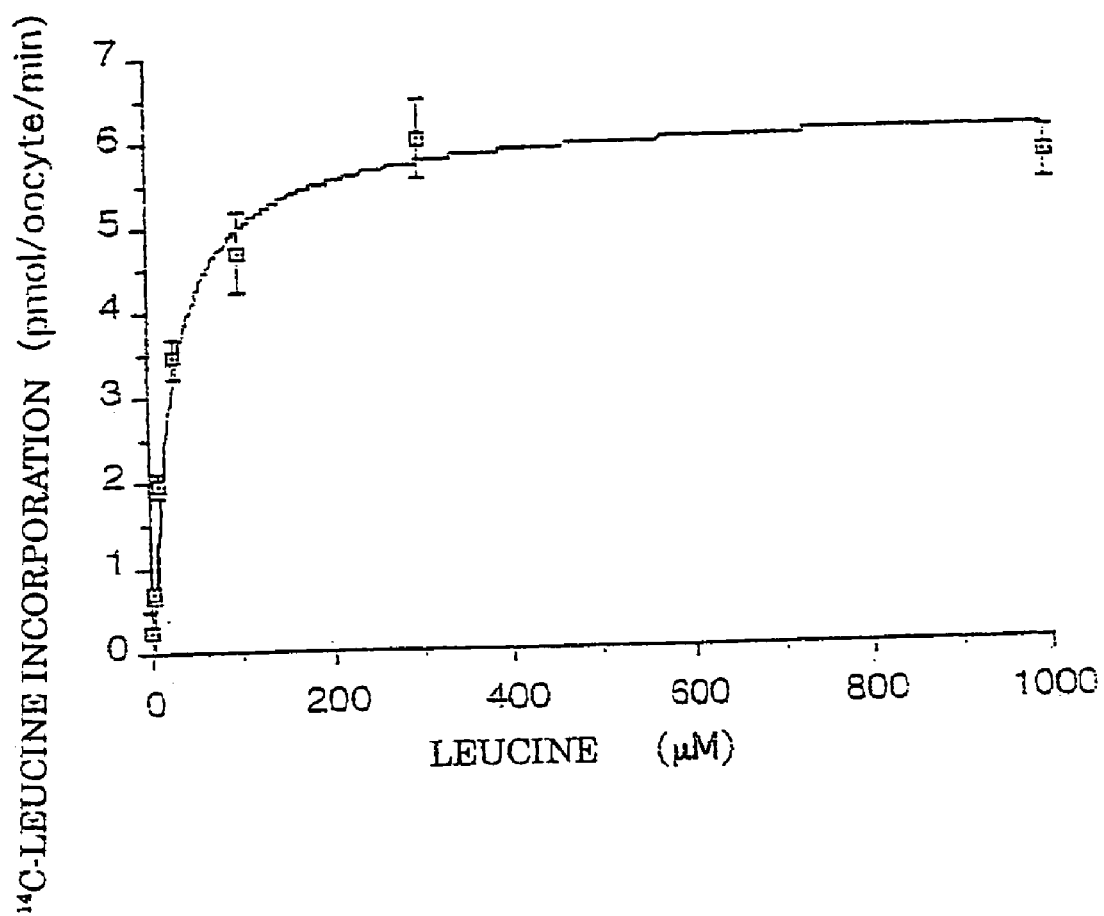
FIG. 18 shows the result of testing the influence of concentration of the substrate leucine in an experiment of incorporation of leucine using oocytes into which rat LAT1 gene cRNA and rat 4F2hc gene cRNA are injected.

An experiment of the incorporation of leucine was carried out according to a method mentioned in the above Example 6(2) using the oocytes into which both rat LAT1 gene cRNA and rat 4F2hc gene cRNA were injected. As a result (FIG. 18), the Km value was about 24 μM.

(4) Substrate-Specificity of LAT1 (an Inhibiting Experiment by Addition of Amino Acid and a Similar Substance thereto).

In an experiment of the incorporation of leucine by the oocytes into which both rat LAT1 gene cRNA and rat 4F2hc gene cRNA were injected, an influence of addition of various amino acids and similar substances thereto to the system was tested.

An experiment of the incorporation of leucine was carried out according to a method mentioned in the above Example 6(2) using the oocytes into which both rat LAT1 gene cRNA and rat 4F2hc gene cRNA were injected. In this case however, a choline uptake solution was used and the incorporation of $^{14}$C-leucine (20 μM) was measured in the presence or absence of 2 mM of various compound (unlabeled).

Figure 19:
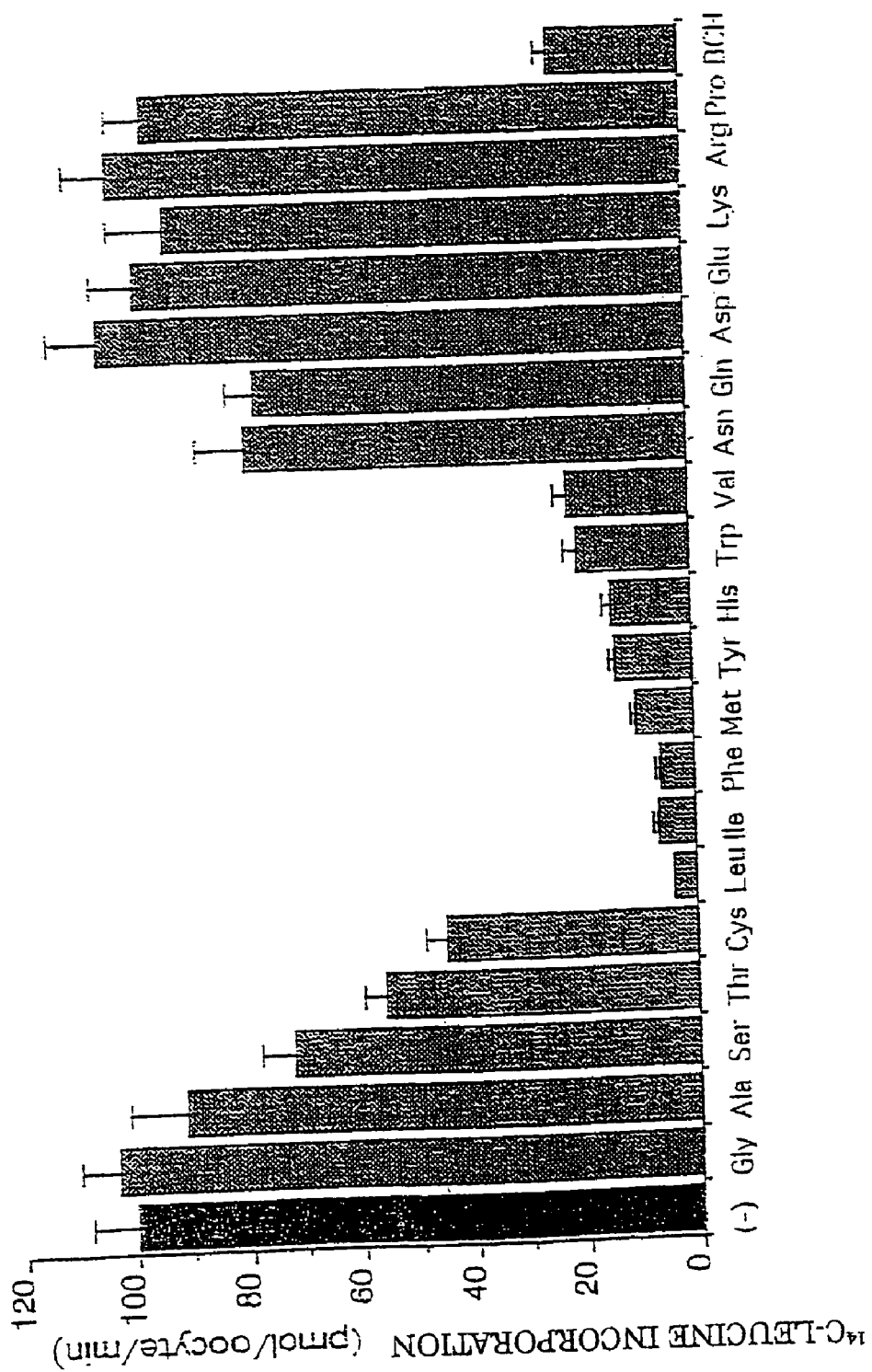
FIG. 19 shows the result of testing the influence of addition of various amino acids or similar compounds thereto on the system in an experiment of incorporation of leucine using oocytes into which rat LAT1 gene cRNA and rat 4F2hc gene cRNA are injected.

The result (FIG. 19) was that a cis-inhibiting effect was observed in various kinds of neutral amino acids. Especially, leucine, isoleucine, phenylalanine, methionine, tyrosine, histidine, tryptophan and valine strongly inhibited the incorporation of $^{14}$C-leucine mediated by LAT1. In addition, in the substances other than the standard amino acids, the incorporation of $^{14}$C-leucine mediated by LAT1 was also inhibited by pharmaceutical agents and physiologically active substances such as L-DOPA (a therapeutic agent for Parkinson's disease), melphalan (antitumor agent), triiodothyronine (thyroid hormone), thyroxin (thyroid hormone). Further, 2-amino-2-norbornane-carboxylic acid which was known as an inhibitor for the incorporation of neutral amino acids inhibited the incorporation of $^{14}$C-leucine as well. Acidic amino acids and basic amino acids did not affect the incorporation of $^{14}$C-leucine mediated by LAT1.

(5) Substrate-Selectivity of LAT1 (a Test on the Incorporation Using Various Kinds of Amino Acids and Similar Substances thereto as Substrates).

Incorporation by LAT1 was tested using various kinds of amino acids and similar substances thereto as substrate.

A test on the incorporation using various kinds of amino acids and similar substances thereto was carried out according to the method mentioned in the above Example 6(2) using the oocytes into which both rat LAT1 gene cRNA and rat 5F2hc gene cRNA were injected. As a substrate however, various radiolabeled compounds were used in place of $^{14}$C-leucine.

The result was that incorporation into the oocytes was noted when leucine (a $^{14}$C compound), isoleucine (a $^{14}$C compound), phenylalanine (a $^{14}$C compound), methionine (a $^{14}$C compound), tyrosine (a $^{14}$C compound), histidine (a $^{14}$C compound), tryptophan (a $^{14}$C compound) and valine (a $^{14}$C compound) were used as substrates.

Example 8

Control of Cell Proliferation by Suppression of the Neutral Amino Acid Transporter LAT1

(1) Inhibition of Suppressing the Cell Proliferation by an LAT1 Suppression.

A suppressing effect to the cell proliferation of a LAT1 suppression by an LAT1 suppressive agent was tested.

A rat liver cell line where LAT1 was highly expressed was incubated on a William's medium, 20 mM of D-leucine or BCH which suppressed the incorporation mediated by LAT1 were added to the medium and, by means of an incubation for 48 hours, cell numbers were investigated using a Cell Counting Kit-8 (manufactured by Dojindo Laboratories). The cell numbers were measured as an absorption at 450 nm (O.D. 450).

Figure 20:
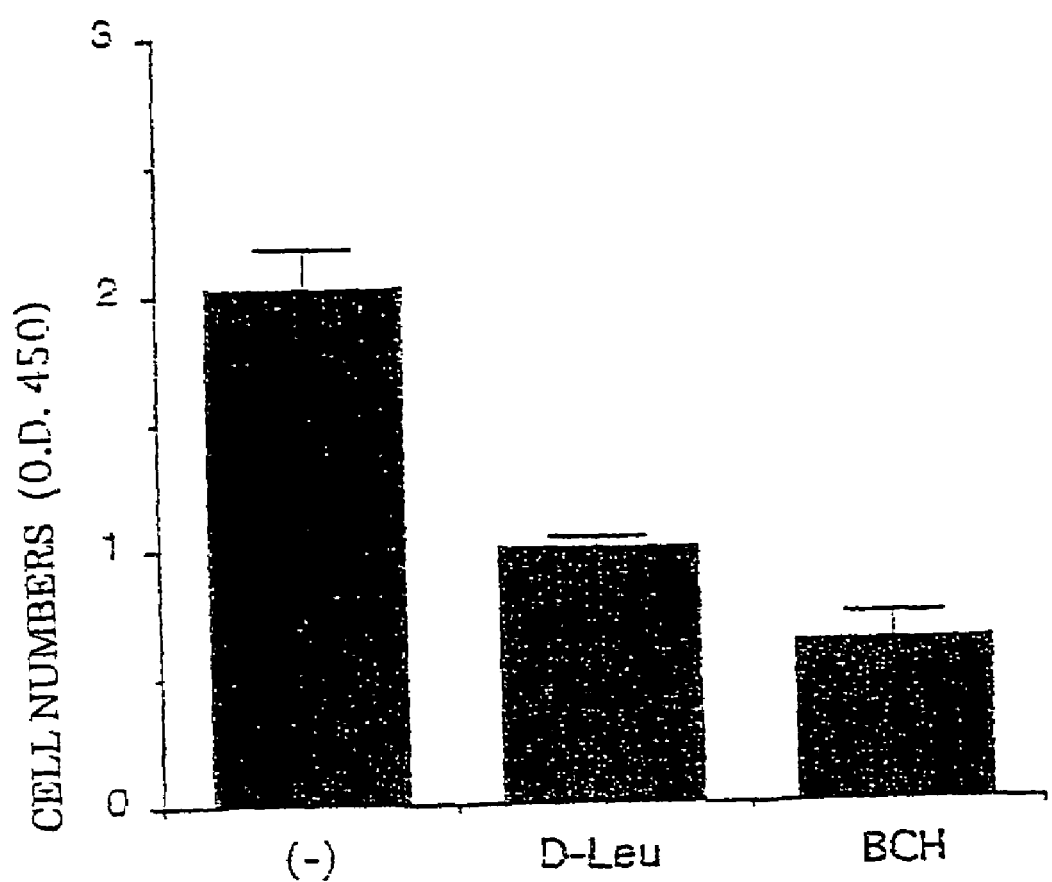
FIG. 20 shows the result of testing the influence of addition of D-leucine or BCH to a medium on cell proliferation in an cultured rat liver cell line.

The result (FIG. 20) was that, in a group where D-leucine or BCH was added, a reduction in the cell numbers was noted as compared with a control group where neither D-leucine nor BCH was added whereupon it was believed that cell proliferation was suppressed by a neutral amino acid incorporation suppression by LAT1 suppression.

Example 9

Expression of LAT1 Gene and 4F2hc Gene in Various Tumor Cell Lines of Human Being (an Analysis by a Northern Blotting)

A cDNA fragment corresponding to 649th to 1128th bases of the hLAT1 gene was excised by a restriction enzyme SmaI, a probe was prepared by labeling with $^{32}$P-dCTP and a northern blotting to human tumor cell line was carried out as follows. From various human tumor cell lines was extracted poly(A)$^{+}$RNA and then hybridization and washing using $^{32}$P-dCTP labeled LAT1 probe were carried out.

The cDNA fragment corresponding to 106th to 645th bases of the h4F2hc gene was excised by a restriction enzyme PstI, a probe was prepared by labeling with $^{32}$P-dCTP and a northern blotting to human tumor cell line was carried out in the same manner.

Figure 21:
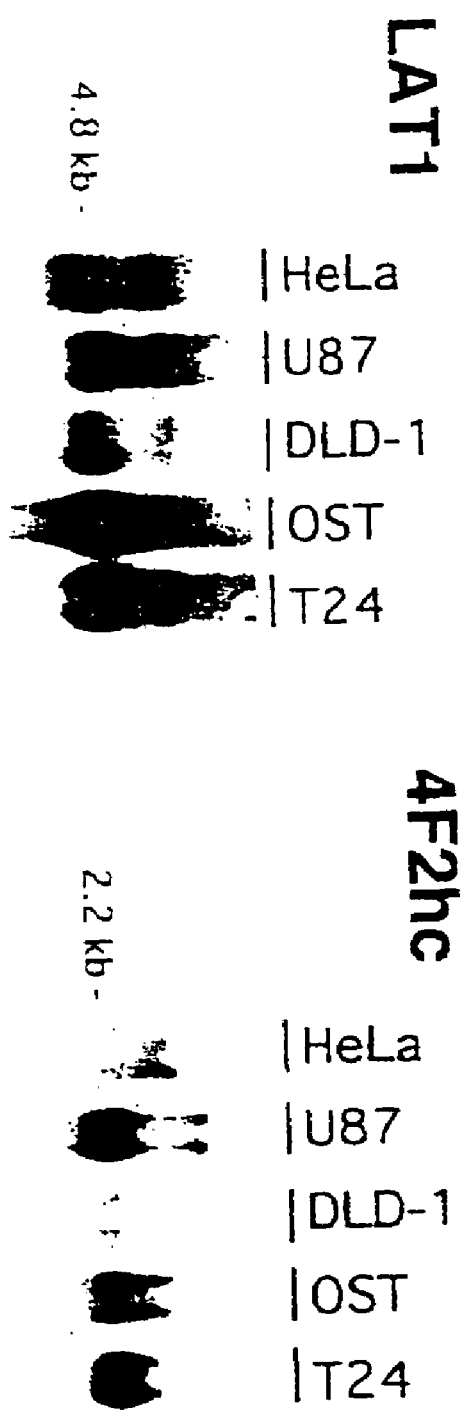
FIG. 21 is a photograph as a substitute for a drawing which shows the result of analysis of expression of LAT1 gene mRNA and 4F2hc gene mRNA in cultured human tumor cell line by a northern blotting.
Figure 22:
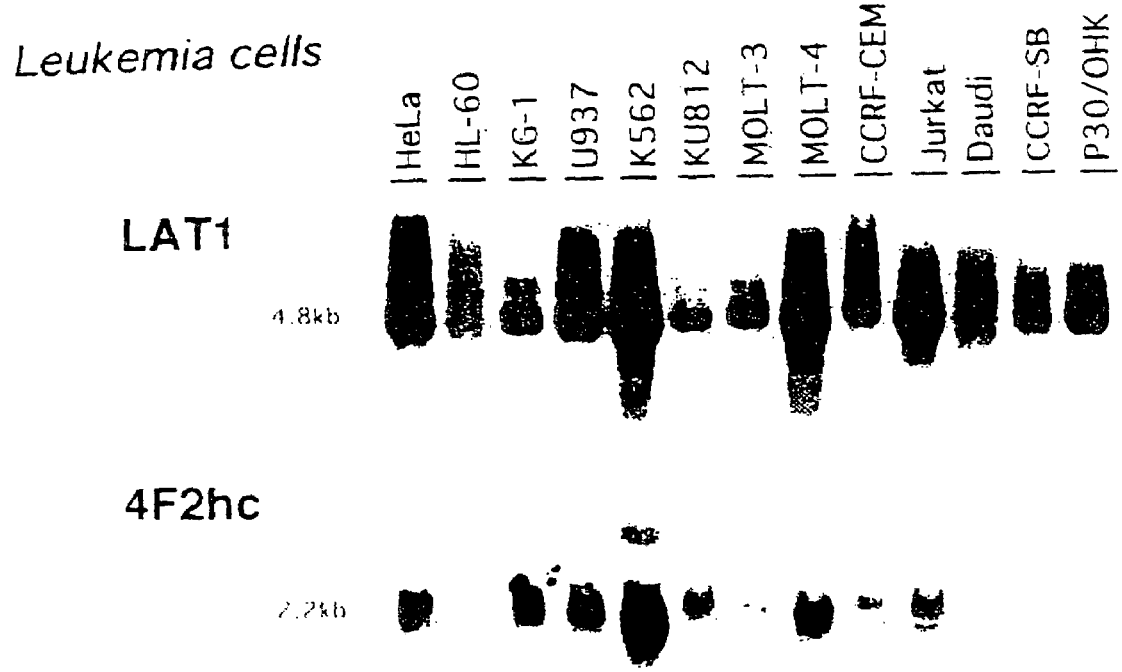
FIG. 22 is a photograph as a substitute for a drawing which shows the result of analysis of expression of LAT1 gene mRNA and 4F2hc gene mRNA in cultured human tumor cell line (leukemia cells) by a northern blotting.

As a result of the northern blotting, in all tumor cell lines investigated in FIG. 21 and FIG. 22, expression of LAT1 was noted near 4.8 kb. With regard to the 4F2hc, expression was noted in most of the tumor cell lines near 2.2 kb. However, strength of the expression varied depending upon the cells and, particularly in the case of leukemia cell lines Daudi, CCRF-SB and P30/OHK, no signal by a northern blotting was detected (FIG. 22).

Example 10

Significance of T24 Cells Derived from Human Bladder Cancer as an Evaluating System for LAT1 Inhibitors T24 cells derived from human bladder cancer were incubated and maintained in an Eagle's minimal essential medium containing 10% of fetal bovine serum. A test for the incorporation of amino acids into T24 cells was carried out by incubating the T24 cells on a 24-well plate and finished when the state became confluent. The amino acid incorporation test was started by removing the incubating solution and adding a Dulbecco's PBS (manufactured by Gibco) containing $^{14}$C-amino acid and finished by removing it, cooling with ice and washing with a Dulbecco's PBS. After washing, the above was dissolved in 0.1N NaOH and the radioactivity was measured by a liquid scintillation counter.

(1) Na$^{+}$-Dependency of T24 Cells for the Incorporation of Leucine.

Influence of sodium ion in the medium on the leucine incorporation experiment by T24 cells was investigated.

With regard to the solution for the incorporation, a choline uptake solution (where sodium chloride was substituted with choline chloride) was used in place of a Dulbecco's PBS when influence of sodium ion in the medium on the incorporation of leucine was checked.

Figure 23:
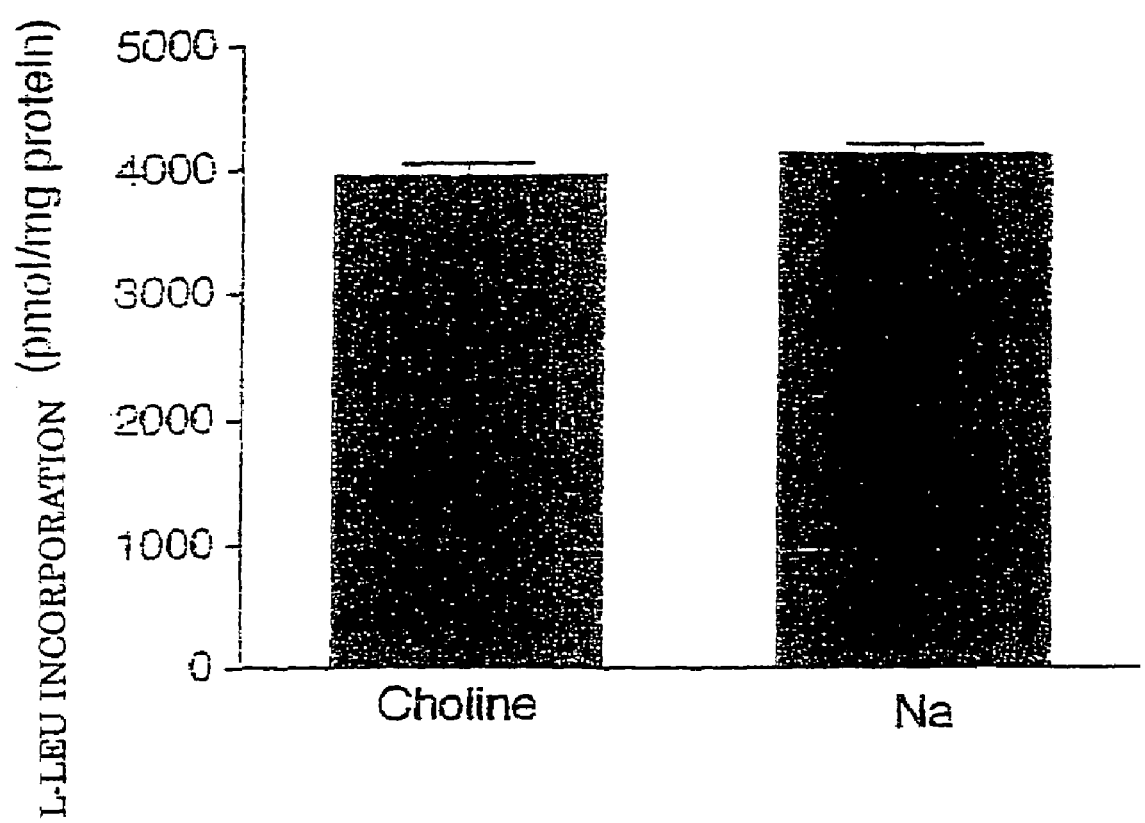
FIG. 23 shows the result of $Na^+$ dependency of leucine incorporation of T24 cells.

As a result (FIG. 23), there was no affection at all for the incorporation of leucine even when choline outside the cells was changed to sodium. Therefore, it was noted that the incorporation of leucine by T24 cells was carried on a transport system which was not dependent upon sodium ion.

(2) Michaelis-Menten Kinetic Test for the Incorporation of Leucine by T24 Cells.

A Michaelis-Menten kinetic test was carried out for the incorporation of leucine by T24 cells. The Michaelis-Menten kinetic test was conducted by investigating the changes in the incorporated rate of leucine by the difference in the concentration of the substrate leucine.

As a result (FIG. 24), Km value was 100.3 μM and Vmax value was 23,870 pmol/mg protein/minute.

(3) Experiment on the Inhibition of Incorporation of Leucine by T24 Cells by Addition of Amino Acid and Similar Substance thereto.

In an experiment of the incorporation of leucine by T24 cells, influence of addition of various amino acids and similar substances thereto was investigated.

In an experiment of the incorporation of leucine, the incorporation of $^{14}$C-leucine (20 μM) in the presence and absence of 2 mM of various compounds (unlabeled) was measured.

Figure 25:
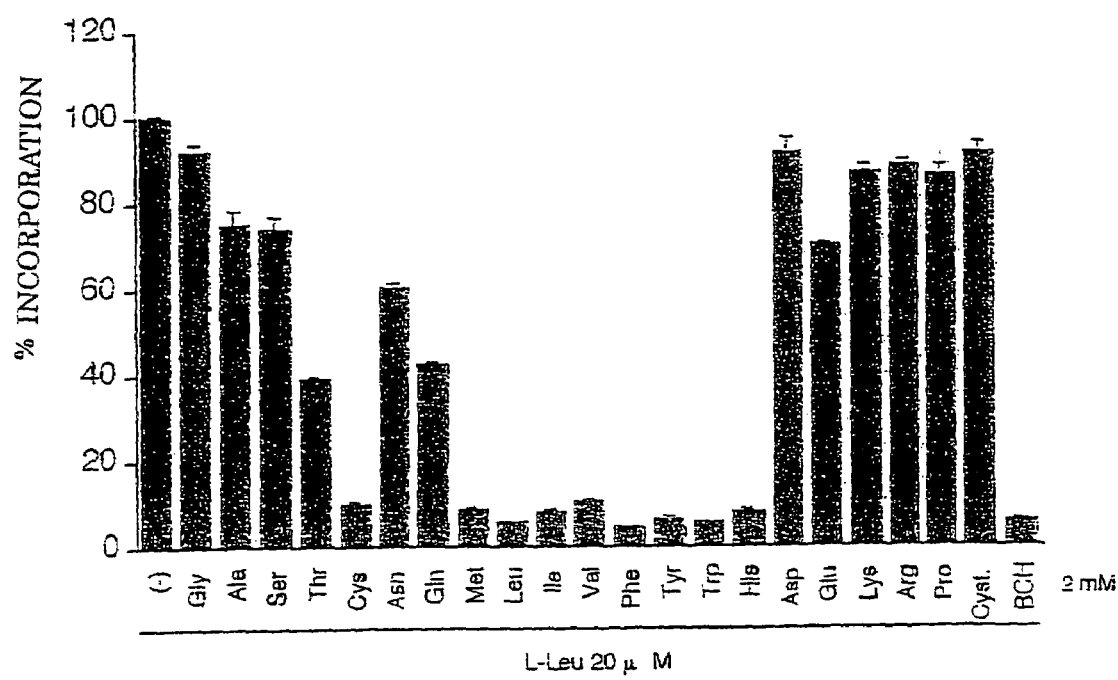
FIG. 25 shows the result of influence of addition of various amino acids or similar compounds to the system in the leucine incorporation experiment by T24 cells.

As a result (FIG. 25), a strong cis-inhibiting effect was observed by methionine, leucine, isoleucine, valine, phenylalanine, tyrosine, tryptophan, histidine and cysteine. BCH which was an amino acid transport system L-specific inhibitor strongly inhibited the incorporation of leucine. The result of this inhibiting experiment was identical with the result when LAT1 was expressed in the oocytes of *Xenopus*.

(4) Inhibiting Mode of the Leucine Incorporation by T24 Cells by BCH, an Incorporation Inhibitor.

Dependency of the $^{14}$C-leucine incorporation by T24 cells on the concentration was measured in the absence of BCH, in the presence of 50 μM of BCH and in the presence of 100 μM of BCH and the inhibiting mode was investigated by means of double reciprocal plots.

Figure 26:
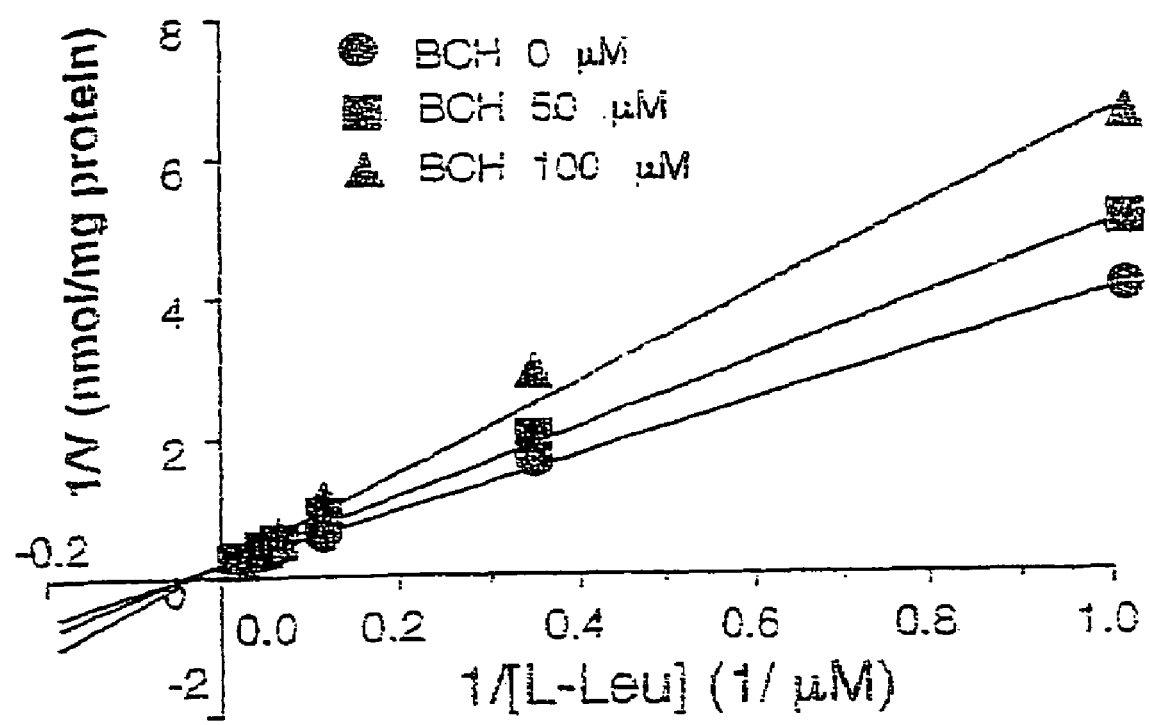
FIG. 26 shows the result of analysis of the effect of BCH using double reciprocal plots in a leucine incorporation experiment by T24 cells.

As a result (FIG. 26), it was clarified that the inhibition by BCH was a competitive inhibition and its Ki value was 156 μM.

Example 11

Effect of BCH, an Amino Acid Incorporation Inhibitor, on the Proliferation of Human Tumor Cell Line T24 cells derived from human bladder cancer were incubated and maintained in an Eagle's minimal essential medium containing 10% of fetal bovine serum. Human Daudi cells were incubated and maintained in an RPMI medium containing 20% of fetal bovine serum. T24 cells or Daudil cells were incubated in a 24-well plate (800 cells/well) for 5 days in a medium with or without 20 mM of BCH and the cell numbers were counted.

Figure 27:
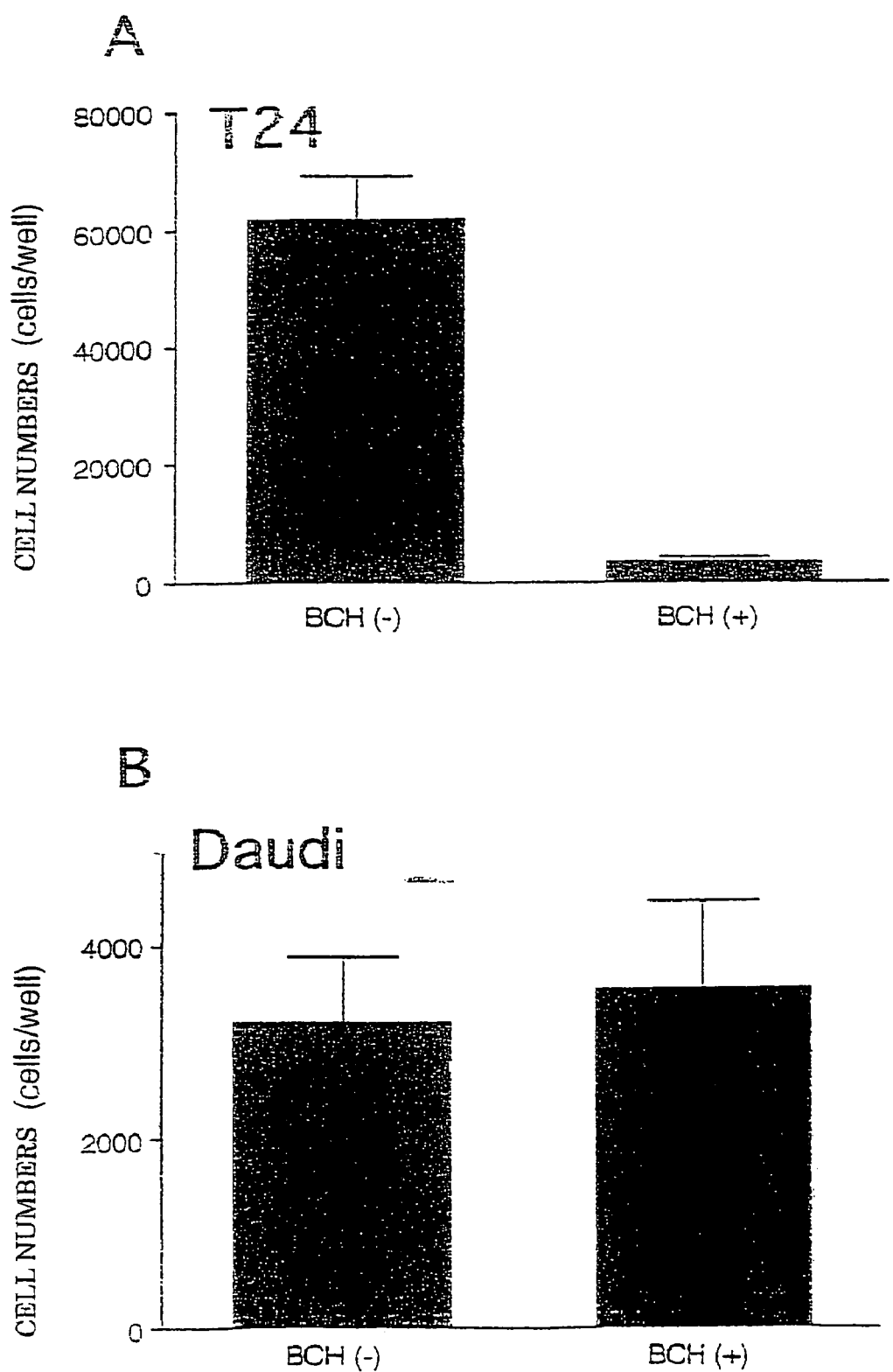
FIG. 27 shows the effect of BCH on the growth of T24 cells (A) and Daudi cells (B).

As a result (FIG. 27), it was clarified that the cell proliferation was rapid in the case of T24 cells as compared with in the case of Daudi cells and that, although BCH highly suppressed the proliferation of T24, it rarely showed a suppressing effect for the proliferation of Daudi cells.

T24 cells were strongly expressed together with LAT1 and 4F2hc (FIG. 21) and, as shown in Example 10, LAT1 showed a strong function activity in T24 cells. On the contrary, in Daudi cells, although LAT1 was strongly expressed, no expression of 4F2hc necessary for achieving the function of LAT1 was detected (FIG. 22) and, therefore, it is believed that, in Daudi cells, LAT1 does not function. The fact that the proliferation of T24 cells having a strong function activity of LAT1 was rapid, that BCH showed a high suppression for cell proliferation, that the proliferation of Daudi cells where LAT1 was believed not to function was slow and that BCH showed no effect of suppression of the proliferation supports the hypothesis that the incorporation of essential amino acids mediated by LAT1 forms one of the rate-determining steps for the cell proliferation and that such a inhibition shows the suppression of cell proliferation.

In CCRF-SB cells and P30/OHK cells (FIG. 22) where expression of 4F2hc was not detected like Daudi cells, it was confirmed that, like Daudi cells, the proliferation was slow and the effect of BCH was weak and that, like T24 cells, the proliferation was quick in the cells where both LAT1 and 4F2hc were strongly expressed and BCH showed a strong suppressing effect.

Example 13

Survival Effect of BCH, an Amino Acid Transporter Suppressor, in Tumor-Inoculated Mouse Mouse sarcoma 180 cells were intraperitoneally transplanted ($1 \times 10^6$) to male ICR mouse and, from the next day of the transplantation, BCH which was a inhibitor for the amino acid transporter, D-Leu having a inhibiting effect on amino acid transporter and D-Ala having no inhibiting action thereon were administered at the dose of 300 mg/kg for ten days. After the transplantation, it was confirmed every day whether the mouse was dead or alive.

Figure 28:
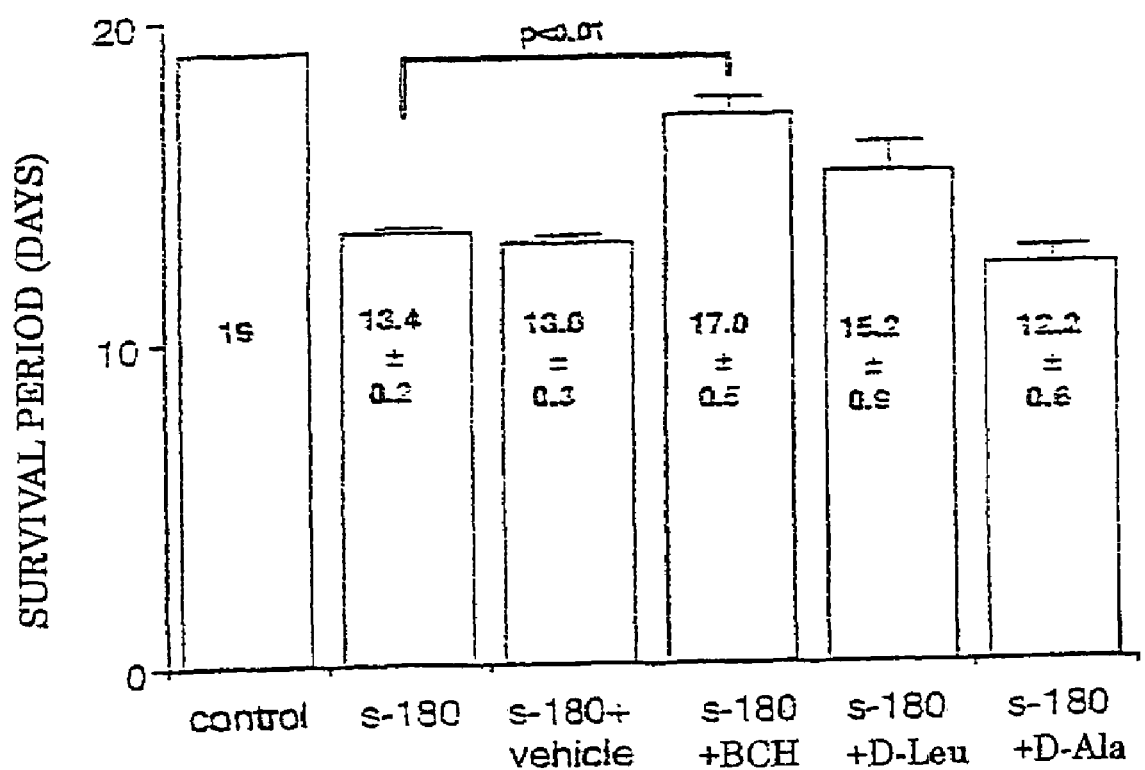
FIG. 28 shows the result of investigation of survival effect by BCH, D-Leu and D-Ala after intraperitoneal transplantation of mouse sarcoma 180 cells to ICR mouse.

As a result of the observation for 19 days, all cases were alive in the untreated control while, in the group inoculated with sarcoma 180 cells, the group inoculated with sarcoma 180 cells and the group administered with a vehicle after inoculation of sarcoma 180 cells, the living periods were significantly shortened as compared with the control (FIG. 28). On the contrary, in the group where BCH was administered or D-Leu was administered after the inoculation of sarcoma 180 cells, a significant survival effect by treatment with such an agent was noted (FIG. 28). No survival effect was noted in D-Ala (FIG. 28).

INDUSTRIAL APPLICABILITY

The amino acid transporter molecule of the present invention has an important biological function of mediating the incorporation of various amino acids which are essential nutrients for the manufacture and the proliferation of cells and, in addition, it shows an expression in a broad range of tumor cells as compared with the expression in normal cells whereby the molecule is quite hopeful as a target in the development of, for example, antitumor agents (anticancer agents).

Thus, when a pharmaceutical agent having the biological activity on the molecule or the activity for suppressing the expression of the molecule (such as antisense DNA pharmaceutical agent, antisense RNA pharmaceutical agent, antibody pharmaceutical agent, antibody fragment pharmaceutical agent, peptide antagonist pharmaceutical agent and non-peptide antagonist pharmaceutical agent such as low-molecular compounds) is used and suppresses the incorporation of the nutrients (various amino acids and physiologically active substances) mediated by the molecule into the tumor cells, it is now possible to make the tumor cells in a state of amino acid starvation and to inhibit the existence and the proliferation of tumor cells.

Accordingly, the protein of the present invention or a part thereof, DNA coding for the protein or a part thereof, RNA coding for the protein or a part thereof, DNA which hybridizes to the DNA, expression vector containing the DNA, transformed cell which is transformed by the DNA or by the vector, cell into which the RNA is introduced, antibody or a part thereof having a reactivity with the protein or a part thereof, cell which produces the antibody, labeled DNA where the a part of the DNA is radiolabeled, labeled RNA where a part of the RNA is radiolabeled, labeled antibody where the antibody or a part of the antibody is labeled, a kit comprising the labeled DNA, a kit comprising the labeled RNA and a kit comprising the labeled antibody are able to be provided as pharmaceutical agents having such an antitumor effect and/or reagents in the development of such pharmaceutical agents.

In addition, when various substances such as DNA, RNA or transformed cells of the present invention are used, it is now possible to conduct a drug design, a screening (such as a reporter gene assay) and an identification of pharmaceutical agents which control (activate, suppress or inhibit) the biological activity of the protein of the present invention, pharmaceutical agents which inhibit the transcription of the protein of the present invention to mRNA, pharmaceutical agents which inhibit the translation of the protein of the present invention from the mRNA, pharmaceutical agents which inhibit the interaction of the protein with other molecules, etc.

Further, a part of DNA and RNA of the present invention is able to be provided as a probe in the identification of DNA or RNA which hybridizes therewith using a colony hybridization method or a plaque hybridization method. Furthermore, a part of DNA of the present invention is able to be provided as a primer for the amplification of the gene coding for DNA of the present invention or transporter molecule of the present invention by a PCR.

Still further, a part of DNA of the present invention, DNA complementary to the DNA or a part of RNA of the present invention is able to be provided not only as the above-mentioned reagent but also as the so-called antisense DNA pharmaceutical agent or antisense RNA pharmaceutical agent.

As mentioned above, the protein of the present invention is able to identify the pharmaceutical agent which controls the biological activity of the protein of the present invention or the expression of the protein when the state where the protein molecule is expressed on the cell surface is utilized. It is also possible that, based upon the amino acid sequence of the protein, a peptide antagonist having an ability of inhibiting the biological activity of the protein is designed. The peptide antagonist which is designed as such competitively inhibits the bond of the amino acid transporter which is the protein of the present invention with various substrates or the bond of the protein of the present invention with other molecule whereby it is able to be provided as a pharmaceutical agent which does not make the biological function of the protein of the present invention achieved.

The protein of the present invention or a part thereof and cells such as a transformed cell expressing the protein are able to be provided as immune sensitizing antigens in the preparation of antibody (antiserum, monoclonal antibody) to the protein of the present invention.

Antiserum (polyclonal antibody) and monoclonal antibody having a reactivity with the amino acid transporter molecule which is the protein of the present invention are able to be provided as an antibody pharmaceutical agent where achievement of the biological activity of the molecule is inhibited (neutralized) when bonded to the molecule.

Further, when the antibody is labeled with various substances which are able to give a detectable signal, it is able to be provided as a reagent in the analysis (immunohistological staining, western blotting, ELISA, etc.) of expressed state of the protein of the present invention in various biological materials (such as cells, tissues, organs and body fluid).

As same as such a labeled antibody, the labeled DNA labeled with various substances being able to give a signal by which DNA of the present invention or a part thereof is detectable can be provided as a reagent in the test (such as a southern blotting and an FISH) in the identification of the gene coding for the protein of the present invention.

Further and similarly, a radiolabeled RNA where the RNA of the present invention or a part thereof is labeled with a radioisotope is able to be provided as a reagent in the analysis (such as a northern blotting) of the expressed state of mRNA coding for the protein of the present invention in cells, tissue or organs.

---

The invention claimed is:

1. A method for screening a test substance having an action of suppressing the ability for transport of a neutral amino acid into a cell by a cell surface protein having an ability to mediate the incorporation of at least one amino acid selected from the group consisting of leucine (Leu), isoleucine (Ile), phenylalanine (Phe), methionine (Met), tyrosine (Tyr), tryptophan (Trp), valine (Val), histidine (His) and other neutral amino acids into the cell in an Na$^+$-independent manner, wherein the cell surface protein has an amino acid sequence selected from a) to d);
 a) amino acid sequence represented by SEQ ID NO:2,
 b) amino acid sequence represented by SEQ ID NO:4,
 c) amino acid sequence represented by SEQ ID NO:2, wherein 1 to 20 amino acid residue(s) is (are) substituted, deleted or added,
 d) amino acid sequence represented by SEQ ID NO:4, wherein 1 to 20 amino acid residue(s) is (are) substituted, deleted or added.

2. The method according to claim 1, wherein the cell is transformed by a DNA coding for a cell surface protein having an ability to mediate the transport of an amino acid into the cell and having an ability to mediate the incorporation of at least one amino acid selected from the group consisting of leucine (Leu), isoleucine (Ile), phenylalanine (Phe), methionine (Met), tyrosine (Tyr), tryptophan (Trp), valine (Val), histidine (His) and other neutral amino acids into the cell in an Na$^+$-independent manner, wherein the protein has an amino acid sequence selected from a) to d):
 a) amino acid sequence represented by SEQ ID NO:2,
 b) amino acid sequence represented by SEQ ID NO:4,
 c) amino acid sequence represented by SEQ ID NO:2, wherein 1 to 20 amino acid residue(s) is (are) substituted, deleted or added,
 d) amino acid sequence represented by SEQ ID NO:4, wherein 1 to 20 amino acid residue(s) is (are) substituted, deleted or added.

3. The method according to claim 2, wherein the cell is an oocyte of Xenopus laevis.

4. The method of claim 1 or 2, where the cell surface protein coexists with a 4F2hc protein classified under a type II membrane glycoprotein or a part thereof, and the cell surface protein has an ability to transport one or more neutral amino acids.

5. The method of claim 4, wherein the 4F2hc protein classified under the type II membrane glycoprotein is a protein having the amino acid sequence of SEQ ID NO: 6 or SEQ ID NO: 8 or an amino acid sequence where a part of the amino acid seaquence thereof is deleted, substituted or added.

6. The method of any one of claims 1, 4, or 5, wherein the cell surface protein is derived from human being or rat.

7. The method of claim 2, wherein the DNA is derived from a human being or rat.

8. The method of claim 2, wherein the DNA coding for a cell surface protein hybridizes under stringent conditions to DNA having a base sequence from the 66th to the 1586th base of SEQ ID NO: 1 or having a base sequence from the 64th to the 1599th base of SEQ ID NO: 3.

9. The method of claim 4, wherein the 4F2hc protein 4F2hc protein classified under the type II membrane glycoprotein has the amino acid sequence of SEQ ID NO: 6 or SEQ ID NO: 8 or an amino acid sequence where a part of the amino acid sequence is deleted, substituted or added.

* * * * *